(12) United States Patent
Scanlan et al.

(10) Patent No.: US 6,686,147 B1
(45) Date of Patent: Feb. 3, 2004

(54) CANCER ASSOCIATED ANTIGENS AND USES THEREFOR

(75) Inventors: Matthew J. Scanlan, New York, NY (US); Ali Gure, New York, NY (US); Lloyd J. Old, New York, NY (US); Yao-Tseng Chen, New York, NY (US); Barbara Williamson, New York, NY (US)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/392,714

(22) Filed: Sep. 9, 1999

Related U.S. Application Data

(63) Continuation-in-part of application No. PCT/US98/14679, filed on Jul. 15, 1998.

(51) Int. Cl.[7] .................................................. C12Q 1/68
(52) U.S. Cl. ........................ 435/6; 435/91.1; 435/91.2; 435/94; 536/23.5; 536/24.3; 536/24.31
(58) Field of Search .......................... 435/6, 91.1, 91.2, 435/94; 536/23.5, 24.3, 24.31

(56) References Cited

FOREIGN PATENT DOCUMENTS

| | | |
|---|---|---|
| EP | 0 869 176 A1 | 10/1998 |
| GB | 2 273 099 A | 6/1994 |
| WO | WO 98/08866 | 3/1988 |
| WO | WO 92/20356 | 11/1992 |
| WO | WO 95/23874 | 9/1995 |
| WO | WO 96/10413 | 4/1996 |
| WO | WO 96/15149 | 5/1996 |
| WO | 96/29409 * | 9/1996 |
| WO | WO 97/02362 | 1/1997 |
| WO | WO 97/17441 | 5/1997 |
| WO | WO 97/17470 | 5/1997 |
| WO | WO 97/21729 | 6/1997 |
| WO | WO 98/32853 | 7/1998 |
| WO | WO 98/40483 | 9/1998 |
| WO | WO 98/48015 | 10/1998 |

OTHER PUBLICATIONS

Franzen et al., *British J of Cancer* 73:1632–1638, 1996.
Sahin et al., *Proc. Natl. Acad. Sci. USA* 92:11810–11813, Dec. 1995.
Alalya et al., *Int. J. Cancer* 73:678–683, 1997.
Gure et al., *Cancer Research* 58:1034–1041, 1998.
Scanlan et al., *Int. J. Cancer* 76:652–658, 1998.
Nagase et al., *DNA Research* 5:31–39, 1998.
Jones, M., et al., *Genomics* 45:529–534, 1997.
Ishikawa, et al., *DNA Research* 5:169–176, 1998.
Drabkin et al., *Oncogene* 18:2589–2597, 1999.
Vaughan et al., *Amer. Soc. for Clin. Invest., Inc.* 95:1306–1315, Mar. 1995.
Mashimo et al., *Cancer Letters* 113:213–219, 1997.
Machiels et al., *J. of Pathology* 182:197–204, 1997.
Coates et al., *J. of Pathology*, 178:21–29, 1996.
Zwijsen et al., *FEBS*, 937–946, 1994, vol ?.
Minegishi et al., *J. Exp. Med.* 184:1365–1375, Oct. 1996.
Jin et al., *Proc. Natl. Acad. Sci, USA* 90:7769–7773, Aug. 1993.
Noce et al., *Devel. Biology* 153:356–367, 1992.
Ono et al., *J of Virology*, 589–598, Nov. 1986.
Hung and Schreiber, *Biochem. and Biophys. Res. Comm.*, 184(2):733–738, Apr. 30, 1992.
Jin et al., *J. of Biol. Chem.* 267(16):10942–10945, 1992.
MacLeod et al., *Proc. Natl. Acad. Sci. USA* 82:7835–7839, Dec. 1985.
Adams et al., *Nature* 4:373–379, Aug. 1993.
Adams et al., *Nature* 377:3–174, Sep. 28, 1995.
Miki et al., *Science* 266:66–71, Oct. 7, 1994.
Nagase et al., *DNA Research* 3:321–329, 1996.
Li et al., *Gene* 143:303–304, 1994.
Fisher et al., *Proc. Natl. Acad. Sci. USA* 83:6450–6454, Sep. 1986.
Boon et al., *Immunol. Today* 18(6):267–268, Jun. 1997.
Hinds et al., Acc. No. AC004022, "*Homo sapiens* BAC clone Gs155MII . . . " Jan. 22, 1998. (XP–002091837).
Hillier et al., Acc. No. AA454222, "zx48g12.s1 Soares testis NHT *Homo sapiens* . . . " Jun. 11, 1997. (XP–002103189).
Hillier et al., Acc. No. AA454221, "zx48g12.r1 Soares testis NHT *Homo sapiens* . . . " Jun. 11, 1997. (XP–002103190).
Fujiwara et al., Acc. No. C15995, "Human fetal brain cDNA 5'–end GEN–421G02" Sep. 29, 1996. (XP–002103191).
Hillier et al., Acc. No. W45570, "zc26f08.s1 Soares senescent fibroblasts . . . " May 27, 1996. (XP–002103192).
Hillier et al., Acc. No. AA007407, "zh97b08.r1 Soares fetal liver spleen . . . " Jul. 28, 1996. (XP–002103193).
Marra et al., Acc. No. AA184412, "mt34f07.r1 Soares mouse 3NbMS *Mus musculus* . . . " Feb. 19, 1997. (XP–002103194).

(List continued on next page.)

*Primary Examiner*— Susan Ungar
*Assistant Examiner*—Minh Tam Davis
(74) *Attorney, Agent, or Firm*—Wolf, Greenfield & Sacks, P.C.

(57) ABSTRACT

Cancer associated antigens have been identified by autologous antibody screening of libraries of nucleic acids expressed in testis cells using antisera from seminoma patients. The invention relates to nucleic acids and encoded polypeptides which are cancer associated antigens expressed in patients afflicted with a variety of cancers. The invention provides, inter alia, isolated nucleic acid molecules, expression vectors containing those molecules and host cells transfected with those molecules. The invention also provides isolated proteins and peptides, antibodies to those proteins and peptides and cytotoxic T lymphocytes which recognize the proteins and peptides. Fragments of the foregoing including functional fragments and variants also are provided. Kits containing the foregoing molecules additionally are provided. The molecules provided by the invention can be used in the diagnosis, monitoring, research, or treatment of conditions characterized by the expression of one or more cancer associated antigens.

4 Claims, No Drawings

OTHER PUBLICATIONS

Adams et al., Acc. No. T09468, "EST07361 *Homo sapiens* cDNA clone . . . " Aug. 8, 1993. (XP–002103195).

Hillier et al., Acc. No. AA133416, "zk96e08.r1 Soares pregnant uterus NbHPU . . . " Dec. 6, 1996. (XP–002103196).

Hillier et al., Acc. No. AA487071, "ab18f11.s1 Stratagene lung . . . " Jun. 28, 1997. (XP–002103197).

Vaughan et al., Acc. No. L38696, "*Homo sapiens* autoantigen p542 mRNA . . . " Feb. 17, 1995. (XP–002103198).

Adams et al., Acc. No. AA327309, "EST30621 Colon I *Homo sapiens* cDNA 5' end" Apr. 18, 1997. (XP–002103199).

Hillier et al., Acc. No. AA121190, "z188g08.r1 Stratagene colon . . . " Nov. 21, 1996. (XP–002103200).

Nathans, J., Acc. No. W22160, "63A6 Human retina cDNA . . . " May 9, 1996. (XP–002103201).

Hillier et al., Acc. No. AA121174, "z188g08 Stratagene colon . . . " Nov. 21, 1996. (XP–002103202).

Hillier et al., Acc. No. AA029201, "zk12f08.s1 Soares pregnant uterus NbhPU . . . " Aug. 20, 1996. (XP–002103203).

Nathans, J., Acc. No. W29097, "56d11 Human retina cDNA . . . " May 14, 1996. (XP–002103204).

Miki et al., Acc. No. AF039241, "*Homo sapiens* clone 11–67js . . . " Jan. 17, 1998. (XP–002103205).

Marra et al., Acc. No. AA221749, "my28g01.r1 Barstead mouse pooled organs . . . " Feb. 15, 1997. (XP–002103206).

Nomura, N., Acc. No. D87455, "Human mRNA for KIAA0266 gene, complete cds" Nov. 9, 1996. (XP–002103207).

Hillier et al., Acc. No. AA151187, "zo03c11.r1 Stratagene colon . . . " Dec. 15, 1996. (XP–002103208).

Latif et al., Acc. No. U50839, "*Homo sapiens* g16 protein . . . " Mar. 9, 1997. (XP–002130209).

Nat. Cancer Inst., Acc. No. AA285170, "zs48f04.s1 NCI_CGAP_GCB1 *Homo sapiens* . . . " Apr. 5, 1997. (XP–002103210).

Noce, T., Acc. No. D10630, "Mouse mRNA for zinc finger protein, complete cds" Nov. 8, 1992. (XP–002104555).

Ohara et al., Acc. No. AB011172, "*Homo sapiens* mRNA for . . . " Apr. 10, 1998. (XP–002104556).

Scanlan et al., *Biochimica et Biophysica Acta* 1445:39–52, 1999.

Kibel, AS et al, 2000, J urol, 164(1):192–6.*

Ren, C et al, 1998, Cancer Res, 58(6): 1285–90.*

Gingrich, JR et al, 1996, Cancer res, 56(18):4096–4102.*

MPSRCH Search Report, p. 25, 2002.*

Jauser, Pediatric. Res. 37(6):681–686, 1995.*

Alberts. Mol. Biol. Cell $3^{rd}$ ed, p. 465, 1994.*

Shautz, Intl. J. Biochem. Cell Biol. 31:107–122, 1999.*

McClean, Eurj. Cancer, 29A: 2243–2248, 1993.*

Fu, EMBO J. 15:4392–4401. 1996.*

Yokota, J. Oncogene, 3:471–475, 1988.*

Burgess, J. Cell Biol. 11:2129–2138, 1990.*

Lazar, Mol. cell Biol. 8:1247–1252, 1988.*

Tao, J. Immunol, 143(8):2595–2602, 1989.*

Grillies, Hu Antibiol. Hylan domas 1(1):47–54, 1990.*

Shautz, CM. Intl. J. Biochem & Cell Biol. 31: 107–122, 1999.*

Fu, L. et al. Embo J. 15 (16):4392–4401, 1996.*

* cited by examiner

SEQUENCE LISTING

<160> NUMBER OF SEQ ID NOS: 30

<210> SEQ ID NO 1
<211> LENGTH: 14561
<212> TYPE: DNA
<213> ORGANISM: Homo sapiens -continued

```
<400> SEQUENCE: 1
tccacacccc tggcggttcc aggcaggcta cgccacgcga cccctcccgt ttccctgctt      60
tggccaatgg aggagctacg aatggcacga cctgctcgag cttggcagtc tccagttggg     120
ctgtgcatgg aagcttggga agactttgtt ggaaggggag gcgggagag agtgctggag      180 gctctgggc gatggcttcc gcacctcttc aaccaccct ctttccctgg agtcggcgga       240
ccacagctca gccaattggc ttggagatgt ggcgggttgc cacttccctg tgggtctctg     300
cggcactctt ctgcctggtg actgacacct tggaaatgaa gtttatgacg tcatcgttgc     360
ggctggccaa tagaaaaagc tcccgcggag aggtgttcct tccccttcga ctcagcttct     420
tcacccgcgt gagcgagcgc gcgcgcgcgg agggggtggg gaaaatctca agcagggtgg     480
cgcgcatgag cggcgaagct cctcctcccc gcctatatat aaagggctgg cgcggggctc     540
ggcggcgcca tttcgtgctg gagtggagca gcctctagaa cgagctggag gattctgcct     600
accgatacag agccttcgag tcgtccgggg ccgccattac aatccacctc catccgcttg     660
gaaatggcct tcgtcccggc ctatgactgg tcccagcggg cagtacagac cccctagaag     720
cccctggagc tccccttttt cgggccccgc ccaatcctcg gagtctgtcc accccctcta     780
ctccgccctc aagaggattt caaagatgga ggcggcggct ccctaaacca cttttcgtgt     840
tcatccgcct ccatccgaga tcgaaacggg acctcgtcgg ccccgtaggg gcccgacaag     900
aagagggaat ccctgcagac caacagcggg ctatattgac gacggtgtct gagatcgggg     960
accgtctttt gaagagtcag tccctcctta gttgcccgcc tcagctgagg ccgccgccat    1020
tttcttgctg tccgccgtct gcagagcgcg ccaagctgcc cggagctctc cgagaggccc    1080
caaagagact gctttcgtgc cggccaggca ggggtttgt cgcctggagg cccaagagga     1140
acggcctccc cccaacttag cgggttatgc tggaccgggc ggtgagggga accgaggcca    1200
cccggacttt ccgcggctga gggcagcgcc ggttccttgc ggtcaagatg ctgcaaaacg    1260
tgactcccca caataagtac gtttccgcga gccgcgtgtg ggaagggat gttgcagggc     1320 ggcggcacag gggtgtgggg cgccgtgttg ggagtactga gcggcccgg cgcgctgctg     1380 ttgcggcgca gctgtcgact cggtcgcgcg gagggaattg agcgacggtt ttggaacggt    1440
ggtggcggct cggctactgc tcgtggaggg aatacaggt tgtcaattta tacgctatta     1500
atgccgccgt ggcccagtct taaccgagtc aggcagagct agtttgacgg tggagtggag    1560
tgaggttgaa cagcaggttt ggcgtttggt ggtctggta tctagcggcg gtctgttagc     1620
cttttagggg ggattcacgg acacctctag cgccctgtag ggttgccatg gtgacggagc    1680
gcttaaggga ctggcaacgg ggattcccag agaagggtaa agggatcact ctcccgtgtg    1740
tgcaggttcc taatgcccag ggcatgtcat taaatctttt gctttctttg ggtgggtggg    1800
ttgtgtgtgt tgtttgttgg tgcagggatt gttttttcct aacattaaaa gtttgattca    1860
gggcaggagg gtagagctaa ggttcctagt tcagctctgc gatgtaaaca atgagattcc    1920
catatgatgt tttaattctt agtggtagg aaagactgat cggaggagca ccagagggac     1980
tgtaaatgaa ccactgttag cgtttggtgt ccggagttgg tgctacaggg ggaactggta    2040
gtggaatcgt gttgtgtagt gggtgggtgg aaggggcta tcacttggtg accttgactg     2100
ttttgtacgg cttttttgact tccttggagt gaggagactc tgatttggtg cgaataattt    2160
tgagggcctg gaagttacgg gctgtgaagt ctgacaaatt cttccttgtc tgaatttgtt    2220
tttaagttga tatggttctt cctctgggtt tctagtctat gttctgttgt ggcgtgaact    2280
acccagacct tgtggaagat ggtgctctct cttctatcta ggtggattat tctgtgtctt    2340
```

-continued

```
atcagcattt tatggaattt tttatagcca taatttgttc ttttcctcct taccggcgct    2400
caaccaccat ggcaaccacc aaaccccag  tgaggaggaa gcttgggtt  tgagtttctt    2460 aactccaccc attttgctta atccccatcc ccatagggct gtagttctga gatgtcgtgc    2520
cttgtcagaa acaatttggg agttttttaa aatatgaaaa agaacagata gagcctatca    2580
gacttaagaa ggtgggatct agatagtata ctaaaaatat taataaaagg aaggcggggc    2640
cagcaataaa agctccacag attgtttgga tattgtttct gcttaagaag cacttggcat    2700
aagcttaacc acctcactag ggccagcacc tggattcatc agactattgt gcagatgcac    2760 ttttcctca  tttggacgat attgccctaa ttttgttccc atctttacag gctccctggg    2820
gaagggaatg cagggttgct ggggctgggc ccagaagcag cagcaccagg gaaaaggatt    2880
cgaaaaccct ctctcttgta tgagggcttt gagagcccca caatggcttc ggtgcctgct    2940
ttgcaactta cccctgccaa cccaccaccc ccggaggtgt ccaatcccaa aaagccagga    3000
cgagttacca accagctgca atacctacac aaggtagtga tgaaggctct gtggaaacat    3060
cagttcgcat ggccattccg gcagcctgtg gatgctgtca aactgggtct accggtgagt    3120
agagacattg gagccgggga ggtgtgggat gagcaagaat gcgtgtgaat gggggtggtc    3180
tgcctagtgt agatgctgcg gcccctaggg agttcccatt tctcccctgt agggcagtta    3240
gctaccagat ttctgggtat cttggtcctt tgtgattgat ccgaccgctt gctgtaacta    3300
tcttggcatc tttccttgtg ccctccatgt gtccttcctt aacttttgtg ccctggctcc    3360
attttacaga ttcccacctc gggttgggag aggaccacgg tggccaaaat tcttagcttc    3420 ttccttccc  tcatgcagcc catggatagc cagccccaga ggtaatgtca caggatggga    3480
agtttccaga gtgggtggga ggtgggtggt tagagaaagg cagcagggc  ctccctgtgg    3540 atgtcaagaa tctttttat  ttatttattt attttgtccc acagtttaat tggggccgca    3600
gtttaactgt tcctttgatg cataggggt  gtgtgtgtgt gtgtgtgtgt gtgtgagagt    3660
cggggatcgg tagtctccct ataagcattt attttttctgt ggttctgacc taacattct    3720 ttatttagga ttatcacaaa attataaaac agcctatgga catgggtact attaagagga    3780
gacttgaaaa caattattat tgggctgctt cagagtgtat gcaagatttt aataccatgt    3840
tcaccaactg ttacatttac aacaaggtga gttttctgt gtgttcattt agtaggtggg     3900
gagaaacagt aatttctatt attgctggat atgttgtcta cataaagttt aaatccttg     3960 ctactgaagg tgttatccag gtagggtagt cggagtctta aaaacctgac tctagatggt    4020
actattgaac acagtgatgt gacttcagag ctctagttga aggttattta gaacacttca    4080
tacttggggg tggtggtcct gtttcttaga aatcaccaga gacctgagta gaccagggat    4140 ctgtttctt  gtcagctctc aagtttttc  ttctttcgaa ttttgggaga cagttaggag    4200
aaagtggaaa ttagtagtgg cctggagtag aaattttctt taagatttga tgacaagatg    4260
actggtgggg gtatggtaat ggcctagggc ctgaatgcct ctgagaaaga tggtgtgtat    4320
ctatcttctg ttggcatttt ttaactttct ttattgctgt ctgtgttctc atagcccact    4380
gatgatattg tcctaatggc acaaacgctg gaaaagatat tcctacagaa ggttgcatca    4440
atgccacaag aagaacaaga gctggtagtg accatcccta agaacagcca caagaagggg    4500
gccaagttgg caggtaggaa gagtgggagt tttgcaaatg gacaacttaa agatggggaa    4560
gagaatcaaa ctacacttttt ttcctttttt ctagcgctcc agggcagtgt taccagtgcc    4620
catcaggtgc ctgccgtctc ttctgtgtca cacacagccc tgtatactcc tccacctgag    4680
```

```
ataccgacca ctgtcttcaa cattccccac ccatcagtca tttcctctcc acttctcaag   4740
tccttgcact ctgctggacc cccgctcctt gctgttactg cagctcctcc agcccagccc   4800
cttgccaagg tatgatctgt ggatttcctc tgggcagcag ggaggcaagg gtcttaagta   4860
aagtgggctt ggagtgacag gttccctatc ttgtttcttt ctgcagaaaa aaggcgtaaa   4920
gcggaaagca gatactacca cccctacacc tacagccatc ttggctcctg gttctccagc   4980
tagccctcct gggagtcttg agcctaaggc agcacggctt cccctatgc gtagagagag    5040 tggtcgcccc atcaagcccc cacgcaaaga cttgcctgac tctcagcaac aacaccagag   5100
ctctaagaaa ggaaagcttt cagaacagtt aaaacattgc aatggcattt tgaaggagtt   5160
actctctaag aagcatgctg cctatgcttg cctttctat aaaccagtgg atgcttctgc     5220
acttggcctg catgactacc atgacatcat taagcacccc atggacctca gcactgtcaa   5280
ggtacccact gcatgggca gatgggatgc tcaagcagtg atgggagcct aggtgcaaaa    5340
caataagtct ccttatgtgg gcacacagca gtctttggtt cttggcattt tacttttata   5400
aaataatagt ggaacagaag gtctggtgtt ttgagaattt gtatttcttg gagtttgaaa   5460
cagtagggtg gggtttcttt gtcttgagaa aaatactgtc tataattaag tactaatgtg   5520
gcagtgttgg gttaaggaag ttataggtgt gaaagacagg cataggccac ctctctgtca   5580
cttagaaatg atttctttttt ctagacataa atatttcttc aacccaccca aattcctttg   5640
acttcaaact tgaaccccag ggcacagatc cttaaggtca tccccactgt gctctcaaga   5700
gagggctctt cttgtggtgt ctggggttgg cagggaaagg tgagtcttcc tgcctgtgca   5760
gcttctgatg ctgcctcctt ctgcagcgga agatggagaa ccgtgattac cgggatgcac   5820
aggagtttgc tgctgatgta cggcttatgt tctccaactg ctataagtac aatcccccag   5880
atcacgatgt tgtggcaatg gcacgaaagc tacaggtgag tggaaaggtt ggagtttgaa   5940
aaataaatgt tatgggagt tattttgtca tgtgtgctgc atagcctcaa cgtgagggtc     6000
tcactgttct gtacagttgt aaattggagc tatatcactt ggtggctggg tatgtagggc   6060
actgtttatc agcatagttt tgagtttgtg cctctttcta ggatgtattt gagttccgtt   6120
atgccaagat gccagatgaa ccactagaac cagggccttt accagtctct actgccatgc   6180
cccctggctt ggccaaatcg tcttcagagt cctccagtga ggaaagtagc agtgagagct   6240
cctctgagga agaggaggag aagatgagg aggacgagga ggaagaagag agtgaaagct    6300
cagactcaga ggaagaaagg gctcatcgct tagcagaact acaggaacag gtattttgtc   6360
actcttgaaa gtttttattg ggtaagaggt tcatgccctt tgtcctcatt ttttcttctt   6420
gttattttat ctttatttac tttttccact tcatgttttt tttcctttag cttcgggcag   6480
tacatgaaca actggctgct ctgtcccagg gtccaatatc caagcccaag aggaaaagag   6540
agaaaaaaga gaaaagaag aaacggaagg cagagaagca tcgaggccga gctgggccg     6600 atgaagatga caagggggcct agggcacccc gcccacctca acctaagaag tccaagaaag   6660
caagtggcag tggggtggc agtgctgctt taggcccttc cggctttgga ccttctggag    6720
gaagtggcac caagtgagtt agagtaggaa gcagagacta gtttggctat ttctgtctct   6780 ctggggatg ccatctctct ttgcaaagat aattctaaat ggccagttaa cagatacaat    6840
aggctttgag cagtggtccc caacctttttt ggcaccaggg accagtttcg tggaacacag   6900
attttaccac agacagggtt tgaggggatg gttttttggga tgaaactgtt ccacctcaga  6960
tcattgggcc attggattcc cataaggagc atgcagcctg gatatgtacc atgcgcactt   7020
cacagtaggg ttcatgcttc tatgagaatc taatgcttct gctgatgtga caggcagtga   7080
```

```
tgcccacatg ccggctgttc acctcctgcg tagcccagta acaggccacg gactggtact    7140
ggtctggggg ttgggacccc tggctttggg agtcagggtg tttcacagct actctgacag    7200
tgaactcaaa gtagccataa actagaaaca tgaagatggt tgtgttccaa aaagacttta    7260
tttgcaaaga cacgtggcga tcagatttgt tctctgggcc atatagtttg cctgttgctc    7320
taaatcaatg agtctagact tgttttcat ggcgtagtag ttttgggttt tttggtgtgg    7380
ttttgtgttt ttttttgttt gtttttttttt tttttttttt tttttaaag actccaggct    7440 ggagtgcagt ggcgtgatct cggcttactg caacctccac ttctcgggtt caagcgattc    7500
tcctgcctca gcctcccaag tagccagaat tacaggcatg cgccaccacg cccagctaat    7560
ttttgtattt ttagtgcgca gctagtttat gtagttttag tggagacggg gtttcgccat    7620
gttgggcagg ctggtcttga actcctgacc tcaagtgatc tgcccgcctt ggcctcccaa    7680
agtgctggga ttacaaatct gagccactgc agctggccca tggtgtagtt tggtagtgtt    7740
taagggagca gaaagaccca tgtcagtata cctaaacagg tataccttgt tttattgtgc    7800
ttcactttac ggagttttt ttagatacta cttttttttt tagttgaaga tttgtgacaa    7860
ccctgtgtgg agcaagtctt tcaacagttt ttccaacatg tttgtgtgtc acattttag    7920 taatatttt tcattaaggt atgtacgtac attgtctttt taaagacatg ttattgccta    7980
cttacagtca agagcaaaat gctctgtttc actatacagt gtcccagtag cccacctctt    8040
acttggccat tgaatggaaa aacagaagct ccactctggg caggaaatag gatcactgaa    8100
ttataacagt gggaacatac tggaagaggt taatgaagct tcttttgctg caactctttt    8160
ttgcccttag gctccccaaa aaggccacaa agacagcccc acctgccctg cctacaggtt    8220
atgattcaga ggaggaggaa gagagcaggc ccatgagtta cgatgagaag cggcagctga    8280
gcctggacat caacaaatta cctggggaga agctgggccg agttgtgcat ataatccaag    8340
ccagggagcc ctctttacgt gattcaaacc cagaagagat tgagattgat tttgaaacac    8400
tcaagccatc cacacttaga gagcttgagc gctatgtcct ttcctgccta cgtaagaaac    8460
cccggaagcc ctacagtacg tatgaaatga ggttcatctc atggttctga ggacagttga    8520
ggaaagatgg tggggtctgt ttgcattcag gattgtcagc tcccaggata tgggatgtg    8580 ttggttggca gctgacgttc aagaagggaa cttgggaacc ttaggggccc ataataagat    8640
gcttggggca atcttaatgt atcctgataa atttctttca ttagccatta agaagcctgt    8700
gggaaagaca aaggaggaac tggctttgga gaaaaagcgg gaattagaaa agcggttaca    8760
agatgtcagc ggacagctca attctactaa aaagcccccc aagaaaggtg agtatatact    8820
ttcatgccac tacagattga ctccatcctg ccttcttgac tgtcttttat tgacaaatga    8880
agattcagac ttgaacgtct ttaactttcg aatttgttct gcagcgaatg agaaaacaga    8940
gtcatcctct gcacagcaag tagcagtgtc acgccttagc gcttccagct ccagctcaga    9000
ttccagctcc tcctcttcct cgtcgtcgtc ttcagacacc agtgattcag actcaggcta    9060
aggggtcagg ccagatgggg caggaaggct ccgcaggacc ggaccctag accaccctgc    9120 cccacctgcc ccttcccct ttgctgtgac acttcttcat ctcacccccc cctgccccc    9180 tctaggagag ctggctctgc agtgggggag ggatgcaggg acatttactg aaggaggac    9240 atggacaaaa caacattgaa ttcccagccc cattgggagt tgatctcttg gacacagagc    9300
ccccattcaa aatgggggcag ggcaagggtg ggagtgtgca aagccctgat ctggagttac    9360
ctgaggccat agctgcccta ttcacttcta agggccctgt tttgagattg tttgttctaa    9420
```

-continued

```
tttattttaa gctaggtaag gctgggggga gggtggggcc gtggtcccct cagcctccat   9480
ggggagggaa gaaggggag ctctttttt acgttgattt ttttttttct actctgtttt    9540
cccttttcc ttccgctcca tttgggggcc tggggttc agtcatctcc ccatttggtc    9600
ccctggactg tctttgttga ttctaacttg taaataaaga aaatattatt caagttttga   9660
gttaccttaa tatttgcttt tgtagtgttt caaaaggaac atcataagaa ttgtcttgat   9720
aattttgagg gaaatattac tgcagtgaga aaggcaata gctaacctat aattggattg    9780
tcttaatttt taaaccagta ggcttttgct gtgtttttaa taaagtaaat atgacttttg   9840
taaattgagt ccttagaagt aatctttagg tctacaattt gctcttgttt aaatgaaaaa   9900
tagtactgtg gctcattcat gctttaacca agaactcaaa attttgaggt aggctttagg   9960
tttttccctg tggcactgga tgtgtgaatt ttctcctgag cagacttaaa atatgagaaa  10020
agggtgggag gtagccgaac ataagtactt tatgcattga gtttattgcc ttttaaaagg  10080
aaattggcct gtaatcccag cactttggga ggccgaggcg ggcagatcac gaggtcagga  10140
gatcgagacc atggtgaaac cctgtctact aaaaaaaaat tagctgggcg aggtggcggg  10200
tacctgtagt cccagctact cgggaggctg aggcagcaga atggcgtgaa ctcgggaggc  10260
ggggttcagt gagccgagat cgcgccactg cactccagcc tgggtggtag acactccgtc  10320
tcaaaaaaaa aagtaattgg gcctactaca ttgttaaaca ttgttaaatt ttgctgccat  10380
ggtcacacac aaatttacag atagtttatt agtagaatac taaagagtat tccaacgatt  10440
aaatcacaaa actgtgcttt ctgcataccc ccttgtcttg ctaaggggag agaagggttg  10500
tataaaaagt ttaggggtt gggatgtttg cattctggaa tttggggctt taatactgga  10560
aaagtgagac atttgcttag tatagtgtac catagtagga aacctggata gagacatgga  10620
aattagaatc aggaatgtag taaagcaaat ggtttatttt gctgtaaatg acaccacaaa  10680
ctaagtgtag ggcaacacca caaactaaat gtaggaagca ataaattta ctagtgatgc  10740
tcagccctct ttaggaattc cggctaaact ggggcttgag caacaatttt caaaagctcg  10800
ggagatggta ataaaaatt aggtttgtga accacctgct actgtttgcc aagcacttag  10860
agggaaacaa acccttgttt gggctttctt gctaacttgt gtgcaccagt gaaagctctt  10920
gagctcctt tgagctctgg ttcccttttg agaataacag atgttgagga ttcgtaagta  10980
cttaatagag acgcgttggg caataggtga tgagatacaa attaaagttc tgaaaatcgg  11040
agtaaataga tttaagctaa gtgcatgtct atgtcaagga ttacatctca tttcagaggg  11100
aattgaagga tttagttgga ttagttttgg gacaaaatat agaatatttt gactgcagcc  11160
ccttctgctc atgtactttt aaggtttgtt ttctgtagtt cggaaaaata aaagtttcaa  11220
cctgacattg gaggcccctg agtacttaat tccctgtaaa tggaacccag accgccctaa  11280
atgctttaag agagagaagg gctggctgac acagggctt cagacctgcc ttaaaccaat  11340
tggactagtc tcttaattga ctttagtttg aacttatttc aagcctgtct cacttaggga  11400
ttgtaattgt ttcaggagtt tggttgagtt ccatcttggt tgccaaagga ctttattcca  11460
aaatagcagt ctccagcaca actcaaagga ctagtggagt cctgtgggca ttatttcccc  11520
ctatgctcct ctcagctctt ggaatcatgg gttctattgc tgctgctttt tccctctccc  11580
ctcatgctgc catttactgc cttttattgc gtccatagga agccttttgt tgggttgtgg  11640
gggaaggtga gagtcggtct tatttactca gtcacacatt tattgagttc ccttgattgc  11700
cttttcagca aactgttagg cctgtagacc tggacgttgc caagccagag ggtataaggt  11760
gaagataaga caaggtctta tcatggagtt tgcttagcac gaatagggtg caattattaa  11820
```

```
ccatcatggt gtggtaatta tactgattga atccaagata taggcatgac ttggtcttca   11880
cagaccatcc ttattgtgca cccatatgtg accccagtt ccagcctgcc tgtaaccttc   11940
cccaaagtcc tgctcttagg ttcactcggg actaccttga ttggaaggcc ctgcttccat   12000
gagtgaccag catgaaggac tcccaggaca aggaccagag gtgactggtg ttactctggg   12060
gcttagtgca agactggagg aagattttcc tgagcaatta gagagtggct gtaatggaga   12120
gctgggaagg agatgtggga atggtagcat ggaactaatg tgttgtcacc atgatttcat   12180
tttttcctgg gtcatcaccc taaagatact cacaaaatcc cactagctgg tctccagcac   12240
tgaatgagac gacagcttct tgctctcaat ttatattcta ggatcgggga aggggcagc    12300 attagacaac tagtcacacg atttttaaca aaaataagta attctaacag acaatgtgc    12360 agaggtctag caagaattta gaaaagaggg ttctctggtc taagctgaga gctattcaga   12420
tatctcagaa cgatgagttc cttcctgttt gtaaggggtg gatgggtggg agcagggagt   12480
agtgaacatt gccagcagaa gaaacagcaa ctgagaaggt aactaggtga tgctgaagca   12540
gcaaggatga aggtgagtgc tttgagatgc tttgaattta catctcaaag actaatagct   12600
aacatttatt gagcacttac tgtgtcccat gcactgtgct aaataaaaac ttaccctgta   12660
aactcatttg gtcctcacta taatcctgtg aggtacatct tgtctgcatt taacagataa   12720
agaaatgagg cacagagaga ttagtcaatt tgcccaacat caccacattg tcagtgagca   12780
ctggaggtgg gttttgaaac caggcgatct ggcttcaggg tccacattta taactactgc   12840
actagacttc cagtgctgtg ggccagtagg gagctaggag atagacatgc tttaaggaaa   12900
ttgcactagg gacaatcatg ttaggggttgg tggggtgttg agagtggata gtttagaaag   12960
caattgcagc agttaatccc agccagtgag aatagtggtg tagaagagaa aggcagcaat   13020
gtagatgaag aaatgtagat agatttgaga gctatgtagg agttaaaata gatgggactt   13080
attctcaaaa ggttcttgtc tccacacatt aaaggaacag cagagcacac gtgcacttgc   13140
agacatacag ctctcagagt ccctagcaca gagctttcca atagtggaag cttgatattt   13200
tgttgactaa aggagtgcca cctggctgac tggcagattt gaatggagct ccctccagca   13260
tggcttgcca aaggggcagg ggttctgagg ctcttgtaga ctgccactga aggtatttgg   13320
cgccacctgt tgggcgtgtt acccacgatt gcctcctgaa tctattgtca ttttgtgtc    13380 ctgccccga ggttaggtgg ttcttcccttt cttactttcc taaacttcaa ctcttaaaat   13440
gtgagccttc attttttatga cccagagggt cacaaaagaa ggagattagg cctttttagt   13500
ccttatctcc ctttacctct gaagcatccc atgggcttc cctagcattt tattttatat    13560
tgatttattt atttatttt aagaaagagg atttctgtca cccaggctgg agtgcagtgg    13620
tgtgatcata gctcactgta gcttcgacct tctgggctca agtaatgctc ttgcctcagc   13680
ctcctgagta gctgggatta caggcatgag ccaccgcacc ctgcatctcc tgacttcttt   13740
gacttgacac cacttgttcc tagctctcat acttttcaga cagccatttc ttagtctgct   13800
tctttaaagt ctctgcctct gcctcccata atatattgtc ccttatgaca cctttctttg   13860
tcctcttttt atttgcacag tatttttaag caagtttacc cattcctctg gaggcacctc   13920
ccacccataa aatctgtgtc tctgtttaga ccttgtatta gtccattctc acatggctat   13980
gaggaaatac ctgagactag gtgatttata aaggaaagag gtttaattga ctcacagttc   14040
tgcatggctg gggaggcctc aggaaactta caatcatggc ggaagacacc tcttcacagg   14100
gtggcaggag aatgagtgcc aaagtgaagt ggggaagccc cttataaaac cataagatct   14160
```

-continued

| | |
|---|---|
| cgtgagaact cactatcacg agaacagcat gggggaaact gccccatat caaaccttga | 14220 |
| gtcaaagttc caagtgccta atgcaatgcc taatggcaag gtcccataag ctcgtgcaca | 14280 |
| cattttaga aaagattcta ccttttccc caaacatgtc cctcgcagtg agttctctaa | 14340 |
| gtcagcagtc cccagctttt ttggcaccaa ggactggttt tgtggaagac aacttttcta | 14400 |
| tggatggagg cggggagaat ggtttccaga tcaaactgtt ctacttcaga tcaccaggca | 14460 |
| ttagattctc aaaaggagtt tgcaaccttc cctcgcatgc tcagttcaca atagggtttg | 14520 |
| cagtcctgtg agaatctaat gccgctgctg atcccgtcga c | 14561 |

<210> SEQ ID NO 2
<211> LENGTH: 3028
<212> TYPE: DNA
<213> ORGANISM: Homo sapiens

<400> SEQUENCE: 2

| | |
|---|---|
| gacggccgcc ggagccgcga ggccaactgt cgcctggttg ggcccggaaa tgggacgtcg | 60 |
| cgctttctca gggagcgtag aagcagccag ggcctctcca agccgctgct gtgacagaaa | 120 |
| gtgagtgagc tgccggagga tgtccaccgc cacgacagtc gccccgcgg ggatcccggc | 180 |
| gaccccgggc cctgtgaacc cacccccccc ggaggtctcc aacccagca agcccggccg | 240 |
| caagaccaac cagctgcagt acatgcagaa tgtggtggtg aagacgctct ggaaacacca | 300 |
| gttcgcctgg cccttctacc agcccgtgga cgcaatcaaa ttgaacctgc cggattatca | 360 |
| taaaataatt aaaaacccaa tggatatggg gactattaag aagagactag aaaataatta | 420 |
| ttattggagt gcaagcgaat gtatgcagga cttcaacacc atgtttacaa attgttacat | 480 |
| ttataacaag cccacagatg acatagtgct aatggcccaa gctttagaga aaattttct | 540 |
| acaaaaagtg gcccagatgc cccaagagga agttgaatta ttacccctg ctccaaaggg | 600 |
| caaggtcgg aagccggctg cgggagccca gagcgcaggt acacagcaag tggcggccgt | 660 |
| gtcctctgtc tccccagcga cccccttca gagcgtgccc ccaccgtct cccagacgcc | 720 |
| cgtcatcgct gccaccctg taccaaccat cactgcaaac gtcacgtcgg tcccagtccc | 780 |
| cccagctgcc gccccacctc ctcctgccac accatcgtc ccgtggtcc ctcctacgcc | 840 |
| gcctgtcgtc aagaaaaagg gcgtgaagcg gaaagcagac acaaccactc ccacgacgtc | 900 |
| ggccatcact gccagccgga gtgagtcgcc cccgccgttg tcagacccca gcaggccaa | 960 |
| agtggtggcc cggcgggaga gtggtggccg cccccatcaag cctcccaaga aggacctgga | 1020 |
| ggacggcgag gtgccccagc acgcaggcaa gaagggcaag ctgtcggagc acctgcgcta | 1080 |
| ctgcgacagc atcctcaggg agatgctatc caagaagcac gcggcctacg cctgccctt | 1140 |
| ctacaagcca gtggatgccg aggccctgga gctgcacgac taccacgaca tcatcaagca | 1200 |
| cccgatggac ctcagcaccg tgaaaaggaa gatggatggc cgagagtacc agacgcaca | 1260 |
| gggctttgct gctgatgtcc ggctgatgtt ctcgaattgc tacaaataca tcccccaga | 1320 |
| ccacgaggtt gtgccatgg cccggaagct ccaggacgtg tttgagatga ggtttgccaa | 1380 |
| gatgccagat gagcccgtgg aggcaccggc gctgcctgcc ccgcggccc ccatggtgag | 1440 |
| caagggcgct gagagcagcc gtagcagtga ggagagctct tcggactcag gcagctcgga | 1500 |
| ctcggaggag gagcgggcca ccaggctggc ggagctgcag gagcagctga aggccgtgca | 1560 |
| cgagcagctg gccgccctgt ctcaggcccc agtaaacaaa ccaaagaaga gaaggagaa | 1620 |
| gaaggagaag gagaagaaga gaaggacaa ggagaaggag aaggagaagc acaaagtgaa | 1680 |
| ggccgaggaa gagaagaagg ccaaggtggc tccgcctgcc aagcaggctc agcagaagaa | 1740 |

-continued

| | | |
|---|---|---|
| ggctcctgcc aagaaggcca acagcacgac cacggccggc agacagctga agaaaggcgg | 1800 |
| caagcaggca tctgcctcct acgactcaga ggaagaggag gagggcctgc ccatgagcta | 1860 |
| cgatgaaaag cgccagctta gcctggacat caaccggctg cccggggaga agctgggccg | 1920 |
| ggtagtgcac atcatccaat ctcgggagcc ctcgctcagg gactccaacc ccgacgagat | 1980 |
| agaaattgac tttgagactc tgaaacccac cactttgcgg gaactggaga gatatgtcaa | 2040 |
| gtcttgttta cagaaaaagc aaaggaaacc gttctcagca agcgggaaga aacaggcagc | 2100 |
| caagtcgaaa gaggagctag ctcaggaaaa gaagaaggag ctggaaaagc gtctgcagga | 2160 |
| tgtcagcggg cagctgagca gcagcaagaa gcccgcccgg aaagagaagc ccggctcagc | 2220 |
| accctcaggg ggcccgtcca ggctcagcag cagcagctcc tccgagtctg ggagcagcag | 2280 |
| ctccagcggg tccagctctg acagcagtga ctcagaatga actggcttcg acagaacag | 2340 |
| gacagatgga tgtcgcacac gccgagactc tgccgtaccc ctctgtggtt catattacta | 2400 |
| cttctgttcc atggtgtgca ggtctgcttc ttaattcagt gttatgatat cttccagttt | 2460 |
| ttgctttcat aggtcagaga tctatcttgt gtgtgcgtta gacttgatga aaggtgtga | 2520 |
| actctgcaga aagtctcttc ttcatcactg aattcagtca cttggagatg acaacttcaa | 2580 |
| atgctaaccc gatgacccca gaaaaccgtg tgagattcgt accgaagaac cttgtggaat | 2640 |
| ccctttgctt aggcccaacc tggtcgatag ctcgagaaag aattttttcc aaggaaatgt | 2700 |
| ctcggatatg ggtactgtat ttgaaagctg ttagctttgt caacacgcat tgtccttgtc | 2760 |
| atttgggccc cgagctctga ccctcgtgtc tgacgcggcc acctctttct ggaggggctg | 2820 |
| aggacagatg tgcctgcttg tggagaccag gctgggccta agcgaagggt catcgcagcc | 2880 |
| ccagcccgga gcgtggagcc cttgggggt ggtcgggtgg gatgtgcgtt ctccgctcgt | 2940 |
| ggtgatgtca ggagctcctc ggagggaaca gagcggctgt gtatgcagcc tgcaggtttc | 3000 |
| catacactga agctttttacc tcaactttt | 3028 |

<210> SEQ ID NO 3
<211> LENGTH: 3149
<212> TYPE: DNA
<213> ORGANISM: Homo sapiens

<400> SEQUENCE: 3

| | | |
|---|---|---|
| attctttgga atactactgc tagaagtctg acttaagacc cagcttatgg gccacatggc | 60 |
| acccagctgc ttctgcagag aaggcaggcc actgatgggt acagcaaagt gtggtgctgc | 120 |
| tggccaagcc aaagacccgt gtaggatgac tgggcctctg cccttgtgg gtgttgccac | 180 |
| tgtgcttgag tgcctggtga agaatgtgat gggatcacta gcatgtctgc ggagagcggc | 240 |
| cctgggacga gattgagaaa tctgccagta atgggggatg gactagaaac ttcccaaatg | 300 |
| tctacaacac aggcccaggc caacccag ccagccaacg cagccagcac caaccccccg | 360 |
| cccccagaga cctccaaccc taacaagccc aagaggcaga ccaaccaact gcaatacctg | 420 |
| ctcagagtgg tgctcaagac actatggaaa caccagtttg catggccttt ccagcagcct | 480 |
| gtggatgccg tcaagctgaa cctccctgat tactataaga tcattaaaac gcctatggat | 540 |
| atggaacaa taagaagcg cttggaaaac aactattact ggaatgctca ggaatgtatc | 600 |
| caggacttca acactatgtt tacaaattgt tacatctaca acaagcctgg agatgacata | 660 |
| gtcttaatgg cagaagctct ggaaaagctc ttcttgcaaa aaataaatga gctacccaca | 720 |
| gaagaaaccg agatcatgat agtccaggca aaaggaagag gacgtgggag gaaagaaaca | 780 |

-continued

```
gggacagcaa aacctggcgt ttccacggta ccaaacacaa ctcaagcatc gactcctccg    840
cagacccaga cccctcagcc gaatcctcct cctgtgcagg ccacgcctca cccctccct     900 gccgtcaccc cggacctcat cgtccagacc cctgtcatga cagtggtgcc tccccagcca    960
ctgcagacgc cccgccagt gccccccag ccacaacccc cacccgctcc agctccccag     1020
cccgtacaga gccacccacc catcatcgcg gccaccccac agcctgtgaa gacaaagaag    1080
ggagtgaaga ggaaagcaga caccaccacc cccaccacca ttgaccccat tcacgagcca    1140
ccctcgctgc ccccggagcc caagaccacc aagctgggcc agcggcggga gagcagccgg    1200
cctgtgaaac ctccaaagaa ggacgtgccc gactctcagc agcacccagc accagagaag    1260
agcagcaagg tctcggagca gctcaagtgc tgcagcggca tcctcaagga gatgtttgcc    1320
aagaagcacg ccgcctacgc ctggcccttc tacaagcctg tggacgtgga ggcactgggc    1380
ctacacgact actgtgacat catcaagcac cccatggaca tgagcacaat caagtctaaa    1440
ctggaggccc gtgagtaccg tgatgctcag gagtttggtg ctgacgtccg attgatgttc    1500
tccaactgct ataagtacaa ccctcctgac catgaggtgg tggccatggc ccgcaagctc    1560
caggatgtgt tcgaaatgcg ctttgccaag atgccggacg agcctgagga gccagtggtg    1620
gccgtgtcct ccccggcagt gcccctccc accaaggttg tggccccgcc ctcatccagc     1680
gacagcagca gcgatagctc ctcggacagt gacagttcga ctgatgactc tgaggaggag    1740
cgagcccagc ggctggctga gctccaggag cagctcaaag ccgtgcacga gcagcttgca    1800
gccctctctc agccccagca gaacaaacca agaaaaaagg agaaagacaa gaaggaaaag    1860
aaaaaagaaa agcacaaaag aaagaggaa gtggaagaga ataaaaaaag caaagccaag     1920
gaacctcctc ctaaaaagac gaagaaaaat aatagcagca acagcaatgt gagcaagaag    1980
gagccagcgc ccatgaagag caagccccct cccacgtatg agtcggagga agaggacaag    2040
tgcaagccta tgtcctatga ggagaagcgg cagctcagct tggacatcaa caagctcccc    2100
ggcgagaagc tgggccgcgt ggtgcacatc atccagtcac gggagccctc cctgaagaat    2160
tccaaccccg acgagattga aatcgacttt gagaccctga agccgtccac actgcgtgag    2220
ctggagcgct atgtcacctc ctgtttgcgg aagaaaagga aacctcaagc tgagaaagtt    2280
gatgtgattg ccggctcctc caagatgaag ggcttctcgt cctcagagtc ggagagctcc    2340
agtgagtcca gctcctctga cagcgaagac tccgaaacag gtcctgccta atcattggac    2400
acggactctt aataaaacgg tcttcagttc cagattcctt cccagcaagc tatagcttaa    2460
gtccattttc ttccgtgaaa gggacaggac tccatcaagt tatggaattc ctcagagccc    2520
tgggcctgtc ccccggggtg gattagtcat gtccagcagc acacgcctag tcccgccttc    2580
gggaaggctg cctgcctggc cagccgccca ggcctctctg tgtaaagact gcctggctgt    2640
cctgcccagc cttcctggtt ctctggggtc tctgggtgg gtggcatctc ctggagggtg     2700
atgacaatcc ccaacacatg cattcatgtg gtgctactct gtgtgcaaag ccagaccccca   2760 agtatgtttt ctctctttgt cccatccctc tttttctggg actttggacc ctaactactt    2820
ccctcctgaa ccttgcagtg acatcagtcc aggagagctc tcgttcagtg tgcggaagaa    2880
cactctgacc tctagagctg tcctagataa ggagtgggag cttagaggc aaggcctcta     2940 gaccctggaa ggctcagtga ggctcttccc acagcatgct tctcactggt gccctgtaag    3000
ctcgagccac cgctgactct gagcttttt ggagtctttc ctccttcgtc tccattgttc     3060
cgtgcatttc caaagcttaa gttgctggtg ggcatttccc cagtttctat gggctccgtc    3120
ttctcaagtc acatagggaa agtacccttc                                     3149
```

<210> SEQ ID NO 4
<211> LENGTH: 3106
<212> TYPE: DNA
<213> ORGANISM: Homo sapiens

<400> SEQUENCE: 4

```
gtggcaagat gttcctggga ggtcaagtta agagtcaaaa ataattcatt agatttaaca      60
atttagcatg gacatgtact tgtagacagg attcaaagca gttaagaatg tctctgccaa     120
gtcgacaaac agctattatt gttaaccctc ctccaccaga atatataaat actaagaaaa     180
atgggcgatt gacaaatcaa cttcagtatc tacaaaaagt tgtcctaaag gatttatgga     240
agcatagttt ttcatggccc tttcaacgtc ctgtggatgc tgtgaaacta agttgcctg      300
attattatac cattataaaa aacccaatgg atttaaatac aattaagaag cgcttggaga     360
ataaatatta tgcgaaggct tcagaatgta tagaagactt caatacaatg ttctcaaatt     420
gttatttata taacaagcct ggagatgaca ttgttcttat ggcacaagct ctagagaagc     480
tgtttatgca gaaattatct cagatgccac aagaagagca agttgtgggt gttaaggaaa     540
gaatcaagaa aggcactcaa cagaatatag ctgtttcttc tgctaaagaa aaatcatcac     600
ccagcgcaac agaaaaagta tttaagcagc aagaaattcc ttctgtattt cctaagacat     660
ctatttctcc cttgaacgtg gtacagggag cttcagtcaa ctccagttca caaactgcgg     720
cccaagttac aaaaggtgtg aagaggaaag cagatacaac aactcctgca acttcagcag     780
ttaaagcaag tagtgaattt tctccaacat tcacagaaaa atcagtggca ctgccaccta     840
taaaagaaaa tatgccaaag aatgtttttgc cagattctca gcaacaatat aatgttgtgg     900
agactgttaa agtaactgaa caattaaggc actgtagtga gattcttaaa gaaatgcttg     960
caaagaaaca tttttcatat gcatggccct tttataatcc tgttgacgtt aatgctttgg    1020
gactccataa ctactatgac gttgtcaaaa atccgatgga tcttggaact attaaggaga    1080
aaatggataa ccaagaatat aaggatgcat actcatttgc ggcagatgtt agattaatgt    1140
tcatgaattg ctacaagtac aatcctccag atcacgaagt tgtgacaatg caagaatgc    1200
ttcaggatgt tttcgaaacg catttttcaa agatcccgat tgaacctgtt gagagtatgc    1260
ctttatgtta catcaaaaca gatatcacag aaaccactgg tagagagaac actaatgaag    1320
cctcctctga agggaactct tctgatgatt ctgaagatga gcgagttaag cgtcttgcaa    1380
agcttcagga gcagcttaaa gctgtacatc aacagctcca ggttttgtcc caagtaccct    1440
tccgtaagct aaataaaaag aaagagaagt ctaaaaagga aaagaaaaaa gaaaggtta    1500
ataacagcaa tgaaaatcca agaaaatgt gtgagcaaat gaggctaaag gaaaagtcca    1560
agagaaatca gccaagagaaa aggaaacaac agttcattgg tctaaaatct gaagatgaag    1620
ataatgctaa acctatgaac tatgatgaga aaggcagtt aagtctgaat ataaacaaac    1680
tccctggaga taaacttggg cgagtagttc acataataca atcaagagag ccttctctga    1740
gcaattccaa tcctgatgag atagagatag actttgaaac actgaaagca tcaacactaa    1800
gagaattaga aaaatatgtt tcggcatgtc taagaaagag accattaaaa cctcctgcta    1860
agaaaataat gatgtccaaa gaagaacttc actcacagaa aaacaggaa ttggaaaagc    1920
ggttactgga tgttaataat cagttaaatt ctagaaaacg tcaaacaaaa tctgataaaa    1980
cgcaaccatc caaagctgtt gaaaatgttt cccgactgag tgagagcagc agcagcagca    2040
gcagctcatc agagtctgaa agtagcagca gtgacttaag ctcttcagac agcagtgatt    2100
```

-continued

```
ctgaatcaga aatgttccct aagtttacag aagtaaaacc aaatgattct ccttctaaag    2160
agcatgtaaa gaaatgaag aatgaatgca tactgcctga aggaagaaca ggcgtcacac     2220
agataggata ttgtgtgcaa gacacaacct ctgccaatac tacccttgtt catcagacca    2280
caccttcaca tgtaatgcca ccaaatcacc accaattagc atttaattat caagaattag    2340
aacatttaca gactgtgaaa acatttcac ctttacaaat tctgcctccc tcaggtgatt     2400
ctgaacagct ctcaaatggc ataactgtga tgcatccatc tggtgatagt gacacaacga    2460
tgttagaatc tgaatgtcaa gctcctgtac agaaggatat aaagattaag aatgcagatt    2520
catggaaaag tttaggcaaa ccagtgaaac catcaggtgt aatgaaatcc tcagatgagc    2580
tcttcaacca atttagaaaa gcagccatag aaaaggaagt aaaagctcgg acacaggaac    2640
tcatacggaa gcatttggaa caaaatacaa aggaactaaa agcatctcaa gaaaatcaga    2700
gggatcttgg gaatggattg actgtagaat cttttttcaaa taaatacaa aacaagtgct    2760 ctggagaaga gcagaaagaa catccgcagt catcagaagc tcaagataaa tccaaactct    2820
ggcttctcaa agaccgtgat ttagccaggc cgaaagaaca agagaggagg aggagagaag    2880
ccatggtggg taccattgat atgacccttc aaagtgacat tatgacaatg tttgaaaaca    2940
actttgatta aaactcagtt tttaaattaa ccatccactt aaaatgaatg gtaaaagatc    3000
aaaatgcata tggtaaaatg attgctttca gataacaaga taccaatctt atattgtatt    3060
ttgactgctc taaatgatt aaacagtttt cacttacaaa aaaaaa                     3106
```

<210> SEQ ID NO 5
<211> LENGTH: 20
<212> TYPE: DNA
<213> ORGANISM: Homo sapiens

<400> SEQUENCE: 5
tcaagaaagg cactcaacag                                                20

<210> SEQ ID NO 6
<211> LENGTH: 21
<212> TYPE: DNA
<213> ORGANISM: Homo sapiens

<400> SEQUENCE: 6
ttcactactt gctttaactg c                                              21

<210> SEQ ID NO 7
<211> LENGTH: 20
<212> TYPE: DNA
<213> ORGANISM: Homo sapiens

<400> SEQUENCE: 7
gggaagggaa tgcagggttg                                                20

<210> SEQ ID NO 8
<211> LENGTH: 21
<212> TYPE: DNA
<213> ORGANISM: Homo sapiens

<400> SEQUENCE: 8
tggctgttct tagggatggt c                                              21

<210> SEQ ID NO 9
<211> LENGTH: 20
<212> TYPE: DNA
<213> ORGANISM: Homo sapiens

<400> SEQUENCE: 9

```
taatggccca agctttagag                                                  20
```

<210> SEQ ID NO 10
<211> LENGTH: 21
<212> TYPE: DNA
<213> ORGANISM: Homo sapiens

<400> SEQUENCE: 10

```
gtttgcagtg atggttggta c                                                21
```

<210> SEQ ID NO 11
<211> LENGTH: 20
<212> TYPE: DNA
<213> ORGANISM: Homo sapiens

<400> SEQUENCE: 11

```
agcacccagc accagagaag                                                  20
```

<210> SEQ ID NO 12
<211> LENGTH: 20
<212> TYPE: DNA
<213> ORGANISM: Homo sapiens

<400> SEQUENCE: 12

```
tgctgctgtc gctggatgag                                                  20
```

<210> SEQ ID NO 13
<211> LENGTH: 3446
<212> TYPE: DNA
<213> ORGANISM: Homo sapiens

<400> SEQUENCE: 13

```
gcgcaggaac ttaagacagt tcctcctggc gatgtgatgg aatttaatgg gacaggagaa        60
gggaacgggc tttcttttca ggccagcgtg gcagcgggcg gtagggcgaa agggagaagg       120
aaacgagggt ttattccgtt gcccactccg cgatatttac aaccgtaaca gagaaaatgg       180
aaaagcaaaa gcccttttgca ttgttcgtac caccgagatc aagcagcagt caggtgtctg     240
cggtgaaacc tcagaccctg ggaggcgatt ccactttctt caagagtttc aacaaatgta       300
ctgaagatga ttttgagttt ccatttgcaa agactaatct ctccaaaaat ggggaaaaca       360
ttgattcaga tcctgcttta caaaaagtta atttcttgcc cgtgcttgag caggttggta       420
attctgactg tcactatcag gaaggactaa aagactctga tttggagaat tcagagggat       480
tgagcagagt gtattcaaaa ctgtataagg aggctgaaaa gataaaaaaa tggaaagtaa       540
gtacagaagc tgaactgaga cagaaagaaa gtaagttgca agaaaacaga aagataattg       600
aagcacagcg aaaagccatt caggaactgc aatgtgtgaaa tgaaaagta agtttgacat       660
tagaagaagg aatacaagac aataaagatt taataaaaga gaataatgcc acaaggcatt       720
tatgtaatct actcaaagaa acctgtgcta gatctgcaga aaagacaaag aaatatgaat       780
atgaacggga agaaaccagg caagtttata tggatctaaa tagtaacatt gagaaaatga       840
taacagcttt tgaggaactt cgtgtgcaag ctgagaattc cagactggaa atgcatttta       900
agttaaaggg agattatgaa aaaatccaac accttgaaca gaatacaag aaggaaataa        960
atgacaagga aaagcaggta tcactactat tgatccaaat cactgagaaa gaaaataaaa      1020
tgaaagattt aacatttctg ctagaggaat ccagagataa agttaatcaa ttagaggaaa      1080
```

```
agacaaaatt acagagtgaa aacttaaaac aatcaattga gaaacagcat catttgacta    1140
aagaactaga agatattaaa gtgtcattac aaagaagtgt gagtactcaa aaggctttag    1200
aggaagattt acagatagca acaaacacaa tttgtcagct aactgaagaa aaagacactc    1260
aaatggaaga atctaataaa gctagagctg ctcattcgtt tgtggttact gaatttgaaa    1320
ctactgtctg cagcttggaa gaattattga gaacagaaca gcaaagattg gaaaattatg    1380
aagatcaatt gataatactt accatggagc ttcaaaagac atcaagtgag ctggaagaga    1440
tgactaagct tacaaataac aaagaagtag aacttgaaga attgaaaaaa gtcttgggag    1500
aaaaggaaac acttttatat gacaataaac aatttgagaa gattgctgaa gaattaaaag    1560
gaacagaaca agaactaatt ggtcttctcc aagccagaga gaaagaagta catgatttgg    1620
aatacagtta ctgccattac cacaagtgga cagtattacc caaagaggt caaagaccaa    1680 aactgagctc gaaacgagaa ctcaagaata ctgaatactt cacactgcaa caagcttcac    1740
ccccccccaa cgagctcaca caggaaacaa gtgatatgac cctagaactc aagaatcagc    1800
aagaagatat aattaataac aaaaagcaag aagaaaggat gttgacacaa atagaaaatc    1860
ttcaagaaac agaaacccaa ttaagaaatg aactagaata tgtgagagaa gagctaaaac    1920
agaaaagaga tgaagttaaa tgtaaattgg acaagagtga agaaaattgt aacaatttaa    1980
ggaaacaagt tgaaaataaa aacaagtata ttgaagaact tcagcaggag aataaggcct    2040
tgaaaaaaaa aggtacagca gaaagcaagc aactgaatgt ttatgagata aaggtcaata    2100
aattagagtt agaactagaa agtgccaaac agaaatttgg agaaatcaca gacacctatc    2160
agaaagaaat tgaggacaaa aagatatcag aagaaatct tttggaagag gttgagaaag    2220
caaaagtaat agctgatgaa gcagtaaaat tacagaaaga aattgataag cgatgtcaac    2280
ataaaatagc tgaaatggta gcacttatgg aaaaacataa gcaccaatat gataagatca    2340
ttgaagaaag agactcagaa ttaggacttt ataagagcaa agaacaagaa cagtcatcac    2400
tgagagcatc tttggagatt gaactatcca atctcaaagc tgaactttg tctgttaaga    2460 agcaacttga aatagaaaga gaagagaagg aaaaactcaa aagagaggca aaagaaaaca    2520
cagctactct taaagaaaaa aaagacaaga aaacacaaac atttttattg gaaacacctg    2580
acatttattg gaaattggat tctaaagcag ttccttcaca aactgtatct cgaaatttca    2640
catcagttga tcatggcata tccaaagata aaagagacta tctgtggaca tctgccaaaa    2700
atactttatc tacaccattg ccaaaggcat atacagtgaa gacaccaaca aaaccaaaac    2760
tacagcaaag agaaaacttg aatatacccca ttgaagaaag taaaaaaaag agaaaaatgg    2820
cctttgaatt tgatattaat tcagatagtt cagaaactac tgatcttttg agcatggttt    2880
cagaagaaga gacattgaaa acactgtata ggaacaataa tccaccagct tctcatcttt    2940
gtgtcaaaac accaaaaaag gccccttcat ctctaacaac ccctggatct acactgaagt    3000
ttggagctat aagaaaaatg cgggaggacc gttgggctgt aattgctaaa atggatagaa    3060
aaaaaaaact aaaagaagct gaaaagttat ttgtttaatt tcagagaatc agtgtagtta    3120
aggagcctaa taacgtgaaa cttatagtta atattttgtt cttatttgcc agagccaaat    3180
tttatctgga agttgagact taaaaaatac ttgcatgaat gatttgtgtt tctttatatt    3240
tttagcctaa atgttaacta catattgtct ggaaacctgt cattgtattc agataaattag    3300 atgattatat attgttgtta ctttttcttg tattcatgaa aactgttttt actaagtttt    3360
caaatttgta aagttagcct ttgaatgcta agaatgcatt attgagggtc attctttatt    3420
ctttactatt aaaatatttt ggatgc                                        3446
```

<210> SEQ ID NO 14
<211> LENGTH: 752
<212> TYPE: DNA
<213> ORGANISM: Homo sapiens

<400> SEQUENCE: 14

```
atcctcgtgg gccctgacct tctctctgag agccgggcag aggctccgga gccatgcagg      60
ccgaaggccg gggcacaggg ggttcgacgg gcgatgctga tgcccagga ggccctggca     120
ttcctgatgg cccaggggc aatgctggcg gcccaggaga ggcgggtgcc acgggcggca     180
gaggtccccg gggcgcaggg gcagcaaggg cctcggggcc gggaggaggc gccccgcggg     240
gtccgcatgg cggcgcggct tcagggctga atggatgctg cagatgcggg gccaggggggc     300
cggagagccg cctgcttgag ttctacctcg ccatgccttt cgcgacaccc atggaagcag     360
agctggcccg caggagcctg gcccaggatg ccccaccgct tcccgtgcca gggtgcttc      420
tgaaggagtt cactgtgtcc ggcaacatac tgactatccg actgactgct gcagaccacc     480
gccaactgca gctctccatc agctcctgtc tccagcagct ttccctgttg atgtggatca     540
cgcagtgctt tctgcccgtg ttttggctc agcctccctc agggcagagg cgctaagccc     600
agcctggcgc cccttcctag gtcatgcctc ctccccctagg gaatggtccc agcacgagtg     660
gccagttcat tgtgggggcc tgattgtttg tcgctggagg aggacggctt acatgtttgt     720
ttctgtagaa aataaaactg agctacgaaa aa                                   752
```

<210> SEQ ID NO 15
<211> LENGTH: 4265
<212> TYPE: DNA
<213> ORGANISM: Homo sapiens

<400> SEQUENCE: 15

```
gtctgaagga cctgaggcat tttgtgacga ggatcgtctc aggtcagcgg agggaggaga      60
cttatagacc tatccagtct tcaaggtgct ccagaaagca ggagttgaag acctgggtgt     120
gagggacaca tacatcctaa aagcaccaca gcagaggagg cccaggcagt gccaggagtc     180
aaggttccca gaagacaaac cccctaggaa gacaggcgac ctgtgaggcc ctagagcacc     240
accttaagag aagaagagct gtaagccggc ctttgtcaga gccatcatgg gggacaagga     300
tatgcctact gctgggatgc cgagtcttct ccagagttcc tctgagagtc ctcagagttg     360
tcctgagggg gaggactccc agtctcctct ccagattccc cagagttctc ctgagagcga     420
cgacaccctg tatcctctcc agagtcctca gagtcgttct gagggggagg actcctcgga     480
tcctctccag agacctcctg agggaaagga ctcccagtct cctctccaga ttccccagag     540
ttctcctgag ggcgacgaca cccagtctcc tctccagaat tctcagagtt cctgaggg     600
gaaggactcc ctgtctcctc tagagatttc tcagagccct cctgagggtg aggatgtcca     660
gtctcctctg cagaatcctg cgagttcctt cttctcctct gctttattga gtattttcca     720
gagttcccct gagagtattc aaagtccttt tgagggtttt cccagtctg ttctccagat     780
tcctgtgagc gccgcctcct cctccacttt agtgagtatt ttccagagtt cccctgagag     840
tactcaaagt ccttttgagg gttttcccca gtctccactc cagattcctg tgagccgctc     900
cttctcctcc actttattga gtattttcca gagttcccct gagagaagtc agagaacttc     960
tgagggtttt gcacagtctc ctctccagat tcctgtgagc tcctcctcgt cctccacttt    1020
actgagtctt ttccagagtt cccctgagag aactcagagt acttttgagg gttttccca     1080
```

-continued

| | |
|---|---|
| gtctccactc cagattcctg tgagccgctc cttctcctcc actttattga gtattttcca | 1140 |
| gagttcccct gagagaactc agagtacttt tgagggtttt gcccagtctc ctctccagat | 1200 |
| tcctgtgagc ccctccttct cctccacttt agtgagtatt ttccagagtt ccctgagag | 1260 |
| aactcagagt acttttgagg gttttcccca gtctcctctc cagattcctg tgagctcctc | 1320 |
| cttctcctcc actttattga gtcttttcca gagttcccct gagagaactc agagtacttt | 1380 |
| tgagggtttt ccccagtctc ctctccagat tcctggaagc ccctccttct cctccacttt | 1440 |
| actgagtctt ttccagagtt ccctgagag aactcacagt acttttgagg gttttcccca | 1500 |
| gtctcctctc cagattccta tgacctcctc cttctcctct actttattga gtattttaca | 1560 |
| gagttctcct gagagtgctc aaagtgcttt tgagggtttt ccccagtctc ctctccagat | 1620 |
| tcctgtgagc tcctctttct cctacactt attgagtctt ttccagagtt ccctgagag | 1680 |
| aactcacagt acttttgagg gttttcccca gtctcctctc cagattcctg tgagctcctc | 1740 |
| ctcctcctcc tccactttat tgagtctttt ccagagttcc cctgagtgta ctcaaagtac | 1800 |
| ttttgagggt ttccccagt ctcctctcca gattcctcag agtcctcctg aagggagaa | 1860 |
| tacccattct cctctccaga ttgttccaag tcttcctgag tgggaggact ccctgtctcc | 1920 |
| tcactacttt cctcagagcc ctcctcaggg ggaggactcc ctatctcctc actactttcc | 1980 |
| tcagagccct cctcaggggg aggactccct gtctcctcac tactttcctc agagccctca | 2040 |
| gggggaggac tccctgtctc ctcactactt cctcagagc cctcctcagg gggaggactc | 2100 |
| catgtctcct ctctactttc ctcagagtcc tcttcagggg gaggaattcc agtcttctct | 2160 |
| ccagagccct gtgagcatct gctcctcctc cactccatcc agtcttcccc agagtttccc | 2220 |
| tgagagttct cagagtcctc ctgagggcc tgtccagtct cctctccata gtcctcagag | 2280 |
| ccctcctgag gggatgcact cccaatctcc tctccagagt cctgagagtg ctcctgaggg | 2340 |
| ggaggattcc ctgtctcctc tccaaattcc tcagagtcct cttgagggag aggactccct | 2400 |
| gtcttctctc cattttcctc agagtcctcc tgagtgggag gactccctct ctcctctcca | 2460 |
| cttttcctcag tttcctcctc aggggagga cttccagtct tctctccaga gtcctgtgag | 2520 |
| tatctgctcc tcctccactt ctttgagtct tccccagagt ttccctgaga gtcctcagag | 2580 |
| tcctcctgag gggcctgctc agtctcctct ccagagacct gtcagctcct tcttctccta | 2640 |
| cactttagcg agtcttctcc aaagttccca tgagagtcct cagagtcctc ctgaggggcc | 2700 |
| tgcccagtct cctctccaga gtcctgtgag ctccttcccc tcctccactt catcgagtct | 2760 |
| ttcccagagt tctcctgtga gctccttccc ctcctccact tcatcgagtc tttccaagag | 2820 |
| ttcccctgag agtcctctcc agagtcctgt gatctccttc tcctcctcca cttcattgag | 2880 |
| cccattcagt gaagagtcca gcagcccagt agatgaatat acaagttcct cagacacctt | 2940 |
| gctagagagt gattccttga cagacagcga gtccttgata gagagcgagc ccttgttcac | 3000 |
| ttatacactg gatgaaaagg tggacgagtt ggcgcggttt cttctcctca aatatcaagt | 3060 |
| gaagcagcct atcacaaagg cagagatgct gacgaatgtc atcagcaggt acacgggcta | 3120 |
| cttttcctgtg atcttcagga aagcccgtga gttcatagag atactttttg gcatttccct | 3180 |
| gagagaagtg gaccctgatg actccctatgt ctttgtaaac acattagacc tcacctctga | 3240 |
| ggggtgtctg agtgatgagc agggcatgtc ccagaaccgc ctcctgattc ttattctgag | 3300 |
| tatcatcttc ataaagggca cctatgcctc tgaggaggtc atctgggatg tgctgagtgg | 3360 |
| aataggggtg cgtgctggga gggagcactt tgcctttggg gagcccaggg agctcctcac | 3420 |
| taaagtttgg gtgcaggaac attacctaga gtaccgggag gtgcccaact cttctcctcc | 3480 |

-continued

```
tcgttacgaa ttcctgtggg gtccaagagc tcattcagaa gtcattaaga ggaaagtagt    3540 agagttttg gccatgctaa agaataccgt ccctattacc tttccatcct cttacaagga    3600
tgctttgaaa gatgtggaag agagagccca ggccataatt gacaccacag atgattcgac    3660
tgccacagaa agtgcaagct ccagtgtcat gtcccccagc ttctcttctg agtgaagtct    3720
agggcagatt cttccctctg agtttgaagg gggcagtcga gtttctacgt ggtggagggc    3780
ctggttgagg ctggagagaa cacagtgcta tttgcatttc tgttccatat gggtagttat    3840
ggggtttacc tgttttactt ttgggtattt ttcaaatgct tttcctatta ataacaggtt    3900
taaatagctt cagaatccta gtttatgcac atgagtcgca catgtattgc tgttttcctg    3960
gtttaagagt aacagtttga tattttgtaa aaacaaaaac acacccaaac acaccacatt    4020
gggaaaacct tctgcctcat tttgtgatgt gtcacaggtt aatgtggtgt tactgtagga    4080
attttcttga aactgtgaag gaactctgca gttaaatagt ggaataaagt aaaggattgt    4140
taatgtttgc atttcctcag gtcctttagt ctgttgttct tgaaaactaa agatacatac    4200
ctggtttgct tggcttacgt aagaaagtcg aagaaagtaa actgtaataa ataaaagtgt    4260
cagtg                                                                4265
```

<210> SEQ ID NO 16
<211> LENGTH: 766
<212> TYPE: DNA
<213> ORGANISM: Homo sapiens

<400> SEQUENCE: 16

```
ctctctttcg attcttccat actcagagta cgcacggtct gattttctct ttggattctt     60
ccaaaatcag agtcagactg ctcccggtgc catgaacgga gacgacgcct tgcaaggag    120 acccacggtt ggtgctcaaa taccagagaa gatccaaaag gccttcgatg atattgccaa    180
atacttctct aaggaagagt gggaaaagat gaaagcctcg agaaaatct tctatgtgta    240 tatgaagaga agtatgagg ctatgactaa actaggtttc aaggccaccc tcccacctt    300 catgtgtaat aaacgggccg aagacttcca ggggaatgat ttggataatg accctaaccg    360
tgggaatcag gttgaacgtc ctcagatgac tttcggcagg ctccagggaa tctccccgaa    420
gatcatgccc aagaagccag cagaggaagg aaatgattcg gaggaagtgc cagaagcatc    480
tggcccacaa aatgatggga agagctgtg cccccggga aaaccaacta cctctgagaa    540
gattcacgag agatctggac ccaaaagggg ggaacatgcc tggacccaca gactgcgtga    600
gagaaaacag ctggtgattt atgaagagat cagcgaccct gaggaagatg acgagtaact    660
cccctcaggg atacgacaca tgcccatgat gagaagcaga acgtggtgac ctttcacgaa    720
catgggcatg gctgcggacc cctcgtcatc aggtgcatag caagtg                   766
```

<210> SEQ ID NO 17
<211> LENGTH: 576
<212> TYPE: DNA
<213> ORGANISM: Homo sapiens

<400> SEQUENCE: 17

```
atgaacggag acgacgcctt tgcaaggaga cccagggatg atgctcaaat atcagagaag     60
ttacgaaagg ccttcgatga tattgccaaa tacttctcta agaaagagtg ggaaaagatg    120
aaatcctcgg agaaaatcgt ctatgtgtat atgaagctaa actatgaggt catgactaaa    180
ctaggtttca aggtcaccct cccaccttc atgcgtagta acgggctgc agacttccac    240
```

```
gggaatgatt ttggtaacga tcgaaaccac aggaatcagg ttgaacgtcc tcagatgact        300
ttcggcagcc tccagagaat cttcccgaag atcatgccca agaagccagc agaggaagaa        360
aatggtttga aggaagtgcc agaggcatct ggcccacaaa atgatgggaa acagctgtgc        420
cccccgggaa atccaagtac cttggagaag attaacaaga catctggacc caaaaggggg        480
aaacatgcct ggacccacag actgcgtgag agaaagcagc tggtggttta tgaagagatc        540
agcgaccctg aggaagatga cgagtaactc ccctcg                                   576

<210> SEQ ID NO 18
<211> LENGTH: 1624
<212> TYPE: DNA
<213> ORGANISM: Homo sapiens

<400> SEQUENCE: 18
gttttcaggg gacaggccaa cccagaggac aggattccct ggaggccaca gaggagcacc         60
aaggagaaga tctgcctgtg ggtcttcatt gcccagctcc tgcccacact cctgcctgct        120
gccctgacga gagtcatcat gtctcttgag cagaggagtc tgcactgcaa gcctgaggaa        180
gcccttgagg cccaacaaga ggccctgggc ctggtgtgtg tgcaggctgc cacctcctcc        240
tcctctcctc tggtcctggg caccctggag gaggtgccca ctgctgggtc aacagatcct        300
ccccagagtc ctcaggagc ctccgccttt cccactacca tcaacttcac tcgacagagg        360
caacccagtg agggttccag cagccgtgaa gaggagggc caagcacctc ttgtatcctg        420
gagtccttgt tccgagcagt aatcactaag aaggtggctg atttggttgg ttttctgctc        480
ctcaaatatc gagccaggga gccagtcaca aaggcagaaa tgctggagag tgtcatcaaa        540
aattacaagc actgttttcc tgagatcttc ggcaaagcct ctgagtcctt gcagctggtc        600
tttggcattg acgtgaagga agcagacccc accggccact cctatgtcct tgtcacctgc        660
ctaggtctct cctatgatgg cctgctgggt gataatcaga tcatgcccaa gacaggcttc        720
ctgataattg tcctggtcat gattgcaatg gagggcggcc atgctcctga ggaggaaatc        780
tgggaggagc tgagtgtgat ggaggtgtat gatgggaggg agcacagtgc ctatggggag        840
cccaggaagc tgctcaccca agatttggtg caggaaaagt acctggagta ccggcaggtg        900
ccggacagtg atcccgcacg ctatgagttc ctgtggggtc aagggccct cgctgaaacc        960 agctatgtga aagtccttga gtatgtgatc aaggtcagtg caagagttcg cttttttcttc       1020 ccatccctgc gtgaagcagc tttgagagag gaggaagagg gagtctgagc atgagttgca       1080
gccaaggcca gtgggagggg gactgggcca gtgcaccttc agggccgcg tccagcagct        1140 tccctgcct cgtgtgacat gaggcccatt cttcactctg aagagagcgg tcagtgttct       1200
cagtagtagg tttctgttct attgggtgac ttggagattt atctttgttc tcttttggaa      1260
ttgttcaaat gttttttttt aagggatggt tgaatgaact tcagcatcca agtttatgaa      1320
tgacagcagt cacacagttc tgtgtatata gtttaagggt aagagtcttg tgttttattc      1380
agattgggaa atccattcta ttttgtgaat tgggataata acagcagtgg aataagtact      1440
tagaaatgtg aaaaatgagc agtaaaatag atgagataaa gaactaaaga aattaagaga      1500
tagtcaattc ttgccttata cctcagtcta ttctgtaaaa ttttttaaaga tatatgcata     1560 cctggatttc cttggcttct ttgagaatgt aagagaaatt aaatctgaat aaagaattct      1620
tcct                                                                    1624

<210> SEQ ID NO 19
<211> LENGTH: 945
```

-continued

```
<212> TYPE: DNA
<213> ORGANISM: Homo sapiens

<400> SEQUENCE: 19
atgcctcttg agcagaggag tcagcactgc aagcctgaag aaggccttga ggcccgagga      60
gaggccctgg gcctggtggg tgcgcaggct cctgctactg aggagcagga ggctgcctcc     120
tcctcttcta ctctagttga agtcaccctg ggggaggtgc ctgctgccga gtcaccagat     180
cctccccaga gtcctcaggg agcctccagc ctccccacta ccatgaacta ccctctctgg     240
agccaatcct atgaggactc cagcaaccaa gaagaggagg ggccaagcac cttccctgac     300
ctggagtccg agttccaagc agcactcagt aggaaggtgg ccgagttggt tcattttctg     360
ctcctcaagt atcgagccag ggagccggtc acaaaggcag aaatgctggg gagtgtcgtc     420
ggaaattggc agtatttctt tcctgtgatc ttcagcaaag cttccagttc cttgcagctg     480
gtctttggca tcgagctgat ggaagtggac cccatcggcc acttgtacat ctttgccacc     540
tgcctgggcc tctcctacga tggcctgctg ggtgacaatc agatcatgcc caaggcaggc     600
ctcctgataa tcgtcctggc cataatcgca agagagggcg actgtgcccc tgaggagaaa     660
atctgggagg agctgagtgt gttagaggtg tttgagggga gggaagacag tatcttgggg     720
gatcccaaga agctgctcac ccaacatttc gtgcaggaaa actacctgga gtaccggcag     780
gtccccggca gtgatcctgc atgttatgaa ttcctgtggg gtccaagggc cctcgttgaa     840
accagctatg tgaaagtcct gcaccatatg gtaaagatca gtggaggacc tcacatttcc     900
tacccacccc tgcatgagtg ggttttgaga gaggggggaag agtga                    945

<210> SEQ ID NO 20
<211> LENGTH: 754
<212> TYPE: PRT
<213> ORGANISM: Homo sapiens

<400> SEQUENCE: 20
```

Met Ala Ser Val Pro Ala Leu Gln Leu Thr Pro Ala Asn Pro Pro Pro
1               5                   10                  15

Pro Glu Val Ser Asn Pro Lys Lys Pro Gly Arg Val Thr Asn Gln Leu
            20                  25                  30

Gln Tyr Leu His Lys Val Val Met Lys Ala Leu Trp Lys His Gln Phe
        35                  40                  45

Ala Trp Pro Phe Arg Gln Pro Val Asp Ala Val Lys Leu Gly Leu Pro
    50                  55                  60

Asp Tyr His Lys Ile Ile Lys Gln Pro Met Asp Met Gly Thr Ile Lys
65                  70                  75                  80

Arg Arg Leu Glu Asn Asn Tyr Tyr Trp Ala Ala Ser Glu Cys Met Gln
                85                  90                  95

Asp Phe Asn Thr Met Phe Thr Asn Cys Tyr Ile Tyr Asn Lys Pro Thr
            100                 105                 110

Asp Asp Ile Val Leu Met Ala Gln Thr Leu Glu Lys Ile Phe Leu Gln
        115                 120                 125

Lys Val Ala Ser Met Pro Gln Glu Glu Gln Glu Leu Val Val Thr Ile
    130                 135                 140

Pro Lys Asn Ser His Lys Lys Gly Ala Lys Leu Ala Ala Leu Gln Gly
145                 150                 155                 160

Ser Val Thr Ser Ala His Gln Val Pro Ala Val Ser Ser Val Ser His
                165                 170                 175

Thr Ala Leu Tyr Thr Pro Pro Pro Glu Ile Pro Thr Thr Val Phe Asn

-continued

```
                180             185             190
Ile Pro His Pro Ser Val Ile Ser Ser Pro Leu Leu Lys Ser Leu His
            195             200             205
Ser Ala Gly Pro Pro Leu Leu Ala Val Thr Ala Ala Pro Pro Ala Gln
            210             215             220
Pro Leu Ala Lys Lys Lys Gly Val Lys Arg Lys Ala Asp Thr Thr Thr
225             230             235             240
Pro Thr Pro Thr Ala Ile Leu Ala Pro Gly Ser Pro Ala Ser Pro Pro
                245             250             255
Gly Ser Leu Glu Pro Lys Ala Ala Arg Leu Pro Pro Met Arg Arg Glu
            260             265             270
Ser Gly Arg Pro Ile Lys Pro Arg Lys Asp Leu Pro Asp Ser Gln
            275             280             285
Gln Gln His Gln Ser Ser Lys Lys Gly Lys Leu Ser Glu Gln Leu Lys
        290             295             300
His Cys Asn Gly Ile Leu Lys Glu Leu Leu Ser Lys Lys His Ala Ala
305             310             315             320
Tyr Ala Trp Pro Phe Tyr Lys Pro Val Asp Ala Ser Ala Leu Gly Leu
                325             330             335
His Asp Tyr His Asp Ile Ile Lys His Pro Met Asp Leu Ser Thr Val
            340             345             350
Lys Arg Lys Met Glu Asn Arg Asp Tyr Arg Asp Ala Gln Glu Phe Ala
            355             360             365
Ala Asp Val Arg Leu Met Phe Ser Asn Cys Tyr Lys Tyr Asn Pro Pro
            370             375             380
Asp His Asp Val Val Ala Met Ala Arg Lys Leu Gln Asp Val Phe Glu
385             390             395             400
Phe Arg Tyr Ala Lys Met Pro Asp Glu Pro Leu Glu Pro Gly Pro Leu
                405             410             415
Pro Val Ser Thr Ala Met Pro Pro Gly Leu Ala Lys Ser Ser Ser Glu
            420             425             430
Ser Ser Ser Glu Glu Ser Ser Ser Glu Ser Ser Ser Glu Glu Glu
            435             440             445
Glu Glu Asp Glu Glu Asp Glu Glu Glu Glu Ser Glu Ser Ser Asp
        450             455             460
Ser Glu Glu Glu Arg Ala His Arg Leu Ala Glu Leu Gln Glu Gln Leu
465             470             475             480
Arg Ala Val His Glu Gln Leu Ala Ala Leu Ser Gln Gly Pro Ile Ser
                485             490             495
Lys Pro Lys Arg Lys Arg Glu Lys Lys Glu Lys Lys Lys Arg Lys
            500             505             510
Ala Glu Lys His Arg Gly Arg Ala Gly Ala Asp Glu Asp Lys Gly
            515             520             525
Pro Arg Ala Pro Arg Pro Pro Gln Pro Lys Lys Ser Lys Lys Ala Ser
            530             535             540
Gly Ser Gly Gly Gly Ser Ala Ala Leu Gly Pro Ser Gly Phe Gly Pro
545             550             555             560
Ser Gly Gly Ser Gly Thr Lys Leu Pro Lys Lys Ala Thr Lys Thr Ala
                565             570             575
Pro Pro Ala Leu Pro Thr Gly Tyr Asp Ser Glu Glu Glu Glu Ser
            580             585             590
Arg Pro Met Ser Tyr Asp Glu Lys Arg Gln Leu Ser Leu Asp Ile Asn
            595             600             605
```

```
Lys Leu Pro Gly Glu Lys Leu Gly Arg Val Val His Ile Ile Gln Ala
        610                 615                 620
Arg Glu Pro Ser Leu Arg Asp Ser Asn Pro Glu Ile Glu Ile Asp
625                 630                 635                 640
Phe Glu Thr Leu Lys Pro Ser Thr Leu Arg Glu Leu Glu Arg Tyr Val
                645                 650                 655
Leu Ser Cys Leu Arg Lys Lys Pro Arg Lys Pro Tyr Thr Ile Lys Lys
                660                 665                 670
Pro Val Gly Lys Thr Lys Glu Glu Leu Ala Leu Glu Lys Lys Arg Glu
            675                 680                 685
Leu Glu Lys Arg Leu Gln Asp Val Ser Gly Gln Leu Asn Ser Thr Lys
690                 695                 700
Lys Pro Pro Lys Lys Ala Asn Glu Lys Thr Glu Ser Ser Ser Ala Gln
705                 710                 715                 720
Gln Val Ala Val Ser Arg Leu Ser Ala Ser Ser Ser Ser Asp Ser
                725                 730                 735
Ser Ser Ser Ser Ser Ser Ser Ser Ser Asp Thr Ser Asp Ser Asp
            740                 745                 750
Ser Gly

<210> SEQ ID NO 21
<211> LENGTH: 726
<212> TYPE: PRT
<213> ORGANISM: Homo sapiens

<400> SEQUENCE: 21

Met Ser Thr Ala Thr Val Ala Pro Ala Gly Ile Pro Ala Thr Pro
1               5                   10                  15
Gly Pro Val Asn Pro Pro Pro Glu Val Ser Asn Pro Ser Lys Pro
                20                  25                  30
Arg Lys Thr Asn Gln Leu Gln Tyr Met Gln Asn Val Val Val Lys
            35                  40                  45
Thr Leu Trp Lys His Gln Phe Ala Trp Pro Phe Tyr Gln Pro Val Asp
    50                  55                  60
Ala Ile Lys Leu Asn Leu Pro Asp Tyr His Lys Ile Ile Lys Asn Pro
65                  70                  75                  80
Met Asp Met Gly Thr Ile Lys Lys Arg Leu Glu Asn Asn Tyr Tyr Trp
                85                  90                  95
Ser Ala Ser Glu Cys Met Gln Asp Phe Asn Thr Met Phe Thr Asn Cys
                100                 105                 110
Tyr Ile Tyr Asn Lys Pro Thr Asp Asp Ile Val Leu Met Ala Gln Ala
            115                 120                 125
Leu Glu Lys Ile Phe Leu Gln Lys Val Ala Gln Met Pro Gln Glu Glu
130                 135                 140
Val Glu Leu Leu Pro Pro Ala Pro Lys Gly Lys Gly Arg Lys Pro Ala
145                 150                 155                 160
Ala Gly Ala Gln Ser Ala Gly Thr Gln Gln Val Ala Ala Val Ser Ser
                165                 170                 175
Val Ser Pro Ala Thr Pro Phe Gln Ser Val Pro Pro Thr Val Ser Gln
            180                 185                 190
Thr Pro Val Ile Ala Ala Thr Pro Val Pro Thr Ile Thr Ala Asn Val
        195                 200                 205
Thr Ser Val Pro Val Pro Pro Ala Ala Pro Pro Pro Ala Thr
    210                 215                 220
```

-continued

```
Pro Ile Val Pro Val Pro Pro Thr Pro Pro Val Lys Lys Lys
225                 230                 235                 240

Gly Val Lys Arg Lys Ala Asp Thr Thr Thr Pro Thr Thr Ser Ala Ile
                245                 250                 255

Thr Ala Ser Arg Ser Glu Ser Pro Pro Leu Ser Asp Pro Lys Gln
            260                 265                 270

Ala Lys Val Val Ala Arg Arg Glu Ser Gly Gly Arg Pro Ile Lys Pro
                275                 280                 285

Pro Lys Lys Asp Leu Glu Asp Gly Glu Val Pro Gln His Ala Gly Lys
        290                 295                 300

Lys Gly Lys Leu Ser Glu His Leu Arg Tyr Cys Asp Ser Ile Leu Arg
305                 310                 315                 320

Glu Met Leu Ser Lys Lys His Ala Ala Tyr Ala Trp Pro Phe Tyr Lys
                325                 330                 335

Pro Val Asp Ala Glu Ala Leu Glu Leu His Asp Tyr His Asp Ile Ile
                340                 345                 350

Lys His Pro Met Asp Leu Ser Thr Val Lys Arg Lys Met Asp Gly Arg
            355                 360                 365

Glu Tyr Pro Asp Ala Gln Gly Phe Ala Ala Asp Val Arg Leu Met Phe
        370                 375                 380

Ser Asn Cys Tyr Lys Tyr Asn Pro Pro Asp His Glu Val Val Ala Met
385                 390                 395                 400

Ala Arg Lys Leu Gln Asp Val Phe Glu Met Arg Phe Ala Lys Met Pro
                405                 410                 415

Asp Glu Pro Val Glu Ala Pro Ala Leu Pro Ala Pro Ala Ala Pro Met
                420                 425                 430

Val Ser Lys Gly Ala Glu Ser Ser Arg Ser Ser Glu Glu Ser Ser Ser
            435                 440                 445

Asp Ser Gly Ser Ser Asp Ser Glu Glu Arg Ala Thr Arg Leu Ala
        450                 455                 460

Glu Leu Gln Glu Gln Leu Lys Ala Val His Glu Gln Leu Ala Ala Leu
465                 470                 475                 480

Ser Gln Ala Pro Val Asn Lys Pro Lys Lys Lys Glu Lys Lys Glu
                485                 490                 495

Lys Glu Lys Lys Lys Asp Lys Glu Lys Glu Lys Glu Lys His Lys
            500                 505                 510

Val Lys Ala Glu Glu Lys Lys Ala Lys Val Ala Pro Pro Ala Lys
            515                 520                 525

Gln Ala Gln Gln Lys Lys Ala Pro Ala Lys Lys Ala Asn Ser Thr Thr
        530                 535                 540

Thr Ala Gly Arg Gln Leu Lys Lys Gly Gly Lys Gln Ala Ser Ala Ser
545                 550                 555                 560

Tyr Asp Ser Glu Glu Glu Glu Gly Leu Pro Met Ser Tyr Asp Glu
                565                 570                 575

Lys Arg Gln Leu Ser Leu Asp Ile Asn Arg Leu Pro Gly Glu Lys Leu
            580                 585                 590

Gly Arg Val Val His Ile Ile Gln Ser Arg Glu Pro Ser Leu Arg Asp
        595                 600                 605

Ser Asn Pro Asp Glu Ile Glu Ile Asp Phe Glu Thr Leu Lys Pro Thr
        610                 615                 620

Thr Leu Arg Glu Leu Glu Arg Tyr Val Lys Ser Cys Leu Gln Lys Lys
625                 630                 635                 640
```

```
Gln Arg Lys Pro Phe Ser Ala Ser Gly Lys Lys Gln Ala Ala Lys Ser
                645                 650                 655

Lys Glu Glu Leu Ala Gln Glu Lys Lys Glu Leu Glu Lys Arg Leu
                660                 665                 670

Gln Asp Val Ser Gly Gln Leu Ser Ser Ser Lys Lys Pro Ala Arg Lys
                675                 680                 685

Glu Lys Pro Gly Ser Ala Pro Ser Gly Gly Pro Ser Arg Leu Ser Ser
690                 695                 700

Ser Ser Ser Ser Glu Ser Gly Ser Ser Ser Ser Gly Ser Ser Ser
705                 710                 715                 720

Asp Ser Ser Asp Ser Glu
                725

<210> SEQ ID NO 22
<211> LENGTH: 722
<212> TYPE: PRT
<213> ORGANISM: Homo sapiens

<400> SEQUENCE: 22

Met Ser Ala Glu Ser Gly Pro Gly Thr Arg Leu Arg Asn Leu Pro Val
 1               5                  10                  15

Met Gly Asp Gly Leu Glu Thr Ser Gln Met Ser Thr Thr Gln Ala Gln
                20                  25                  30

Ala Gln Pro Gln Pro Ala Asn Ala Ala Ser Thr Asn Pro Pro Pro
                35                  40                  45

Glu Thr Ser Asn Pro Asn Lys Pro Lys Arg Gln Thr Asn Gln Leu Gln
    50                  55                  60

Tyr Leu Leu Arg Val Val Leu Lys Thr Leu Trp Lys His Gln Phe Ala
65                  70                  75                  80

Trp Pro Phe Gln Gln Pro Val Asp Ala Val Lys Leu Asn Leu Pro Asp
                85                  90                  95

Tyr Tyr Lys Ile Ile Lys Thr Pro Met Asp Met Gly Thr Ile Lys Lys
                100                 105                 110

Arg Leu Glu Asn Asn Tyr Tyr Trp Asn Ala Gln Glu Cys Ile Gln Asp
                115                 120                 125

Phe Asn Thr Met Phe Thr Asn Cys Tyr Ile Tyr Asn Lys Pro Gly Asp
    130                 135                 140

Asp Ile Val Leu Met Ala Glu Ala Leu Glu Lys Leu Phe Leu Gln Lys
145                 150                 155                 160

Ile Asn Glu Leu Pro Thr Glu Thr Glu Ile Met Ile Val Gln Ala
                165                 170                 175

Lys Gly Arg Gly Arg Gly Arg Lys Glu Thr Gly Thr Ala Lys Pro Gly
                180                 185                 190

Val Ser Thr Val Pro Asn Thr Thr Gln Ala Ser Thr Pro Pro Gln Thr
                195                 200                 205

Gln Thr Pro Gln Pro Asn Pro Pro Val Gln Ala Thr Pro His Pro
    210                 215                 220

Phe Pro Ala Val Thr Pro Asp Leu Ile Val Gln Thr Pro Val Met Thr
225                 230                 235                 240

Val Val Pro Pro Gln Pro Leu Gln Thr Pro Pro Val Pro Pro Gln
                245                 250                 255

Pro Gln Pro Pro Pro Ala Pro Ala Pro Gln Pro Val Gln Ser His Pro
                260                 265                 270

Pro Ile Ile Ala Ala Thr Pro Gln Pro Val Lys Thr Lys Lys Gly Val
                275                 280                 285
```

```
Lys Arg Lys Ala Asp Thr Thr Thr Pro Thr Thr Ile Asp Pro Ile His
    290                 295                 300
Glu Pro Pro Ser Leu Pro Pro Glu Pro Lys Thr Thr Lys Leu Gly Gln
305                 310                 315                 320
Arg Arg Glu Ser Ser Arg Pro Val Lys Pro Pro Lys Lys Asp Val Pro
                325                 330                 335
Asp Ser Gln Gln His Pro Ala Pro Glu Lys Ser Ser Lys Val Ser Glu
                340                 345                 350
Gln Leu Lys Cys Cys Ser Gly Ile Leu Lys Glu Met Phe Ala Lys Lys
            355                 360                 365
His Ala Ala Tyr Ala Trp Pro Phe Tyr Lys Pro Val Asp Val Glu Ala
    370                 375                 380
Leu Gly Leu His Asp Tyr Cys Asp Ile Ile Lys His Pro Met Asp Met
385                 390                 395                 400
Ser Thr Ile Lys Ser Lys Leu Glu Ala Arg Glu Tyr Arg Asp Ala Gln
                405                 410                 415
Glu Phe Gly Ala Asp Val Arg Leu Met Phe Ser Asn Cys Tyr Lys Tyr
                420                 425                 430
Asn Pro Pro Asp His Glu Val Val Ala Met Ala Arg Lys Leu Gln Asp
                435                 440                 445
Val Phe Glu Met Arg Phe Ala Lys Met Pro Asp Glu Pro Glu Glu Pro
            450                 455                 460
Val Val Ala Val Ser Ser Pro Ala Val Pro Pro Thr Lys Val Val
465                 470                 475                 480
Ala Pro Pro Ser Ser Ser Asp Ser Ser Ser Asp Ser Ser Ser Asp Ser
                485                 490                 495
Asp Ser Ser Thr Asp Asp Ser Glu Glu Glu Arg Ala Gln Arg Leu Ala
                500                 505                 510
Glu Leu Gln Glu Gln Leu Lys Ala Val His Glu Gln Leu Ala Ala Leu
        515                 520                 525
Ser Gln Pro Gln Gln Asn Lys Pro Lys Lys Lys Glu Lys Asp Lys Lys
    530                 535                 540
Glu Lys Lys Lys Glu Lys His Lys Arg Lys Glu Glu Val Glu Glu Asn
545                 550                 555                 560
Lys Lys Ser Lys Ala Lys Glu Pro Pro Lys Lys Thr Lys Lys Asn
                565                 570                 575
Asn Ser Ser Asn Ser Asn Val Ser Lys Lys Glu Pro Ala Pro Met Lys
            580                 585                 590
Ser Lys Pro Pro Pro Thr Tyr Glu Ser Glu Glu Glu Asp Lys Cys Lys
                595                 600                 605
Pro Met Ser Tyr Glu Glu Lys Arg Gln Leu Ser Leu Asp Ile Asn Lys
    610                 615                 620
Leu Pro Gly Glu Lys Leu Gly Arg Val Val His Ile Ile Gln Ser Arg
625                 630                 635                 640
Glu Pro Ser Leu Lys Asn Ser Asn Pro Asp Glu Ile Glu Ile Asp Phe
                645                 650                 655
Glu Thr Leu Lys Pro Ser Thr Leu Arg Glu Leu Glu Arg Tyr Val Thr
                660                 665                 670
Ser Cys Leu Arg Lys Lys Arg Lys Pro Gln Ala Glu Lys Val Asp Val
            675                 680                 685
Ile Ala Gly Ser Ser Lys Met Lys Gly Phe Ser Ser Ser Glu Ser Glu
    690                 695                 700
```

```
Ser Ser Ser Glu Ser Ser Ser Asp Ser Glu Asp Ser Glu Thr Gly
705             710             715             720

Pro Ala

<210> SEQ ID NO 23
<211> LENGTH: 947
<212> TYPE: PRT
<213> ORGANISM: Homo sapiens

<400> SEQUENCE: 23

Met Ser Leu Pro Ser Arg Gln Thr Ala Ile Ile Val Asn Pro Pro
1               5               10              15

Pro Glu Tyr Ile Asn Thr Lys Lys Asn Gly Arg Leu Thr Asn Gln Leu
            20              25              30

Gln Tyr Leu Gln Lys Val Val Leu Lys Asp Leu Trp Lys His Ser Phe
        35              40              45

Ser Trp Pro Phe Gln Arg Pro Val Asp Ala Val Lys Leu Lys Leu Pro
50              55              60

Asp Tyr Tyr Thr Ile Ile Lys Asn Pro Met Asp Leu Asn Thr Ile Lys
65              70              75              80

Lys Arg Leu Glu Asn Lys Tyr Tyr Ala Lys Ala Ser Glu Cys Ile Glu
                85              90              95

Asp Phe Asn Thr Met Phe Ser Asn Cys Tyr Leu Tyr Asn Lys Pro Gly
            100             105             110

Asp Asp Ile Val Leu Met Ala Gln Ala Leu Glu Lys Leu Phe Met Gln
        115             120             125

Lys Leu Ser Gln Met Pro Gln Glu Glu Gln Val Val Gly Val Lys Glu
130             135             140

Arg Ile Lys Lys Gly Thr Gln Gln Asn Ile Ala Val Ser Ser Ala Lys
145             150             155             160

Glu Lys Ser Ser Pro Ser Ala Thr Glu Lys Val Phe Lys Gln Gln Glu
                165             170             175

Ile Pro Ser Val Phe Pro Lys Thr Ser Ile Ser Pro Leu Asn Val Val
            180             185             190

Gln Gly Ala Ser Val Asn Ser Ser Ser Gln Thr Ala Ala Gln Val Thr
        195             200             205

Lys Gly Val Lys Arg Lys Ala Asp Thr Thr Thr Pro Ala Thr Ser Ala
210             215             220

Val Lys Ala Ser Ser Glu Phe Ser Pro Thr Phe Thr Glu Lys Ser Val
225             230             235             240

Ala Leu Pro Pro Ile Lys Glu Asn Met Pro Lys Asn Val Leu Pro Asp
                245             250             255

Ser Gln Gln Gln Tyr Asn Val Val Glu Thr Val Lys Val Thr Glu Gln
            260             265             270

Leu Arg His Cys Ser Glu Ile Leu Lys Glu Met Leu Ala Lys Lys His
        275             280             285

Phe Ser Tyr Ala Trp Pro Phe Tyr Asn Pro Val Asp Val Asn Ala Leu
290             295             300

Gly Leu His Asn Tyr Tyr Asp Val Val Lys Asn Pro Met Asp Leu Gly
305             310             315             320

Thr Ile Lys Glu Lys Met Asp Asn Gln Glu Tyr Lys Asp Ala Tyr Ser
                325             330             335

Phe Ala Ala Asp Val Arg Leu Met Phe Met Asn Cys Tyr Lys Tyr Asn
            340             345             350
```

-continued

```
Pro Pro Asp His Glu Val Val Thr Met Ala Arg Met Leu Gln Asp Val
        355                 360                 365
Phe Glu Thr His Phe Ser Lys Ile Pro Ile Glu Pro Val Glu Ser Met
        370                 375                 380
Pro Leu Cys Tyr Ile Lys Thr Asp Ile Thr Glu Thr Thr Gly Arg Glu
385                 390                 395                 400
Asn Thr Asn Glu Ala Ser Ser Glu Gly Asn Ser Ser Asp Asp Ser Glu
                405                 410                 415
Asp Glu Arg Val Lys Arg Leu Ala Lys Leu Gln Glu Gln Leu Lys Ala
                420                 425                 430
Val His Gln Gln Leu Gln Val Leu Ser Gln Val Pro Phe Arg Lys Leu
                435                 440                 445
Asn Lys Lys Glu Lys Ser Lys Glu Lys Lys Lys Glu Lys Val
450                 455                 460
Asn Asn Ser Asn Glu Asn Pro Arg Lys Met Cys Glu Gln Met Arg Leu
465                 470                 475                 480
Lys Glu Lys Ser Lys Arg Asn Gln Pro Lys Lys Arg Lys Gln Gln Phe
                485                 490                 495
Ile Gly Leu Lys Ser Glu Asp Glu Asn Ala Lys Pro Met Asn Tyr
                500                 505                 510
Asp Glu Lys Arg Gln Leu Ser Leu Asn Ile Asn Lys Leu Pro Gly Asp
                515                 520                 525
Lys Leu Gly Arg Val Val His Ile Ile Gln Ser Arg Glu Pro Ser Leu
                530                 535                 540
Ser Asn Ser Asn Pro Asp Glu Ile Glu Ile Asp Phe Glu Thr Leu Lys
545                 550                 555                 560
Ala Ser Thr Leu Arg Glu Leu Glu Lys Tyr Val Ser Ala Cys Leu Arg
                565                 570                 575
Lys Arg Pro Leu Lys Pro Pro Ala Lys Lys Ile Met Met Ser Lys Glu
                580                 585                 590
Glu Leu His Ser Gln Lys Lys Gln Leu Glu Lys Arg Leu Leu Asp
                595                 600                 605
Val Asn Asn Gln Leu Asn Ser Arg Lys Arg Gln Thr Lys Ser Asp Lys
                610                 615                 620
Thr Gln Pro Ser Lys Ala Val Glu Asn Val Ser Arg Leu Ser Glu Ser
625                 630                 635                 640
Ser Ser Ser Ser Ser Ser Ser Glu Ser Glu Ser Ser Ser Ser Asp
                645                 650                 655
Leu Ser Ser Ser Asp Ser Ser Asp Ser Glu Ser Glu Met Phe Pro Lys
                660                 665                 670
Phe Thr Glu Val Lys Pro Asn Asp Ser Pro Ser Lys Glu His Val Lys
                675                 680                 685
Lys Met Lys Asn Glu Cys Ile Leu Pro Glu Gly Arg Thr Gly Val Thr
                690                 695                 700
Gln Ile Gly Tyr Cys Val Gln Asp Thr Thr Ser Ala Asn Thr Leu
705                 710                 715                 720
Val His Gln Thr Thr Pro Ser His Val Met Pro Pro Asn His Gln
                725                 730                 735
Leu Ala Phe Asn Tyr Gln Glu Leu Glu His Leu Gln Thr Val Lys Asn
                740                 745                 750
Ile Ser Pro Leu Gln Ile Leu Pro Pro Ser Gly Asp Ser Glu Gln Leu
                755                 760                 765
Ser Asn Gly Ile Thr Val Met His Pro Ser Gly Asp Ser Asp Thr Thr
```

-continued

```
              770                 775                 780
Met Leu Glu Ser Glu Cys Gln Ala Pro Val Gln Lys Asp Ile Lys Ile
785                 790                 795                 800

Lys Asn Ala Asp Ser Trp Lys Ser Leu Gly Lys Pro Val Lys Pro Ser
                805                 810                 815

Gly Val Met Lys Ser Ser Asp Glu Leu Phe Asn Gln Phe Arg Lys Ala
            820                 825                 830

Ala Ile Glu Lys Glu Val Lys Ala Arg Thr Gln Glu Leu Ile Arg Lys
                835                 840                 845

His Leu Glu Gln Asn Thr Lys Glu Leu Lys Ala Ser Gln Glu Asn Gln
            850                 855                 860

Arg Asp Leu Gly Asn Gly Leu Thr Val Glu Ser Phe Ser Asn Lys Ile
865                 870                 875                 880

Gln Asn Lys Cys Ser Gly Glu Glu Gln Lys Glu His Pro Gln Ser Ser
                885                 890                 895

Glu Ala Gln Asp Lys Ser Lys Leu Trp Leu Leu Lys Asp Arg Asp Leu
            900                 905                 910

Ala Arg Pro Lys Glu Gln Glu Arg Arg Arg Glu Ala Met Val Gly
                915                 920                 925

Thr Ile Asp Met Thr Leu Gln Ser Asp Ile Met Thr Met Phe Glu Asn
            930                 935                 940

Asn Phe Asp
945

<210> SEQ ID NO 24
<211> LENGTH: 973
<212> TYPE: PRT
<213> ORGANISM: Homo sapiens

<400> SEQUENCE: 24

Met Glu Lys Gln Lys Pro Phe Ala Leu Phe Val Pro Pro Arg Ser Ser
  1               5                  10                  15

Ser Ser Gln Val Ser Ala Val Lys Pro Gln Thr Leu Gly Gly Asp Ser
                 20                  25                  30

Thr Phe Phe Lys Ser Phe Asn Lys Cys Thr Glu Asp Asp Phe Glu Phe
             35                  40                  45

Pro Phe Ala Lys Thr Asn Leu Ser Lys Asn Gly Glu Asn Ile Asp Ser
 50                  55                  60

Asp Pro Ala Leu Gln Lys Val Asn Phe Leu Pro Val Leu Glu Gln Val
 65                  70                  75                  80

Gly Asn Ser Asp Cys His Tyr Gln Glu Gly Leu Lys Asp Ser Asp Leu
                 85                  90                  95

Glu Asn Ser Glu Gly Leu Ser Arg Val Tyr Ser Lys Leu Tyr Lys Glu
            100                 105                 110

Ala Glu Lys Ile Lys Lys Trp Lys Val Ser Thr Glu Ala Glu Leu Arg
        115                 120                 125

Gln Lys Glu Ser Lys Leu Gln Glu Asn Arg Lys Ile Ile Glu Ala Gln
    130                 135                 140

Arg Lys Ala Ile Gln Glu Leu Gln Cys Gly Asn Glu Lys Val Ser Leu
145                 150                 155                 160

Thr Leu Glu Glu Gly Ile Gln Asp Asn Lys Asp Leu Ile Lys Glu Asn
                165                 170                 175

Asn Ala Thr Arg His Leu Cys Asn Leu Leu Lys Glu Thr Cys Ala Arg
            180                 185                 190
```

-continued

```
Ser Ala Glu Lys Thr Lys Lys Tyr Glu Tyr Glu Arg Glu Thr Arg
        195                 200                 205
Gln Val Tyr Met Asp Leu Asn Ser Asn Ile Glu Lys Met Ile Thr Ala
        210                 215                 220
Phe Glu Glu Leu Arg Val Gln Ala Glu Asn Ser Arg Leu Glu Met His
225                 230                 235                 240
Phe Lys Leu Lys Glu Asp Tyr Glu Lys Ile Gln His Leu Glu Gln Glu
                245                 250                 255
Tyr Lys Lys Glu Ile Asn Asp Lys Glu Lys Gln Val Ser Leu Leu Leu
                260                 265                 270
Ile Gln Ile Thr Glu Lys Glu Asn Lys Met Lys Asp Leu Thr Phe Leu
        275                 280                 285
Leu Glu Glu Ser Arg Asp Lys Val Asn Gln Leu Glu Glu Lys Thr Lys
        290                 295                 300
Leu Gln Ser Glu Asn Leu Lys Gln Ser Ile Glu Lys Gln His His Leu
305                 310                 315                 320
Thr Lys Glu Leu Glu Asp Ile Lys Val Ser Leu Gln Arg Ser Val Ser
                325                 330                 335
Thr Gln Lys Ala Leu Glu Glu Asp Leu Gln Ile Ala Thr Asn Thr Ile
        340                 345                 350
Cys Gln Leu Thr Glu Glu Lys Asp Thr Gln Met Glu Glu Ser Asn Lys
        355                 360                 365
Ala Arg Ala His Ser Phe Val Val Thr Glu Phe Glu Thr Thr Val
        370                 375                 380
Cys Ser Leu Glu Glu Leu Leu Arg Thr Glu Gln Gln Arg Leu Glu Asn
385                 390                 395                 400
Tyr Glu Asp Gln Leu Ile Ile Leu Thr Met Glu Leu Gln Lys Thr Ser
                405                 410                 415
Ser Glu Leu Glu Glu Met Thr Lys Leu Thr Asn Asn Lys Glu Val Glu
                420                 425                 430
Leu Glu Glu Leu Lys Lys Val Leu Gly Glu Lys Glu Thr Leu Leu Tyr
        435                 440                 445
Asp Asn Lys Gln Phe Glu Lys Ile Ala Glu Glu Leu Lys Gly Thr Glu
        450                 455                 460
Gln Glu Leu Ile Gly Leu Leu Gln Ala Arg Glu Lys Glu Val His Asp
465                 470                 475                 480
Leu Glu Tyr Ser Tyr Cys His Tyr His Lys Trp Thr Val Leu Pro Lys
                485                 490                 495
Arg Gly Gln Arg Pro Lys Leu Ser Ser Lys Arg Glu Leu Lys Asn Thr
                500                 505                 510
Glu Tyr Phe Thr Leu Gln Gln Ala Ser Pro Pro Asn Glu Leu Thr
        515                 520                 525
Gln Glu Thr Ser Asp Met Thr Leu Glu Leu Lys Asn Gln Gln Glu Asp
        530                 535                 540
Ile Ile Asn Asn Lys Lys Gln Glu Glu Arg Met Leu Thr Gln Ile Glu
545                 550                 555                 560
Asn Leu Gln Glu Thr Glu Thr Gln Leu Arg Asn Glu Leu Glu Tyr Val
                565                 570                 575
Arg Glu Glu Leu Lys Gln Lys Arg Asp Glu Val Lys Cys Lys Leu Asp
                580                 585                 590
Lys Ser Glu Glu Asn Cys Asn Asn Leu Arg Lys Gln Val Glu Asn Lys
        595                 600                 605
Asn Lys Tyr Ile Glu Glu Leu Gln Gln Glu Asn Lys Ala Leu Lys Lys
```

```
            610                 615                 620
Lys Gly Thr Ala Glu Ser Lys Gln Leu Asn Val Tyr Glu Ile Lys Val
625                 630                 635                 640

Asn Lys Leu Glu Leu Glu Leu Glu Ser Ala Lys Gln Lys Phe Gly Glu
                645                 650                 655

Ile Thr Asp Thr Tyr Gln Lys Glu Ile Glu Asp Lys Lys Ile Ser Glu
                660                 665                 670

Glu Asn Leu Leu Glu Glu Val Glu Lys Ala Lys Val Ile Ala Asp Glu
                675                 680                 685

Ala Val Lys Leu Gln Lys Glu Ile Asp Lys Arg Cys Gln His Lys Ile
690                 695                 700

Ala Glu Met Val Ala Leu Met Glu Lys His Lys His Gln Tyr Asp Lys
705                 710                 715                 720

Ile Ile Glu Glu Arg Asp Ser Glu Leu Gly Leu Tyr Lys Ser Lys Glu
                725                 730                 735

Gln Glu Gln Ser Ser Leu Arg Ala Ser Leu Glu Ile Glu Leu Ser Asn
                740                 745                 750

Leu Lys Ala Glu Leu Leu Ser Val Lys Lys Gln Leu Glu Ile Glu Arg
                755                 760                 765

Glu Glu Lys Glu Lys Leu Lys Arg Glu Ala Lys Glu Asn Thr Ala Thr
770                 775                 780

Leu Lys Glu Lys Lys Asp Lys Lys Thr Gln Thr Phe Leu Leu Glu Thr
785                 790                 795                 800

Pro Asp Ile Tyr Trp Lys Leu Asp Ser Lys Ala Val Pro Ser Gln Thr
                805                 810                 815

Val Ser Arg Asn Phe Thr Ser Val Asp His Gly Ile Ser Lys Asp Lys
                820                 825                 830

Arg Asp Tyr Leu Trp Thr Ser Ala Lys Asn Thr Leu Ser Thr Pro Leu
                835                 840                 845

Pro Lys Ala Tyr Thr Val Lys Thr Pro Thr Lys Pro Lys Leu Gln Gln
850                 855                 860

Arg Glu Asn Leu Asn Ile Pro Ile Glu Glu Ser Lys Lys Lys Arg Lys
865                 870                 875                 880

Met Ala Phe Glu Phe Asp Ile Asn Ser Asp Ser Ser Glu Thr Thr Asp
                885                 890                 895

Leu Leu Ser Met Val Ser Glu Glu Thr Leu Lys Thr Leu Tyr Arg
                900                 905                 910

Asn Asn Asn Pro Pro Ala Ser His Leu Cys Val Lys Thr Pro Lys Lys
                915                 920                 925

Ala Pro Ser Ser Leu Thr Thr Pro Gly Ser Thr Leu Lys Phe Gly Ala
930                 935                 940

Ile Arg Lys Met Arg Glu Asp Arg Trp Ala Val Ile Ala Lys Met Asp
945                 950                 955                 960

Arg Lys Lys Lys Leu Lys Glu Ala Glu Lys Leu Phe Val
                965                 970

<210> SEQ ID NO 25
<211> LENGTH: 180
<212> TYPE: PRT
<213> ORGANISM: Homo sapiens

<400> SEQUENCE: 25

Met Gln Ala Glu Gly Arg Gly Thr Gly Gly Ser Thr Gly Asp Ala Asp
1               5                   10                  15
```

-continued

```
Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Ala Pro Arg Gly Pro
        50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 26
<211> LENGTH: 1142
<212> TYPE: PRT
<213> ORGANISM: Homo sapiens

<400> SEQUENCE: 26

Met Gly Asp Lys Asp Met Pro Thr Ala Gly Met Pro Ser Leu Leu Gln
1               5                   10                  15

Ser Ser Ser Glu Ser Pro Gln Ser Cys Pro Glu Gly Glu Asp Ser Gln
                20                  25                  30

Ser Pro Leu Gln Ile Pro Gln Ser Pro Glu Ser Asp Asp Thr Leu
            35                  40                  45

Tyr Pro Leu Gln Ser Pro Gln Ser Arg Ser Glu Gly Glu Asp Ser Ser
        50                  55                  60

Asp Pro Leu Gln Arg Pro Pro Glu Gly Lys Asp Ser Gln Ser Pro Leu
65                  70                  75                  80

Gln Ile Pro Gln Ser Ser Pro Glu Gly Asp Asp Thr Gln Ser Pro Leu
                85                  90                  95

Gln Asn Ser Gln Ser Ser Pro Glu Gly Lys Asp Ser Leu Ser Pro Leu
                100                 105                 110

Glu Ile Ser Gln Ser Pro Pro Glu Gly Glu Asp Val Gln Ser Pro Leu
            115                 120                 125

Gln Asn Pro Ala Ser Ser Phe Phe Ser Ser Ala Leu Leu Ser Ile Phe
        130                 135                 140

Gln Ser Ser Pro Glu Ser Ile Gln Ser Pro Phe Glu Gly Phe Pro Gln
145                 150                 155                 160

Ser Val Leu Gln Ile Pro Val Ser Ala Ala Ser Ser Thr Leu Val
                165                 170                 175

Ser Ile Phe Gln Ser Ser Pro Glu Ser Thr Gln Ser Pro Phe Glu Gly
            180                 185                 190

Phe Pro Gln Ser Pro Leu Gln Ile Pro Val Ser Arg Ser Phe Ser Ser
        195                 200                 205
```

-continued

```
Thr Leu Leu Ser Ile Phe Gln Ser Ser Pro Glu Arg Ser Gln Arg Thr
    210                 215                 220
Ser Glu Gly Phe Ala Gln Ser Pro Leu Gln Ile Pro Val Ser Ser Ser
225                 230                 235                 240
Ser Ser Ser Thr Leu Leu Ser Leu Phe Gln Ser Ser Pro Glu Arg Thr
            245                 250                 255
Gln Ser Thr Phe Glu Gly Phe Pro Gln Ser Pro Leu Gln Ile Pro Val
            260                 265                 270
Ser Arg Ser Phe Ser Ser Thr Leu Leu Ser Ile Phe Gln Ser Ser Pro
        275                 280                 285
Glu Arg Thr Gln Ser Thr Phe Glu Gly Phe Ala Gln Ser Pro Leu Gln
    290                 295                 300
Ile Pro Val Ser Pro Ser Phe Ser Ser Thr Leu Val Ser Ile Phe Gln
305                 310                 315                 320
Ser Ser Pro Glu Arg Thr Gln Ser Thr Phe Glu Gly Phe Pro Gln Ser
            325                 330                 335
Pro Leu Gln Ile Pro Val Ser Ser Ser Phe Ser Ser Thr Leu Leu Ser
            340                 345                 350
Leu Phe Gln Ser Ser Pro Glu Arg Thr Gln Ser Thr Phe Glu Gly Phe
        355                 360                 365
Pro Gln Ser Pro Leu Gln Ile Pro Gly Ser Pro Ser Phe Ser Ser Thr
    370                 375                 380
Leu Leu Ser Leu Phe Gln Ser Ser Pro Glu Arg Thr His Ser Thr Phe
385                 390                 395                 400
Glu Gly Phe Pro Gln Ser Pro Leu Gln Ile Pro Met Thr Ser Ser Phe
            405                 410                 415
Ser Ser Thr Leu Leu Ser Ile Leu Gln Ser Ser Pro Glu Ser Ala Gln
            420                 425                 430
Ser Ala Phe Glu Gly Phe Pro Gln Ser Pro Leu Gln Ile Pro Val Ser
        435                 440                 445
Ser Ser Phe Ser Tyr Thr Leu Leu Ser Leu Phe Gln Ser Ser Pro Glu
    450                 455                 460
Arg Thr His Ser Thr Phe Glu Gly Phe Pro Gln Ser Pro Leu Gln Ile
465                 470                 475                 480
Pro Val Ser Ser Ser Ser Ser Ser Thr Leu Leu Ser Leu Phe Gln
            485                 490                 495
Ser Ser Pro Glu Cys Thr Gln Ser Thr Phe Glu Gly Phe Pro Gln Ser
            500                 505                 510
Pro Leu Gln Ile Pro Gln Ser Pro Pro Glu Gly Glu Asn Thr His Ser
        515                 520                 525
Pro Leu Gln Ile Val Pro Ser Leu Pro Glu Trp Glu Asp Ser Leu Ser
    530                 535                 540
Pro His Tyr Phe Pro Gln Ser Pro Pro Gln Gly Glu Asp Ser Leu Ser
545                 550                 555                 560
Pro His Tyr Phe Pro Gln Ser Pro Gln Gly Glu Asp Ser Leu Ser
            565                 570                 575
Pro His Tyr Phe Pro Gln Ser Pro Gln Gly Glu Asp Ser Leu Ser Pro
            580                 585                 590
His Tyr Phe Pro Gln Ser Pro Pro Gln Gly Glu Asp Ser Met Ser Pro
        595                 600                 605
Leu Tyr Phe Pro Gln Ser Pro Leu Gln Gly Glu Glu Phe Gln Ser Ser
    610                 615                 620
```

```
Leu Gln Ser Pro Val Ser Ile Cys Ser Ser Thr Pro Ser Ser Leu
625                 630                 635                 640

Pro Gln Ser Phe Pro Glu Ser Ser Gln Ser Pro Glu Gly Pro Val
                645                 650                 655

Gln Ser Pro Leu His Ser Pro Gln Ser Pro Pro Glu Gly Met His Ser
                660                 665                 670

Gln Ser Pro Leu Gln Ser Pro Glu Ser Ala Pro Glu Gly Glu Asp Ser
                675                 680                 685

Leu Ser Pro Leu Gln Ile Pro Gln Ser Pro Leu Glu Gly Asp Ser
690                 695                 700

Leu Ser Ser Leu His Phe Pro Gln Ser Pro Pro Glu Trp Glu Asp Ser
705                 710                 715                 720

Leu Ser Pro Leu His Phe Pro Gln Phe Pro Pro Gln Gly Glu Asp Phe
                725                 730                 735

Gln Ser Ser Leu Gln Ser Pro Val Ser Ile Cys Ser Ser Ser Thr Ser
                740                 745                 750

Leu Ser Leu Pro Gln Ser Phe Pro Glu Ser Pro Gln Ser Pro Pro Glu
                755                 760                 765

Gly Pro Ala Gln Ser Pro Leu Gln Arg Pro Val Ser Ser Phe Phe Ser
770                 775                 780

Tyr Thr Leu Ala Ser Leu Leu Gln Ser Ser His Glu Ser Pro Gln Ser
785                 790                 795                 800

Pro Pro Glu Gly Pro Ala Gln Ser Pro Leu Gln Ser Pro Val Ser Ser
                805                 810                 815

Phe Pro Ser Ser Thr Ser Ser Leu Ser Gln Ser Ser Pro Val Ser
                820                 825                 830

Ser Phe Pro Ser Ser Thr Ser Ser Leu Ser Lys Ser Ser Pro Glu
                835                 840                 845

Ser Pro Leu Gln Ser Pro Val Ile Ser Phe Ser Ser Thr Ser Leu
                850                 855                 860

Ser Pro Phe Ser Glu Glu Ser Ser Pro Val Asp Glu Tyr Thr Ser
865                 870                 875                 880

Ser Ser Asp Thr Leu Leu Glu Ser Asp Ser Leu Thr Asp Ser Glu Ser
                885                 890                 895

Leu Ile Glu Ser Glu Pro Leu Phe Thr Tyr Thr Leu Asp Glu Lys Val
                900                 905                 910

Asp Glu Leu Ala Arg Phe Leu Leu Lys Tyr Gln Val Lys Gln Pro
                915                 920                 925

Ile Thr Lys Ala Glu Met Leu Thr Asn Val Ile Ser Arg Tyr Thr Gly
                930                 935                 940

Tyr Phe Pro Val Ile Phe Arg Lys Ala Arg Glu Phe Ile Glu Ile Leu
945                 950                 955                 960

Phe Gly Ile Ser Leu Arg Glu Val Asp Pro Asp Ser Tyr Val Phe
                965                 970                 975

Val Asn Thr Leu Asp Leu Thr Ser Glu Gly Cys Leu Ser Asp Glu Gln
                980                 985                 990

Gly Met Ser Gln Asn Arg Leu Leu Ile Leu Ile Leu Ser Ile Ile Phe
                995                 1000                1005

Ile Lys Gly Thr Tyr Ala Ser Glu Glu Val Ile Trp Asp Val Leu Ser
        1010                1015                1020

Gly Ile Gly Val Arg Ala Gly Arg Glu His Phe Ala Phe Gly Glu Pro
1025                1030                1035                1040

Arg Glu Leu Leu Thr Lys Val Trp Val Gln Glu His Tyr Leu Glu Tyr
```

```
                  1045              1050             1055
Arg Glu Val Pro Asn Ser Ser Pro Pro Arg Tyr Glu Phe Leu Trp Gly
                1060             1065            1070

Pro Arg Ala His Ser Glu Val Ile Lys Arg Lys Val Val Glu Phe Leu
            1075             1080            1085

Ala Met Leu Lys Asn Thr Val Pro Ile Thr Phe Pro Ser Ser Tyr Lys
        1090             1095            1100

Asp Ala Leu Lys Asp Val Glu Glu Arg Ala Gln Ala Ile Ile Asp Thr
1105            1110            1115            1120

Thr Asp Asp Ser Thr Ala Thr Glu Ser Ala Ser Ser Val Met Ser
                1125            1130            1135

Pro Ser Phe Ser Ser Glu
            1140

<210> SEQ ID NO 27
<211> LENGTH: 188
<212> TYPE: PRT
<213> ORGANISM: Homo sapiens

<400> SEQUENCE: 27

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
            20                  25                  30

Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185

<210> SEQ ID NO 28
<211> LENGTH: 188
<212> TYPE: PRT
<213> ORGANISM: Homo sapiens

<400> SEQUENCE: 28

Met Asn Gly Asp Asp Ala Phe Ala Arg Arg Pro Arg Asp Asp Ala Gln
1               5                   10                  15

Ile Ser Glu Lys Leu Arg Lys Ala Phe Asp Asp Ile Ala Lys Tyr Phe
            20                  25                  30

Ser Lys Lys Glu Trp Glu Lys Met Lys Ser Ser Glu Lys Ile Val Tyr
```

```
                      35                  40                  45
Val Tyr Met Lys Leu Asn Tyr Glu Val Met Thr Lys Leu Gly Phe Lys
         50                  55                  60
Val Thr Leu Pro Pro Phe Met Arg Ser Lys Arg Ala Ala Asp Phe His
 65                  70                  75                  80
Gly Asn Asp Phe Gly Asn Asp Arg Asn His Arg Asn Gln Val Glu Arg
                 85                  90                  95
Pro Gln Met Thr Phe Gly Ser Leu Gln Arg Ile Phe Pro Lys Ile Met
                100                 105                 110
Pro Lys Lys Pro Ala Glu Glu Asn Gly Leu Lys Glu Val Pro Glu
                115                 120                 125
Ala Ser Gly Pro Gln Asn Asp Gly Lys Gln Leu Cys Pro Pro Gly Asn
        130                 135                 140
Pro Ser Thr Leu Glu Lys Ile Asn Lys Thr Ser Gly Pro Lys Arg Gly
145                 150                 155                 160
Lys His Ala Trp Thr His Arg Leu Arg Glu Arg Lys Gln Leu Val Val
                165                 170                 175
Tyr Glu Glu Ile Ser Asp Pro Glu Glu Asp Asp Glu
                180                 185

<210> SEQ ID NO 29
<211> LENGTH: 309
<212> TYPE: PRT
<213> ORGANISM: Homo sapiens

<400> SEQUENCE: 29

Met Ser Leu Glu Gln Arg Ser Leu His Cys Lys Pro Glu Glu Ala Leu
 1               5                  10                  15
Glu Ala Gln Gln Glu Ala Leu Gly Leu Val Cys Val Gln Ala Ala Thr
                20                  25                  30
Ser Ser Ser Ser Pro Leu Val Leu Gly Thr Leu Glu Glu Val Pro Thr
            35                  40                  45
Ala Gly Ser Thr Asp Pro Pro Gln Ser Pro Gln Gly Ala Ser Ala Phe
        50                  55                  60
Pro Thr Thr Ile Asn Phe Thr Arg Gln Arg Gln Pro Ser Glu Gly Ser
 65                  70                  75                  80
Ser Ser Arg Glu Glu Glu Gly Pro Ser Thr Ser Cys Ile Leu Glu Ser
                 85                  90                  95
Leu Phe Arg Ala Val Ile Thr Lys Lys Val Ala Asp Leu Val Gly Phe
                100                 105                 110
Leu Leu Leu Lys Tyr Arg Ala Arg Glu Pro Val Thr Lys Ala Glu Met
                115                 120                 125
Leu Glu Ser Val Ile Lys Asn Tyr Lys His Cys Phe Pro Glu Ile Phe
        130                 135                 140
Gly Lys Ala Ser Glu Ser Leu Gln Leu Val Phe Gly Ile Asp Val Lys
145                 150                 155                 160
Glu Ala Asp Pro Thr Gly His Ser Tyr Val Leu Val Thr Cys Leu Gly
                165                 170                 175
Leu Ser Tyr Asp Gly Leu Leu Gly Asp Asn Gln Ile Met Pro Lys Thr
                180                 185                 190
Gly Phe Leu Ile Ile Val Leu Val Met Ile Ala Met Glu Gly Gly His
            195                 200                 205
Ala Pro Glu Glu Glu Ile Trp Glu Glu Leu Ser Val Met Glu Val Tyr
        210                 215                 220
```

-continued

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
            245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
            275                 280                 285

Arg Val Arg Phe Phe Phe Pro Ser Leu Arg Glu Ala Ala Leu Arg Glu
            290                 295                 300

Glu Glu Glu Gly Val
305

<210> SEQ ID NO 30
<211> LENGTH: 314
<212> TYPE: PRT
<213> ORGANISM: Homo sapiens

<400> SEQUENCE: 30

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
            35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
            130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
            195                 200                 205

Ile Ala Arg Glu Gly Asp Cys Ala Pro Glu Glu Lys Ile Trp Glu Glu
            210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
            245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
            275                 280                 285

```
His Met Val Lys Ile Ser Gly Gly Pro His Ile Ser Tyr Pro Pro Leu
    290                 295                 300

His Glu Trp Val Leu Arg Glu Gly Glu Glu
305                 310
```

CANCER ASSOCIATED ANTIGENS AND USES THEREFOR

RELATED APPLICATIONS

This application is a continuation-in-part of PCT application PCT/US98/14679, filed Jul. 15, 1998, the entire disclosure of which is incorporated by reference herein.

FIELD OF THE INVENTION

The invention relates to nucleic acids and encoded polypeptides which are cancer associated antigens. The invention also relates to agents which bind the nucleic acids or polypeptides. The nucleic acid molecules, polypeptides coded for by such molecules and peptides derived therefrom, as well as related antibodies and cytolytic T lymphocytes, are useful, inter alia, in diagnostic and therapeutic contexts.

BACKGROUND OF THE INVENTION

The mechanism by which T cells recognize foreign materials has been implicated in cancer. A number of cytolytic T lymphocyte (CTL) clones directed against autologous melanoma antigens, testicular antigens, and melanocyte differentiation antigens have been described. In many instances, the antigens recognized by these clones have been characterized.

The use of autologous CTLs for identifying tumor antigens requires that the target cells which express the antigens can be cultured in vitro and that stable lines of autologous CTL clones which recognize the antigen-expressing cells can be isolated and propagated. While this approach has worked well for melanoma antigens, other tumor types, such as epithelial cancers including breast and colon cancer, have proved refractory to the approach.

Recent progress in the identification of human tumor antigens has generated a repertoire of target molecules for use in antigen-specific tumor vaccines. The continued expansion of this repertoire allows for the potential development of polyvalent cancer vaccines that can be applied to several tumor types and may help circumvent some of the difficulties associated with active immunotherapy, such as tumor heterogeneity and antigen loss. Human tumor antigens fall into several categories, including autoimmunogenic differentiation antigens (e.g., tyrosinase), mutated gene products (e.g., beta catenin), oncogenes (e.g., Her2/neu), and a collection of immunogenic proteins that have an expression pattern restricted to testis, as well as a proportion of various cancers. These proteins, referred to as cancer-testis antigens (CT antigens, CTAs), were initially identified in cancer patients by expression cloning using either the autologous cellular or humoral immune response as the election criteria. The first members of this group were those molecules defined by cytotoxic T-lymphocyte (CTL) recognition such as the MAGE, BAGE, and GAGE antigens. Subsequently, by employing autologous antibody recognition, the SEREX (serological analysis of recombinant cDNA expression libraries) method uncovered other members of this group including the HOM-MEL-40/SSX2, NY-ESO-1, SCP1 and CT7 antigens.

The SEREX procedure was described by Sahin et al. (*Proc. Natl. Acad. Sci. USA* 92:11810–11813, 1995). Also, see U.S. Pat. No. 5,698,396, incorporated herein by reference. According to this approach, autologous antisera are used to identify immunogenic protein antigens expressed in cancer cells by screening expression libraries constructed from tumor cell cDNA. Antigen-encoding clones so identified have been found to have elicited an high-titer humoral immune response in the patients from which the antisera were obtained. Such a high-titer IgG response implies helper T cell recognition of the detected antigen. These tumor antigens can then be screened for the presence of MHC/HLA class I and class II motifs and reactivity with CTLs.

More recently, non-immunological techniques such as representational difference analysis (RDA) have led to the identification of molecules such as MAGE-C1 that has an expression profile similar to CT antigens. A standardized nomenclature has been proposed for organizing the CT antigens into families. Due to a general lack of functional information, it is based on their order of discovery, i.e., sequentially, MAGE, BAGE, GAGE, HOM-MEL-40/SSX2, NY-ESO-1, SCP-1, CT7 and CT8.

Since individual CTAs are expressed only in a variable proportion of tumors of a given entity, the availability of additional CTAs would significantly enlarge the proportion of patients who are potentially eligible for therapeutic interventions. Despite the fact that the pool of available tumor antigens has grown since the introduction of SEREX, the proportion of antigen-negative tumors is still high. Thus there presently is a need for additional cancer antigens for development of therapeutics and diagnostics applicable to a greater number of cancer patients having various cancers.

SUMMARY OF THE INVENTION

The invention provides, inter alia, isolated nucleic acid molecules, expression vectors containing those molecules and host cells transfected with those molecules. The invention also provides isolated proteins and peptides, antibodies to those proteins and peptides and CTLs which recognize the proteins and peptides. Fragments including functional fragments and variants of the foregoing also are provided. Kits containing the foregoing molecules additionally are provided. The foregoing can be used in the diagnosis, monitoring, research, or treatment of conditions characterized by the expression of BRDT/CT9 and optionally one or more additional cancer associated antigens.

The invention involves the surprising discovery that a previously known gene, BRDT, is expressed in individuals who have cancer. In addition, the invention also includes the characterization of expression of CT antigens in individuals with lung cancer. These individuals have serum antibodies against the proteins (or fragments thereof) encoded by these genes. Thus, abnormally expressed genes are recognized by the host's immune system and therefore can form a basis for diagnosis, monitoring and therapy.

The invention involves the use of a single material, a plurality of different materials and even large panels and combinations of materials. For example, a single gene, a single protein encoded by a gene, a single functional fragment thereof, a single antibody thereto, etc. can be used in methods and products of the invention. Likewise, pairs, groups and even panels of these materials and optionally other cancer associated antigen genes and/or gene products can be used for diagnosis, monitoring and therapy. The pairs, groups or panels can involve 2, 3, 4, 5 or more genes, gene products, fragments thereof or agents that recognize such materials. A plurality of such materials are not only useful in monitoring, typing, characterizing and diagnosing cells abnormally expressing such genes, but a plurality of such materials can be used therapeutically. An example of this is the use of a plurality of such materials prophylactically or acutely for the prevention, delay of onset, amelioration, etc.

of cancer in cells which express or will express such genes. Any and all combinations of the genes, gene products, and materials which recognize the genes and gene products can be tested and identified for use according to the invention. It would be far too lengthy to recite all such combinations; those skilled in the art, particularly in view of the teaching contained herein, will readily be able to determine which combinations are most appropriate for which circumstances.

As will be clear from the following discussion, the invention has in vivo and in vitro uses, including for therapeutic, diagnostic, monitoring and research purposes. One aspect of the invention is the ability to fingerprint a cell expressing a number of the genes identified according to the invention by, for example, quantifying the expression of such gene products. Such fingerprints will be characteristic, for example, of the stage of the cancer, the type of the cancer, or even the effect in animal models of a therapy on a cancer. Cells also can be screened to determine whether such cells abnormally express the genes identified according to the invention.

The invention, in part, relates to compositions and methods of use thereof of nucleic acid molecules and polypeptides. For simplicity, these nucleic acid molecules and polypeptides have been classified into different groups. NA Group 1 molecules represent (a) nucleic acid molecules coding for a cancer associated antigen precursor and which hybridize under stringent conditions to a molecule consisting of the nucleotide sequence of SEQ ID NO:4, (b) deletions, additions and substitutions which code for a respective cancer associated antigen precursor, and (c) complements of (a) or (b). NA Group 2 molecules represent fragments of NA Group 1 molecules which code for a polypeptide which, or a portion of which, binds an MHC molecule to form a complex recognized by a an autologous antibody or lymphocyte. NA Group 3 molecules represent (a) nucleic acid molecules which code for a cancer associated antigen precursor and which hybridize under stringent conditions to a molecule consisting of a nucleic acid sequence selected from the group consisting of nucleic acid sequences among SEQ ID Nos:13–19, (b) deletions, additions and substitutions which code for a respective cancer associated antigen precursor, (c) complements of (a) or (b). NA Group 4 molecules represent fragments of NA Group 3 molecules which code for a polypeptide which, or a portion of which, binds to an MHC molecule to form a complex recognized by an autologous antibody or lymphocyte. PP Group 1 polypeptides are polypeptides encoded by NA Group 1 molecules. PP Group 2 polypeptides are polypeptides encoded by NA Group 2 molecules. PP Group 3 polypeptides are polypeptides encoded by NA Group 3 molecules. PP Group 4 polypeptides are polypeptides encoded by NA Group 4 molecules. As used herein, nucleic acid molecules and polypeptides will be referred to by group. Where appropriate and stated, degenerate sequences of nucleic acid molecules are also embraced by the invention. Degenerate sequences or degenerates refer to nucleic acid molecules that differ from a nucleic acid molecule in codon sequence due to the degeneracy of the genetic code.

The invention, in one aspect, is a method of diagnosing a disorder characterized by expression of a preferably human cancer associated antigen precursor coded for by at least one nucleic acid molecule. The method involves the steps of contacting a biological sample isolated from a subject with an agent that specifically binds to a first nucleic acid molecule, a fragment of a first nucleic acid molecule, an expression product of a first nucleic acid molecule, or a fragment of an expression product of a first nucleic acid molecule complexed with an MHC, preferably an HLA, molecule, wherein the nucleic acid molecule is a NA Group 1 nucleic acid molecule, and determining the interaction between the agent and the first nucleic acid molecule, the fragment of the first nucleic acid molecule, the expression product or fragment of the expression product of the first nucleic acid molecule as a determination of the disorder.

In one embodiment, the agent is selected from the group consisting of (a) a nucleic acid molecule comprising a complement of the first nucleic acid molecule or a fragment thereof, (b) an antibody that binds to an expression product, or a fragment thereof, of the first nucleic acid molecule, and (c) an agent that binds to a complex of an MHC, preferably HLA, molecule and a fragment of an expression product of the first nucleic acid.

In another embodiment, the method further comprises the use of a second agent that specifically binds to a second nucleic acid molecule, a fragment of the second nucleic acid molecule, an expression product of the second nucleic acid molecule, or a fragment of the expression product of the second nucleic acid molecule complexed with an HLA molecule, wherein the second nucleic acid molecule is a NA Group 3 molecule. The method further involves determining the interaction between the second agent and the second nucleic acid molecule, the fragment of the second nucleic acid molecule, the expression product or fragment of the expression product of the second nucleic acid molecule as a determination of the disorder.

In a further embodiment, the second agent is selected from the group consisting of (a) a nucleic acid molecule comprising a complement of the second nucleic acid molecule or a fragment thereof, (b) an antibody that binds to an expression product, or a fragment thereof, of the second nucleic acid molecule, and (c) agent that binds to a complex of an MHC, preferably HLA, molecule and a fragment of an expression product of the second nucleic acid.

The disorder may be characterized by expression of a plurality of cancer associated antigen precursors. Thus the methods of diagnosis may include use of a plurality of agents, each of which is specific for a human cancer associated antigen precursor (including at least one of the cancer associated antigen precursors disclosed herein). The second nucleic acid molecule may be a plurality of different second nucleic acid molecules and the second agent may be a plurality of second agents each of which bind to a respective second nucleic acid molecule, a fragment of a respective second nucleic acid molecule, an expression product of a respective second nucleic acid molecule or a fragment of an expression product of a respective second nucleic acid molecule complexed with an HLA molecule. The plurality of agents may be at least 2, at least 3, at least 4, at least 5, at least 6 or at least 7.

In another aspect the invention is a method for determining regression, progression or onset of a condition characterized by expression of abnormal levels of at least one protein. The method involves the steps of monitoring a sample, from a subject who has or is suspected of having the condition, for a parameter selected from the group consisting of (i) a first protein encoded by a nucleic acid molecule which comprises a NA Group 1 molecule, (ii) a first peptide derived from the first protein, (iii) an antibody which selectively binds the first protein or the first peptide, and (iv) cytolytic T cells specific for a complex of the first peptide derived from the first protein and an MHC molecule, as a determination of regression, progression or onset of said condition. In one embodiment the sample is a body fluid, a body effusion or a tissue.

In another embodiment the step of monitoring comprises contacting the sample with a detectable agent selected from the group consisting of (a) an antibody which selectively binds the first protein of (i), or the first peptide of (ii), (b) a protein or a peptide which binds the antibody of (iii), and (c) a cell which presents the complex of the first peptide and MHC molecule of (iv). In a preferred embodiment the antibody, the first protein, the first peptide or the cell is labeled with a detectable molecule, such as a radioactive label or an enzyme. The sample in a preferred embodiment is assayed for the first peptide.

According to another embodiment the protein is a plurality of proteins, at least one of the plurality being encoded by a second nucleic acid molecule comprising a NA Group 3 molecule and the at least one of the plurality is at least 1, at least 2, at least 3, at least 4, at least 5, at least 6, or at least 7. In yet another embodiment, the parameter is a plurality of parameters, each of the plurality of parameters respective for one plurality of proteins.

The invention in another aspect is a pharmaceutical composition for a human subject. The pharmaceutical preparation includes an effective amount of an agent which when administered to the subject enriches selectively the presence of complexes of an HLA molecule and a human cancer associated antigen, and a pharmaceutically acceptable carrier, wherein the human cancer associated antigen is a fragment of a human cancer associated antigen precursor encoded by a nucleic acid molecule which comprises a NA Group 1 molecule. In one embodiment the nucleic acid molecule is a NA Group 3 molecule.

The agent in another embodiment comprises a plurality of agents, each of which enriches selectively in the subject complexes of an HLA molecule and a different human cancer associated antigen. Preferably the plurality is at least 2, at least 3, at least 4, at least 5, at least 6 or at least 7 different such agents, and at least one of the different human cancer associated antigens is encoded by a NA Group 3 molecule.

In another embodiment the agent is selected from the group consisting of (1) an isolated polypeptide comprising the human cancer associated antigen, or a functional variant thereof, (2) an isolated nucleic acid operably linked to a promoter for expressing the isolated polypeptide, or functional variant thereof, (3) a host cell expressing the isolated polypeptide, or functional variant thereof, and (4) isolated complexes of the polypeptide, or functional variants thereof, and an HLA molecule.

The agent may be a cell expressing an isolated polypeptide. In one embodiment the agent is a cell expressing an isolated polypeptide comprising the human cancer associated antigen or a functional variant thereof. In another embodiment the agent is a cell expressing an isolated polypeptide comprising the human cancer associated antigen or a functional variant thereof, and wherein the cell expresses an HLA molecule that binds the polypeptide. The cell can express one or both of the polypeptide and HLA molecule recombinantly. In preferred embodiments the cell is nonproliferative. In yet another embodiment the agent is a plurality of agents, and the plurality is at least 2, at least 3, at least 4, at least 5, at least 6, or at least 7 different polypeptides, each representing a different human cancer associated antigen or functional variant thereof.

The agent in one embodiment is a PP Group 1 polypeptide. In another embodiment, the agent is a PP Group 2 polypeptide. In yet other embodiments, the agent is a PP Group 3 polypeptide or a PP Group 4 polypeptide.

In an embodiment each of the pharmaceutical compositions described herein also includes an adjuvant.

According to another aspect the invention, a composition of matter is provided which includes an isolated agent that binds selectively to a PP Group 1 polypeptide. In separate embodiments the agent binds selectively to a polypeptide selected from the following: a PP Group 2 polypeptide, a PP Group 3 polypeptide and a PP Group 4 polypeptide. In other embodiments, the agent is a plurality of different agents that bind selectively at least 2, at least 3, at least 4, at least 5, at least 6 or at least 7 different such polypeptides. In each of the above described embodiments the agent may be an antibody. In a further embodiment, the agent is a therapeutic or a diagnostic agent.

In another aspect the invention is a composition of matter comprising a conjugate of the agent of the above-described compositions of the invention and a therapeutic or diagnostic agent. Preferably the conjugate is of the agent and a therapeutic or diagnostic agent that is a toxin.

In another aspect of the invention, pharmaceutical compositions are provided each comprising an effective amount of any one of the compositions of matter described above and a pharmaceutically acceptable carrier.

The invention in another aspect is a pharmaceutical composition comprising an effective amount of an isolated nucleic acid molecule selected from the group consisting of: (1) NA Group 1 molecules, (2) NA Group 2 molecules, and (3) degenerates of NA Group 1 and NA Group 2 molecules, and a pharmaceutically acceptable carrier. In one embodiment the composition further comprises at least two isolated nucleic acid molecules coding for two different polypeptides, each polypeptide comprising a different human cancer associated antigen, wherein at least one of the nucleic acid molecules is selected from the group consisting of a NA Group 3 molecule and a NA Group 4 molecule.

Preferably the pharmaceutical composition also includes an expression vector with a promoter operably linked to the isolated nucleic acid molecule. In another embodiment the pharmaceutical composition also includes a host cell recombinantly expressing the isolated nucleic acid molecule.

According to another aspect of the invention a pharmaceutical composition is provided that includes an effective amount of an isolated polypeptide comprising a PP Group 1 or a PP Group 2 polypeptide, and a pharmaceutically acceptable carrier. In one embodiment the isolated polypeptide further comprises a PP Group 3 or a PP Group 4 polypeptide.

In another embodiment the isolated polypeptide comprises at least two different polypeptides, each comprising a different preferably human cancer associated antigen. In separate embodiments the isolated polypeptides are selected from PP Group 3 polypeptides or HLA binding fragments thereof.

In an embodiment each of the pharmaceutical compositions described herein also includes an adjuvant.

Another aspect of the invention is an isolated nucleic acid molecule comprising a NA Group 3 molecule. Another aspect the invention is an isolated nucleic acid molecule comprising a NA Group 4 molecule.

According to another aspect of the invention isolated polypeptides encoded by the isolated nucleic acid molecules of the invention, described above, are provided. These include PP Group 1–4 polypeptides. In a preferred embodiment, a fragment of a PP Group 1 polypeptide is provided. The invention also includes a fragment of the polypeptide which is immunogenic. In one embodiment the fragment, or a portion of the fragment, binds HLA molecule or a human antibody.

The invention includes in another aspect an isolated fragment of a human cancer associated antigen precursor which, or portion of which, binds an HLA molecule or a human antibody, wherein the precursor is encoded by a nucleic acid molecule comprising a NA Group 1 molecule. In one embodiment the fragment is part of a complex with an HLA molecule. In another embodiment the fragment is between 8 and 12 amino acids in length. In another embodiment the invention includes an isolated polypeptide comprising a fragment of the polypeptide of sufficient length to represent a sequence unique within the human genome and identifying a polypeptide that is a human cancer associated antigen precursor.

According to another aspect of the invention a method for treating a subject with a disorder characterized by expression of a human cancer associated antigen precursor is provided. The method includes the step of administering to the subject an amount of an agent, which enriches selectively in the subject the presence of complexes of an HLA molecule and a human cancer associated antigen, effective to ameliorate the disorder, wherein the human cancer associated antigen is a fragment of a human cancer associated antigen precursor encoded by a nucleic acid molecule comprising a NA group 1 nucleic acid molecule.

In one embodiment the disorder is characterized by expression of a plurality of human cancer associated antigen precursors and the agent is a plurality of agents, each of which enriches selectively in the subject the presence of complexes of an HLA molecule and a different human cancer associated antigen wherein at least one of the human cancer associated antigens is encoded by a NA Group 3 molecule. Preferably the plurality is at least 2, at least 3, at least 4, at least 5, at least 6 or at least 7 such agents.

In another embodiment the agent is an isolated polypeptide selected from the group consisting of PP Group 1, PP Group 2, PP Group 3, and PP Group 4 polypeptides.

In yet another embodiment the disorder is cancer. In preferred embodiments, the disorder is lung cancer.

According to another aspect the invention is a method for treating a subject having a condition characterized by expression of at least one human cancer associated antigen precursor in cells of the subject. The method includes the steps of (i) removing an immunoreactive cell containing sample from the subject, (ii) contacting the immunoreactive cell containing sample to a host cell under conditions favoring production of cytolytic T cells against a human cancer associated antigen which is a fragment of the precursor, (iii) introducing the cytolytic T cells to the subject in an amount effective to lyse cells which express the human cancer associated antigen, wherein the host cell is transformed or transfected with an expression vector comprising an isolated nucleic acid molecule, or human cancer associated antiagen encoding fragment thereof, operably linked to a promoter. The isolated nucleic acid molecule is selected from the group of nucleic acid molecules consisting of NA Group 1, NA Group 2, NA Group 3, and NA Group 4 nucleic acid molecules. In preferred embodiments, the isolated nucleic acid molecule is a NA Group 1 nucleic acid molecule.

In one embodiment the host cell recombinantly expresses an HLA molecule which binds the human cancer associated antigen. In another embodiment the host cell endogenously expresses an HLA molecule which binds the human cancer associated antigen.

The invention includes in another aspect a method for treating a subject having a condition characterized by expression of at least one cancer associated antigen precursor in cells of the subject. The method includes the steps of (i) identifying a nucleic acid molecule expressed by the cells associated with said condition, wherein said nucleic acid molecule is a NA Group 1 molecule (ii) transfecting a host cell with a nucleic acid selected from the group consisting of (a) the nucleic acid molecule identified, (b) a fragment of the nucleic acid identified which includes a segment coding for a cancer associated antigen, (c) deletions, substitutions or additions to (a) or (b), and (d) degenerates of (a), (b), or (c); (iii) culturing said transfected host cells to express the transfected nucleic acid molecule, and; (iv) introducing an amount of said host cells or an extract thereof to the subject effective to increase an immune response against the cells of the subject associated with the condition. Preferably, the antigen is a human antigen and the subject is a human.

In one embodiment the method also includes the step of (a) identifying an MHC molecule which presents a portion of an expression product of the nucleic acid molecule, wherein the host cell expresses the same MHC molecule as identified in (a) and wherein the host cell presents an MHC binding portion of the expression product of the nucleic acid molecule.

In another embodiment the method also includes the step of treating the host cells to render them non-proliferative.

In yet another embodiment the immune response comprises a B-cell response or a T cell response. Preferably the response is a T-cell response which comprises generation of cytolytic T-cells specific for the host cells presenting the portion of the expression product of the nucleic acid molecule or cells of the subject expressing the human cancer associated antigen.

In another embodiment the method comprises identifying a second nucleic acid molecule expressed by the cells associated with the condition, wherein the second nucleic acid molecule comprises a NA Group 3 molecule.

Another aspect of the invention is a method for treating or diagnosing or monitoring a subject having a condition characterized by expression of an abnormal amount of a protein encoded by a nucleic acid molecule that is a NA Group 1 molecule. The method includes the step of administering to the subject an antibody or an agent which specifically binds to the protein or a peptide derived therefrom, the antibody optimally being coupled to a therapeutically useful agent, in an amount effective to treat the condition.

In one embodiment the antibody is a monoclonal antibody. Preferably the monoclonal antibody is a chimeric antibody or a humanized antibody.

In another aspect the invention is a method for treating a condition characterized by expression in a subject of abnormal amounts of a protein encoded by a nucleic acid molecule comprising a NA Group 1 molecule. The method involves the step of administering to a subject at least one of the pharmaceutical compositions of the invention described above in an amount effective to prevent, delay the onset of, or inhibit the condition in the subject. In one embodiment the condition is cancer. In another embodiment the method includes the step of first identifying that the subject expresses in a tissue abnormal amounts of the protein.

The invention in another aspect is a method for treating a subject having a condition characterized by expression of abnormal amounts of a protein encoded by a nucleic acid molecule that is a NA Group 1 nucleic acid molecule. The method includes the steps of (i) identifying cells from the subject which express abnormal amounts of the protein; (ii) isolating a sample of the cells; (iii) cultivating the cells, and (iv) introducing the cells to the subject in an amount effective to provoke an immune response against the cells.

In one embodiment the method includes the step of rendering the cells non-proliferative, prior to introducing them to the subject.

In another aspect the invention is a method for treating a pathological condition characterized by aberrant expression of a protein encoded by a nucleic acid molecule comprising a NA Group 1 molecule. The method includes the step of administering to a subject in need thereof an effective amount of an agent which inhibits the expression or activity of the protein.

In one embodiment the agent is an inhibiting antibody which selectively binds to the protein and wherein the antibody is a monoclonal antibody, a chimeric antibody, a humanized antibody or a fragment thereof. In another embodiment the agent is an antisense nucleic acid molecule which selectively binds to the nucleic acid molecule which encodes the protein. In yet another important embodiment the nucleic acid molecule further comprises a NA Group 3 molecule.

The invention includes in another aspect a composition of matter useful in stimulating an immune response to a plurality of proteins encoded by nucleic acid molecules that are NA Group 1 and optionally NA Group 3 molecules. The composition is a plurality of peptides derived from the amino acid sequences of the proteins, wherein the peptides bind to one or more MHC molecules presented on the surface of the cells which express an abnormal amount of the protein.

In one embodiment at least a portion of the plurality of peptides bind to MHC molecules and elicit a cytolytic or antibody response thereto. In another embodiment the composition of matter includes an adjuvant and/or a costimulatory molecule. In another embodiment the adjuvant is a saponin, GM-CSF, or an interleukin. In still another embodiment, the compositions also includes at least one peptide useful in stimulating an immune response to at least one protein which is not encoded by nucleic acid molecules that are NA Group 1 molecules, wherein the at least one peptide binds to one or more MHC molecules.

According to another aspect the invention is an isolated antibody which selectively binds to a complex of: (i) a peptide derived from a protein encoded by a nucleic acid molecule that is a NA Group 1 molecule and (ii) and an MHC molecule which binds the peptide to form the complex, wherein the isolated antibody does not bind to (i) or (ii) alone.

In one embodiment the antibody is a monoclonal antibody, a chimeric antibody, a humanized antibody or a fragment thereof.

The invention also involves the use of the genes, gene products, fragments thereof, agents which bind thereto, and so on in the preparation of medicaments. A particular medicament is for treating cancer and a more particular medicament is for treating seminomas, melanomas, teratomas, gliomas, lung cancer, ovarian cancer and/or colorectal cancer.

Sequence Listing

SEQ ID NO:1 is the nucleotide sequence of human RING3 cDNA.

SEQ ID NO:2 is the nucleotide sequence of human KIAA0043 cDNA.

SEQ ID NO:3 is the nucleotide sequence of human HUNK1 cDNA.

SEQ ID NO:4 is the nucleotide sequence of human BRDT cDNA.

SEQ ID NO:5 is the nucleotide sequence of the forward primer for BRDT.

SEQ ID NO:6 is the nucleotide sequence of the reverse primer for BRDT.

SEQ ID NO:7 is the nucleotide sequence of the forward primer for RING3.

SEQ ID NO:8 is the nucleotide sequence of the reverse primer for RING3.

SEQ ID NO:9 is the nucleotide sequence of the forward primer for KIAA0043.

SEQ ID NO:10 is the nucleotide sequence of the reverse primer for KIAA0043.

SEQ ID NO:11 is the nucleotide sequence of the forward primer for HUNK1.

SEQ ID NO:12 is the nucleotide sequence of the reverse primer for HUNK1.

SEQ ID NO:13 is the nucleotide sequence of human SCP-1 cDNA.

SEQ ID NO:14 is the nucleotide sequence of human NY-ESO-1 cDNA.

SEQ ID NO:15 is the nucleotide sequence of human CT7 cDNA.

SEQ ID NO:16 is the nucleotide sequence of human SSX2 cDNA.

SEQ ID NO:17 is the nucleotide sequence of human SSX4 cDNA.

SEQ ID NO:18 is the nucleotide sequence of human MAGEA1 cDNA.

SEQ ID NO:19 is the nucleotide sequence of human MAGEA3 cDNA.

SEQ ID NO:20 is the amino acid sequence of human RING3 protein.

SEQ ID NO:21 is the amino acid sequence of human KIAA0043 protein.

SEQ ID NO:22 is the amino acid sequence of human HUNK1 protein.

SEQ ID NO:23 is the amino acid sequence of human BRDT protein.

SEQ ID NO:24 is the amino acid sequence of human SCP-1 protein.

SEQ ID NO:25 is the amino acid sequence of human NY-ESO-1 protein.

SEQ ID NO:26 is the amino acid sequence of human CT7 protein.

SEQ ID NO:27 is the amino acid sequence of human SSX2 protein.

SEQ ID NO:28 is the amino acid sequence of human SSX4 protein.

SEQ ID NO:29 is the amino acid sequence of human MAGE-A1 protein.

SEQ ID NO:30 is the amino acid sequence of human MAGE-A3 protein.

Genbank accession numbers for cDNA sequences listing above are as follows: RING3 is X96670, KIAA0043 is D26362, HUNK1 is Y12059, BRDT is AF019085, SCP-1 is D67035, NY-ESO-1 is U87459, CT7 is AF056334, SSX2 is X86175, SSX4 is U90841, MAGE-A1 is NM—004988, MAGE-3A is NM_005362.

DETAILED DESCRIPTION OF THE INVENTION

A previously identified gene, bromo domain testis-specific gene product (BRDT), has been cloned and molecularly characterized as a cancer-testis antigen (CT9). This cancer associated antigen was identified by its homology to another gene, RING3, isolated by SEREX analysis of the serum of a breast cancer patient. The potential oncogenic function of BRDT, and/or its function as a marker of cancer cells, and the function of the other cancer associated antigens can be inhibited by specific immunological and genetic therapeutic interventions.

In the above summary and in the ensuing description, lists of sequences are provided. The lists are meant to embrace each single sequence separately, two or more sequences together where they form a part of the same gene, any combination of two or more sequences which relate to different genes, including and up to the total number on the list, as if each and every combination were separately and specifically enumerated. Likewise, when mentioning fragment size, it is intended that a range embrace the smallest fragment mentioned to the full-length of the sequence (less one nucleotide or amino acid so that it is a fragment), each and every fragment length intended as if specifically enumerated. Thus, if a fragment could be between 10 and 15 in length, it is explicitly meant to mean 10, 11, 12, 13, 14, or 15 in length.

The summary and the claims mention antigen precursors and antigens. As used in the summary and in the claims, a precursor is substantially the full-length protein encoded by the coding region of the isolated DNA and the antigen is a peptide which complexes with MHC, preferably HLA, and which participates in the immune response as part of that complex. Such antigens are typically 9 amino acids long (for HLA class II molecules), although this may vary slightly.

The nucleic acid molecules described herein preferably are isolated. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

The polypeptides described herein also preferably are isolated. As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

As used herein, a subject is a human, non-human primate, cow, horse, pig, sheep, goat, dog, cat, rodent or other verterinary animal. In all embodiments human cancer antigens and human subjects are preferred.

The present invention in one aspect involves the identification of a cDNA encoding RING3 as a human cancer associated antigen precursor using autologous antisera of subjects having breast cancer. In another aspect, the invention involves the identification of a RING3 homolog, BRDT, as a cancer-testis antigen. The nature of the BRDT gene as encoding a CT antigen is, of course, unexpected.

The invention thus involves in one aspect cancer associated antigen polypeptides, genes encoding those polypeptides, functional modifications and variants of the foregoing, useful fragments of the foregoing, as well as diagnostics and therapeutics relating thereto. Preferably the cancer associated antigens are cancer-testis antigens as described herein.

Homologs and alleles of the cancer associated antigen nucleic acids of the invention can be identified by conventional techniques. Thus, an aspect of the invention is those nucleic acid sequences which code for cancer associated antigen precursors. Because this application contains several nucleotide and amino acid sequences, the following chart is provided to identify the various groups of sequences discussed in the claims and in the summary:

Nucleic Acid Sequences

NA Group 1. (a) nucleic acid molecules coding for a cancer associated antigen precursor and which hybridize under stringent conditions to a molecule consisting of the nucleotide sequence of SEQ ID NO:4, (b) deletions, additions and substitutions which code for a respective cancer associated antigen precursor, and (c) complements of (a) or (b).

NA Group 2. Fragments of NA Group 1, which code for a polypeptide which, or a portion of which, binds an MHC molecule to form a complex recognized by a an autologous antibody or lymphocyte.

NA Group 3. (a) nucleic acid molecules which code for a cancer associated antigen precursor and which hybridize under stringent conditions to a molecule consisting of a nucleic acid sequence selected from the group consisting of nucleic acid sequences among SEQ ID NOs:13–19, (b) deletions, additions and substitutions which code for a respective cancer associated antigen precursor, (c) complements of (a) or (b).

NA Group 4. Fragments of NA Group 3, which code for a polypeptide which, or a portion of which, binds to an MHC molecule to form a complex recognized by an autologous antibody or lymphocyte.

Polypeptide Sequences

PP Group 1. Polypeptides encoded by NA Group 1.
PP Group 2. Polypeptides encoded by NA Group 2
PP Group 3. Polypeptides encoded by NA Group 3.
PP Group 4. Polypeptides encoded by NA Group 4

The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1–0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of cancer associated antigen nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to the sequences of cancer associated antigen nucleic acid and polypeptides, respectively, in some instances will share at least 50% nucleotide identity and/or at least 65% amino acid identity and in still other instances will share at least 60% nucleotide identity and/or at least 75% amino acid identity. Preferably the homologs and alleles will share at least 80% nucleotide identity and/or at least 90% amino acid identity, and more preferably will share at least 90% nucleotide identity and/or at least 95% amino acid identity. The homology can be calculated using various, publicly available software tools developed by NCBI (Bethesda, Maryland) that can be obtained through the internet (ftp:/ncbi.nlm.nih.gov/pub/). Exemplary tools include the BLAST system available at http://www.ncbi.nlm.nih.gov, used with default settings. Pairwise and ClustalW alignments (BLOSUM30 matrix setting) as well as Kyte-Doolittle hydropathic analysis can be obtained, for example, using the MacVector sequence analysis software (Oxford Molecular Group). Watson-Crick complements of the foregoing nucleic acids also are embraced by the invention.

In screening for cancer associated antigen genes, a Southern blot may be performed using the foregoing conditions, together with a radioactive probe. After washing the membrane to which the DNA is finally transferred, the membrane can be placed against X-ray film to detect the radioactive signal. In screening for the expression of cancer associated antigen nucleic acids, Northern blot hybridizations using the foregoing conditions (see also the Examples) can be performed on samples taken from cancer patients or subjects suspected of having a condition characterized by expression of cancer associated antigen genes. Amplification protocols such as polymerase chain reaction using primers which hybridize to the sequences presented also can be used for detection of the cancer associated antigen genes or expression thereof.

The cancer associated genes correspond to NA Groups 1 and 3 The preferred cancer associated antigens for the methods of diagnosis disclosed herein are BRDT (SEQ ID NO:4) and previously identified cancer-testis antigens (SEQ ID NOs:13–19), each of which may be used alone or in combination. Encoded polypeptides (e.g., proteins), peptides and antisera thereto are also preferred for diagnosis.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating cancer associated antigen polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as antigenicity, enzymatic activity, receptor binding, formation of complexes by binding of peptides by MHC class I and class II molecules, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

Fragments of the cancer-testis antigen nucleic acids can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Fragments also can be used to produce fusion proteins for generating antibodies or determining binding of polypeptide fragments, or for generating immunoassay components. Likewise, fragments can be employed to produce nonfused fragments of the cancer-testis polypeptides, useful, for example, in the preparation of antibodies, and in immunoassays. Fragments further can be used as antisense molecules to inhibit the expression of cancer-testis nucleic acids and polypeptides, particularly for therapeutic purposes.

Especially preferred nucleic acid molecules include nucleic acids encoding a series of epitopes, known as "polytopes". The epitopes can be arranged in sequential or overlapping fashion (see, e.g. Thomson et al., *Proc. Natl. Acad. Sci. USA* 92:5845–5849, 1995; Gilbert et al., *Nature Biotechnol.* 15:1280–1284, 1997), with or without the natural flanking sequences, and can be separated by unrelated linker sequences if desired. The polytope is processed to generated individual epitopes which are recognized by the immune system for generation of immune responses.

Thus, for example, peptides derived from a polypeptide having an amino acid sequence encoded by one of the nucleic acid molecules disclosed herein, and which are presented by MHC molecules and recognized by CTL or T helper lymphocytes, can be combined with peptides from one or more other cancer associated antigens (e.g. by preparation of hybrid nucleic acids or polypeptides) to form "polytopes". The two or more peptides (or nucleic acids encoding the peptides) can be selected from those described herein, or they can include one or more peptides of previously known cancer associated antigens. Exemplary cancer associated peptide antigens (which are presented by MHC class I or II) that can be administered to induce or enhance an immune response are derived from tumor associated genes and encoded proteins including MAGE-A2, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-B2, MAGE-B3, MAGE-B4, tyrosinase, brain glycogen phosphorylase, Melan-A, MAGE-C1, MAGE-C2, LAGE-1, SSX-1, and SSX-5. See, for example, PCT application publication no. WO96/10577. Other examples will be known to one of ordinary skill in the art (for example, see Coulie, *Stem Cells* 13:393–403, 1995), and can be used in the invention in a like manner as those disclosed herein. One of ordinary skill in the art can prepare polypeptides comprising one or more peptides of the invention and one or more of the foregoing known cancer associated peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad Sci USA* 92(13) :5845–5849, 1995; Gilbert et al., *Nature Biolechnol.* 15(12) :1280–1284, 1997; Thomson et al., *J. Immunol.* 157(2) :822–826, 1996; Tam et al., *J. Exp. Med.* 171(1):299–306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type, for example, as described in the Examples below. Polytopes can be introduced to a patient in need of such treatment as polypeptide structures, or via the use of nucleic acid delivery systems known in the art (see, e.g., Allsopp et al., *Eur. J. Immunol.* 26(8):1951–1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

In instances in which a human HLA molecule presents tumor rejection antigens derived from cancer associated nucleic acids, the expression vector may also include a nucleic acid sequence coding for the HLA molecule that presents any particular tumor rejection antigen derived from these nucleic acids and polypeptides. Alternatively, the nucleic acid sequence coding for such a HLA molecule can be contained within a separate expression vector. In a situation where the vector contains both coding sequences, the single vector can be used to transfect a cell which does not normally express either one. Where the coding sequences for a cancer associated antigen precursor and the HLA molecule which presents it are contained on separate expression vectors, the expression vectors can be cotransfected. The cancer associated antigen precursor coding sequence may be used alone, when, e.g. the host cell already expresses a HLA molecule which presents a cancer associated antigen derived from precursor molecules. Of course, there is no limit on the particular host cell which can be used. As the vectors which contain the two coding sequences may be used in any antigen-presenting cells if desired, and the gene for cancer associated antigen precursor can be used in host cells which do not express a HLA molecule which presents a cancer associated antigen. Further, cell-free transcription systems may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or integrated in the genone in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a cancer associated antigen polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr Virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant for the expression of an antigen is disclosed by Warnier et al., in intradermal injection in mice for immunization against P1A (*Int. J. Cancer,* 67:303–310, 1996). Additional vectors for delivery of nucleic acid are provided below.

The invention also embraces so-called expression kits, which allow the artisan to prepare a desired expression vector or vectors. Such expression kits include at least separate portions of a vector and one or more of the previously discussed cancer associated antigen nucleic acid molecules. Other components may be added, as desired, as long as the previously mentioned nucleic acid molecules, which are required, are included. The invention also includes kits for amplification of a cancer associated antigen nucleic acid, including at least one pair of amplification primers which hybridize to a cancer associated antigen nucleic acid. The primers preferably are 12–32 nucleotides in length and are non-overlapping to prevent formation of "primer-dimers". One of the primers will hybridize to one strand of the cancer associated antigen nucleic acid and the second primer will hybridize to the complementary strand of the cancer associated antigen nucleic acid, in an arrangement which permits amplification of the cancer associated antigen nucleic acid. Selection of appropriate primer pairs is standard in the art. For example, the selection can be made with assistance of a computer program designed for such a purpose, optionally followed by testing the primers for amplification specificity and efficiency.

The invention also permits the construction of cancer associated antigen gene "knock-outs" and stable or transient transgenic expression in cells and in animals, providing materials for studying certain aspects of cancer and immune system responses to cancer.

As mentioned above, the invention embraces antisense oligonucleotides that selectively bind to a nucleic acid molecule encoding a cancer associated antigen polypeptide, to reduce the expression of cancer associated antigens, preferably cancer-testis antigens. This is desirable in virtually any medical condition wherein a reduction of expression of cancer associated antigens is desirable, e.g., in the treatment of cancer. This is also useful for in vitro or in vivo testing of the effects of a reduction of expression of one or more cancer associated antigens.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the sequences of nucleic acids encoding cancer associated antigen, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases.

Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although the listed sequences are cDNA sequences, one of ordinary skill in the art may easily derive the genomic DNA corresponding to the cDNA of a cancer associated antigen. Thus, the present invention also provides for antisense oligonucleotides which are complementary to the genomic DNA corresponding to nucleic acids encoding cancer associated antigens. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding cancer associated antigen polypeptides, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art, as further described below.

The invention also provides isolated polypeptides (including whole proteins and partial proteins, i.e., fragments) encoded by the foregoing cancer associated antigen nucleic acids. Such polypeptides are useful, for example, alone or as fusion proteins to generate antibodies, as components of an immunoassay or diagnostic assay or as therapeutics. Cancer associated antigen polypeptides can be isolated from biological samples including tissue or cell homogenates, and preferably are expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

Fragments of a polypeptide preferably are those fragments which retain a distinct functional capability of the polypeptide. Functional capabilities which can be retained in a fragment of a polypeptide include interaction with antibodies, interaction with other polypeptides or fragments thereof, selective binding of nucleic acids or proteins, and enzymatic actyivity. One important activity is the ability to complex with HLA and to provoke in a human an immune response.

The invention embraces variants of the cancer associated antigen polypeptides described above. As used herein, a "variant" of a cancer associated antigen polypeptide is a polypeptide which contains one or more modifications to the primary amino acid sequence of a cancer associated antigen polypeptide. Modifications which create a cancer associated antigen variant can be made to a cancer associated antigen polypeptide 1) to reduce or eliminate an activity of a cancer associated antigen polypeptide; 2) to enhance a property of a cancer associated antigen polypeptide, such as protein stability in an expression system or the stability of protein-protein binding; 3) to provide a novel activity or property to a cancer associated antigen polypeptide, such as addition of an antigenic epitope or addition of a detectable moiety; or 4) to provide equivalent or better binding to an HLA molecule. Modifications to a cancer associated antigen polypeptide are typically made to the nucleic acid which encodes the cancer associated antigen polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the cancer associated antigen amino acid sequence. One of skill in the art will be familiar with methods for predicting the effect on protein conformation of a change in protein sequence, and can thus "design" a variant cancer associated antigen polypeptide according to known methods. One example of such a method is described by Dahiyat and Mayo in Science 278:82–87, 1997, whereby proteins can be designed de novo. The method can be applied to a known protein to vary a only a portion of the polypeptide sequence. By applying the computational methods of Dahiyat and Mayo, specific variants of a cancer associated antigen polypeptide can be proposed and tested to determine whether the variant retains a desired conformation.

In general, variants include cancer associated antigen polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a cancer associated antigen polypeptide by eliminating proteolysis by proteases in an expression system (e.g., dibasic amino acid residues in yeast expression systems in which KEX2 protease activity is present).

Mutations of a nucleic acid which encode a cancer associated antigen polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant cancer associated antigen polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a cancer associated antigen gene or cDNA clone to enhance expression of the polypeptide. The activity of variants of cancer associated antigen polypeptides can be tested by cloning the gene encoding the variant cancer associated antigen polypeptide into a bacterial or mammalian expression vector, introducing the vector into an appropriate host cell, expressing the variant cancer associated antigen polypeptide, and testing for a functional capability of the cancer associated antigen polypeptides as disclosed herein. For example, the variant cancer associated antigen polypeptide can be tested for reaction with autologous or allogeneic sera as disclosed in the Examples. Preparation of other variant polypeptides may favor testing of other activities, as will be known to one of ordinary skill in the art.

The skilled artisan will also realize that conservative amino acid substitutions may be made in cancer associated antigen polypeptides to provide functional variants of the foregoing polypeptides, i.e., variants that retain the functional capabilities of the cancer associated antigen polypeptides such as stimulation of an immune response, binding to HLA molecules, etc. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functional variants of the cancer associated antigen polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, upon determining that a peptide derived from a cancer associated antigen polypeptide is presented by an MHC molecule and recognized by CTLs (e.g., in a subject or tumor type, for making polyvalent vaccines, as described in the Examples), one can make conservative amino acid substitutions to the amino acid sequence of the peptide, particularly at residues which are thought not to be direct contact points with the MHC molecule. For example, methods for identifying functional variants of HLA class II binding peptides are provided in a published PCT application of Strominger and Wucherpfennig (PCT/US96/03182). Peptides bearing one or more amino acid substitutions also can be tested for concordance with known HLA/MHC motifs prior to synthesis using, e.g. the computer program described by D'Amaro and Drijfhout (D'Amaro et al., *Human Immunol.* 43:13–18, 1995; Drijfhout et al., *Human Immunol.* 43:1–12, 1995). The substituted peptides can then be tested for binding to the MHC molecule and recognition by CTLs when bound to MHC. These variants can be tested for improved stability and are useful, inter alia, in vaccine compositions.

Conservative amino-acid substitutions in the amino acid sequence of cancer associated antigen polypeptides to produce functional variants of cancer associated antigen polypeptides typically are made by alteration of a nucleic acid encoding a cancer associated antigen polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad Sci. U.S.A.* 82: 488–492, 1985), or by chemical synthesis of a gene encoding a cancer associated antigen polypeptide. Where amino acid substitutions are made to a small unique fragment of a cancer associated antigen polypeptide, such as an antigenic epitope recognized by autologous or allogeneic sera or cytolytic T lymphocytes, the substitutions can be made by directly synthesizing the peptide. The activity of functionally equivalent fragments of cancer associated antigen polypeptides can be tested by cloning the gene encoding the altered cancer associated antigen polypeptide into a bacterial or mammalian expression vector, introducing the vector into an appropriate host cell, expressing the altered cancer associated antigen polypeptide, and testing for a functional capability of the cancer associated antigen polypeptides as disclosed herein. Peptides which are chemically synthesized can be tested directly for function, e.g., for binding to antisera recognizing associated antigens.

The invention as described herein has a number of uses, some of which are described elsewhere herein. First, the invention permits treatment of disorders characterized by expression of the cancer associated antigen nucleic acid or protein molecules, preferably by stimulation of an immune response which recognizes fragments of the polypeptides presented by HLA molecules. A variety of methodologies well-known to the skilled practitioner can be utilized to stimulate our immune response against the cancer associated antigen molecules. Immunological recognition can be stimulated by administering to a subject the cancer associated antigen polypeptides or fragments thereof. Alternatively, an expression vector may be introduced into cells to cause production of the polypeptide. Those skilled in the art also can readily follow known methods for isolating cancer associated antigen polypeptides. These include, but are not limited to, immunochromatography, HPLC, size-exclusion chromatography, ion-exchange chromatography and immune-affinity chromatography.

The isolation and identification of cancer associated antigen genes also makes it possible for the artisan to diagnose a disorder characterized by expression of cancer associated antigens. These methods involve determining expression of one or more cancer associated antigen nucleic acids, and/or encoded cancer associated antigen polypeptides and/or peptides derived therefrom. In the former situation, such determinations can be carried out via any standard nucleic acid determination assay, including the polymerase chain reaction, or assaying with labeled hybridization probes. In the latter situation, such determinations can be carried out by screening patient antisera for recognition of the polypeptide.

The invention also involves agents such as polypeptides which bind to cancer associated antigen polypeptides. Such binding agents can be used, for example, in screening assays to detect the presence or absence of cancer associated antigen polypeptides and complexes of cancer associated antigen polypeptides and their binding partners and in purification protocols to isolated cancer associated antigen polypeptides and complexes of cancer associated antigen polypeptides and their binding partners. Such agents also can be used to inhibit the native activity of the cancer associated antigen polypeptides, for example, by binding to such polypeptides.

The invention, therefore, embraces peptide binding agents which, for example, can be antibodies or fragments of antibodies having the ability to selectively bind to cancer associated antigen polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, 1. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205.

Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to cancer associated antigen polypeptides, and complexes of both cancer associated antigen polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the cancer associated antigen polypeptide. This process can be repeated through several cycles of reselection of phage that bind to the cancer associated antigen polypeptide. Repeated rounds lead to enrichment of phage bearing particular sequences. DNA sequence analysis can be conducted to identify the sequences of the expressed polypeptides. The minimal linear portion of the sequence that binds to the cancer associated antigen polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the cancer associated antigen polypeptides. Thus, the cancer associated antigen polypeptides of the invention, or a fragment thereof, can be used to screen peptide libraries, including phage display libraries, to identify and select peptide binding partners of the cancer associated antigen polypeptides of the invention. Such molecules can be used, as described, for screening assays, for purification protocols, for interfering directly with the functioning of cancer associated antigen and for other purposes that will be apparent to those of ordinary skill in the art.

As detailed herein, the foregoing antibodies and other binding molecules may be used for example to identify tissues expressing protein or to purify protein. Antibodies also may be coupled to specific diagnostic labeling agents for imaging of cells and tissues that express cancer associated antigens or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. Other diagnostic agents useful in the invention will be apparent to one of ordinary skill in the art. As used herein, "therapeutically useful agents" include any therapeutic molecule which desirably is targeted selectively to a cell expressing one of the cancer antigens disclosed herein, including antineoplastic agents, radioiodinated compounds, toxins, other cytostatic or cytolytic drugs, and so forth. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202–1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or Pseudomonas exotoxin. Toxin moieties can also be high energy-emitting radionuclides such as cobalt-60.

In the foregoing methods, antibodies prepared according to the invention also preferably are specific for the cancer associated antigen/MHC complexes described herein.

When "disorder" is used herein, it refers to any pathological condition where the cancer associated antigens are expressed. An example of such a disorder is cancer, with lung cancers as particular examples.

Samples of tissue and/or cells for use in the various methods described herein can be obtained through standard methods such as tissue biopsy, including punch biopsy and cell scraping, and collection of blood or other bodily fluids by aspiration or other methods.

In certain embodiments of the invention, an immunoreactive cell sample is removed from a subject. By "immunoreactive cell" is meant a cell which can mature into an immune cell (such as a B cell, a helper T cell, or a cytolytic T cell) upon appropriate stimulation. Thus immunoreactive cells include CD34$^+$ hematopoietic stem cells, immature T cells and immature B cells. When it is desired to produce cytolytic T cells which recognize a cancer associated antigen, the immunoreactive cell is contacted with a cell which expresses a cancer associated antigen under conditions favoring production, differentiation and/or selection of cytolytic T cells; the differentiation of the T cell precursor into a cytolytic T cell upon exposure to antigen is similar to clonal selection of the immune system.

Some therapeutic approaches based upon the disclosure are premised on a response by a subject's immune system, leading to lysis of antigen presenting cells, such as cancer cells which present one or more cancer associated antigens. One such approach is the administration of autologous CTLs specific to a cancer associated antigen/MHC complex to a subject with abnormal cells of the phenotype at issue. It is within the ability of one of ordinary skill in the art to develop such CTLs in vitro. An example of a method for T cell differentiation is presented in International Application number PCT/US96/05607. Generally, sample of cells taken from a subject, such as blood cells, are contacted with a cell presenting he complex and capable of provoking CTLs to proliferate (e.g., dendritic cells). The target ell, such as a dendritic cell, can be a transfectant. These transfectants present the desired complex on their surface and, when combined with a CTL of interest, stimulate its proliferation. Other suitable host cells, such as COS cells, are widely available. Specific production of CTL clones is well known in the art. The clonally expanded autologous CTLs then are administered to the subject.

Another method for selecting antigen-specific CTL clones has recently been described (Altman et al., *Science* 274:94–96, 1996; Dunbar et al., *Curr. Biol.* 8:413–416, 1998), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein.

To detail a therapeutic methodology, referred to as adoptive transfer (Greenberg, *J. Immunol.* 136(5): 1917, 1986; Riddel et al., *Science* 257: 238, 1992; Lynch et al, *Eur. J Immunol.* 21: 1403–1410,1991; Kast et al., *Cell* 59: 603–614, 1989), cells presenting the desired complex (e.g., dendritic cells) are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/cancer associated antigen complex. This can be determined very easily, as the art is very familiar with methods for identifying cells which present a particular HLA molecule, as well as how to identify cells expressing DNA of the pertinent sequences, in this case a cancer associated antigen sequence, particularly the CT antigens described herein. Once cells presenting the relevant complex are identified via the foregoing screening methodology, they can be combined with a sample from a patient, where the sample contains CTLs. If the complex presenting cells are lysed by the mixed CTL sample, then it can be assumed that a cancer associated antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex (i.e. the antigenic peptide and the presenting HLA molecule). Chen et al. (*Proc. Natl. Acad Sci. USA* 88: 110–114,1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. For example, nucleic acids which encode a cancer associated antigen polypeptide or peptide may be operably linked to promoter and enhancer sequences which direct expression of the cancer associated antigen polypeptide or peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding cancer associated antigen, as described elsewhere herein. Nucleic acids encoding a cancer associated antigen also may be inserted into a retroviral genome, thereby facilitating integration of the nucleic acid into the genome of the target tissue or cell type. In these systems, the gene of interest is carried by a microorganism, e.g., a Vaccinia virus, pox virus, herpes simplex virus, retrovirus or adenovirus, and the materials de facto "infect" host cells. The cells which result present the complex of interest, and are recognized by autologous CTLs, which then proliferate.

A similar effect can be achieved by combining the cancer associated antigen or a stimulatory fragment thereof with an adjuvant to facilitate incorporation into antigen presenting cells in vivo. The cancer associated antigen polypeptide is processed to yield the peptide partner of the HLA molecule while a cancer associated antigen peptide may be presented without the need for further processing. Generally, subjects can receive an intradermal injection of an effective amount of the cancer associated antigen. Initial doses can be followed by booster doses, following immunization protocols standard in the art. Preferred cancer associated antigens include those found to react with allogeneic cancer antisera, shown in the examples below.

The invention involves the use of various materials disclosed herein to "immunize" subjects or as "vaccines". As used herein, "immunization" or "vaccination" means increasing or activating an immune response against an antigen. It does not require elimination or eradication of a condition but rather contemplates the clinically favorable enhancement of an immune response toward an antigen. Generally accepted animal models can be used for testing of immunization against cancer using a cancer associated antigen nucleic acid. For example, human cancer cells can be introduced into a mouse to create a tumor, and one or more cancer associated antigen nucleic acids can be delivered by the methods described herein. The effect on the cancer cells (e.g., reduction of tumor size) can be assessed as a measure of the effectiveness of the cancer associated antigen nucleic acid immunization. Of course, testing of the foregoing animal model using more conventional methods for immunization include the administration of one or more cancer associated antigen polypeptides or peptides derived therefrom, optionally combined with one or more adjuvants and/or cytokines to boost the immune response. Methods for immunization, including formulation of a vaccine composition and selection of doses, route of administration and the schedule of administration (e.g. primary and one or more booster doses), are well known in the art. The tests also can be performed in humans, where the end point is to test for the presence of enhanced levels of circulating CTLs against cells bearing the antigen, to test for levels of circulating antibodies against the antigen, to test for the presence of cells expressing the antigen and so forth.

As part of the immunization compositions, one or more cancer associated antigens or stimulatory fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., *Mol. Cells* 7:178–186, 1997); incomplete Freund's adjuvant; complete Freund's adjuvant; montanide; and various water-in-oil emulsions prepared from biodegradable oils such as squalene and/or tocopherol. Preferably, the peptides are administered and mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 μg to about 100 μg. Other adjuvants are known in the art and can be used in the invention (see, e.g. *Goding, Monoclonal Antibodies: Principles and Practice*, 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432–1434, 1995), GM-CSF and IL-18. Thus cytokines can be administered in conjunction with antigens and adjuvants to increase the immune response to the antigens.

There are a number of immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng P., et al. *Proc. Natl. Acad. Sci. USA* 95 (11): 6284–6289 (1998)).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol*, 154:5637–5648 (1995)). Tumor cell transfection with B7 has been discussed in relation to in vitro CTL expansion for adoptive transfer immunotherapy by Wang et al., (*J. Immunol.*, 19:1–8 (1986)). Other delivery mechanisms for the B7 molecule would include nucleic acid (naked DNA) immunization (Kim J., et al. *Nat Biotechnol.*, 15:7:641–646 (1997)) and recombinant viruses such as adeno and pox (Wendtner et al., *Gene Ther.*, 4:7:726–735 (1997)). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-1COS antibodies (Hutloff et al., *Nature* 397:263–266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637–642 (1997), Fenton et al., *J. Immunother.*, 21:2:95–108 (1998)).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., *J. Immunother.*, 21:2:95–108 (1998)). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature*, 393:474 (1998), Bennett et al., *Nature*, 393:478 (1998), Schoenberger et al., *Nature*, 393:480 (1998)). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly would be expected to enhance a response to tumor antigens which are normally encountered outside of a inflammatory context or are presented by non-professional APCs (tumor cells). In these situations Th help and B7 costimulation signals are not provided. This mechanism might be used in the context of antigen pulsed DC based therapies or in situations where Th epitopes have not been defined within known TRA precursors. Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art.

A cancer associated antigen polypeptide, or a fragment thereof, also can be used to isolate their native binding partners. Isolation of such binding partners may be performed according to well-known methods. For example, isolated cancer associated antigen polypeptides can be attached to a substrate (e.g., chromatographic media, such as polystyrene beads, or a filter), and then a solution suspected of containing the binding partner may be applied to the substrate. If a binding partner which can interact with cancer associated antigen polypeptides is present in the solution, then it will bind to the substrate-bound cancer associated antigen polypeptide. The binding partner then may be isolated.

It will also be recognized that the invention embraces the use of the cancer associated antigen cDNA sequences in expression vectors, as well as to transfect host cells and cell lines, be these prokaryotic (e.g., *E. coli*), or eukaryotic (e.g., dendritic cells, B cells, CHO cells, COS cells, yeast expression systems and recombinant baculovirus expression in insect cells). Especially useful are mammalian cells such as human, mouse, hamster, pig, goat, primate, etc. They may be of a wide variety of tissue types, and include primary cells and cell lines. Specific examples include dendritic cells, keratinocytes, peripheral blood leukocytes, bone marrow stem cells and embryonic stem cells. The expression vectors require that the pertinent sequence, i.e., those nucleic acids described supra, be operably linked to a promoter.

The invention also contemplates delivery of nucleic acids, polypeptides or peptides for vaccination. Delivery of polypeptides and peptides can be accomplished according to standard vaccination protocols which are well known in the art. In another embodiment, the delivery of nucleic acid is accomplished by ex vivo methods, i.e. by removing a cell from a subject, genetically engineering the cell to include a cancer associated antigen, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo nucleic acid delivery using vectors such as viruses and targeted liposomes also is contemplated according to the invention.

In preferred embodiments, a virus vector for delivering a nucleic acid encoding a cancer associated antigen is selected from the group consisting of adenoviruses, adeno-associated viruses, poxviruses including vaccinia viruses and attenuated poxviruses, Semliki Forest virus, Venzuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220–227, 1996; Eloit et al., *J. Virol.* 7:5375–5381, 1997; Chengalvala et al., *Vaccine* 15:335–339, 1997), a modified retrovirus (Townsend et al., *J. Virol.* 71:3365–3374, 1997), a nonreplicating retrovirus (Irwin et al., *J. Virol.* 68:5036–5044, 1994), a replication defective Semliki Forest virus (Zhao et al., *Proc. Natl. Acad. Sci. USA* 92:3009–3013, 1995), canarypox virus and highly attenuated vaccinia virus derivative (Paoletti, *Proc. Natl. Acad. Sci. USA* 93:11349–11353, 1996), non-replicative vaccinia virus (Moss, *Proc. Natl. Acad. Sci. USA* 93:11341–11348, 1996), replicative vaccinia virus (Moss, *Dev. Biol. Stand.* 82:55–63, 1994), Venzuelan equine encephalitis virus (Davis et al., *J. Virol.* 70:3781–3787, 1996), Sindbis virus (Pugachev et al., *Virology* 212:587–594, 1995), and Ty virus-like particle (Allsopp et al., *Eur. J. Immunol* 26:1951–1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Cliffton, N.J. (1991).

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids of the invention into cells, depending on whether the nucleic acids are introduced in vitro or in vivo in a host.

Such techniques include transfection of nucleic acid-$CaPO_4$ precipitates, transfection of nucleic acids associated with DEAE, transfection or infection with the foregoing viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Preferred antibodies include antibodies which selectively bind a cancer associated antigen, alone or as a complex with a MHC molecule. Especially preferred are monoclonal antibodies. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

When administered, the therapeutic compositions of the present invention can be administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing antibody aerosols without resort to undue experimentation. When using antisense preparations of the invention, slow intravenous administration is preferred.

The compositions of the invention are administered in effective amounts. An "effective amount" is that amount of a cancer associated antigen composition that alone, or together with further doses, produces the desired response, e.g. increases an immune response to the cancer associated antigen. In the case of treating a particular disease or condition characterized by expression of one or more cancer associated antigens, such as seminoma, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of cancer associated antigen or nucleic acid encoding cancer associated antigen for producing the desired response in a unit of weight or volume suitable for administration to a patient. The response can, for example, be measured by determining the immune response following administration of the cancer associated antigen composition via a reporter system by measuring downstream effects such as gene expression, or by measuring the physiological effects of the cancer associated antigen composition, such as regression of a tumor or decrease of disease symptoms. Other assays will be known to one of ordinary skill in the art and can be employed for measuring the level of the response.

The doses of cancer associated antigen compositions (e.g., polypeptide, peptide, antibody, cell or nucleic acid) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, for treatments for eliciting or increasing an immune response, doses of cancer associated antigen are formulated and administered in doses between 1 ng and 1 mg, and preferably between 10 ng and 100 $\mu$g, according to any standard procedure in the art. Where nucleic acids encoding cancer associated antigen of variants thereof are employed, doses of between 1 ng and 0.1 mg generally will be formulated and administered according to standard procedures. Other protocols for the administration of cancer associated antigen compositions will be known to one of ordinary skill in the art, in which the dose amount, schedule of injections, sites of injections, mode of administration (e.g., intra-tumoral) and the like vary from the foregoing. Administration of cancer associated antigen compositions to mammals other than humans, e.g. for testing purposes or veterinary therapeutic purposes, is carried out under substantially the same conditions as described above.

Where cancer associated antigen peptides are used for vaccination, modes of administration which effectively deliver the cancer associated antigen and adjuvant, such that an immune response to the antigen is increased, can be used. For administration of a cancer associated antigen peptide in adjuvant, preferred methods include intradermal, intravenous, intramuscular and subcutaneous administration. Although these are preferred embodiments, the invention is not limited by the particular modes of administration disclosed herein. Standard references in the art (e.g., *Remington's Pharmaceutical Sciences*, 18th edition, 1990) provide modes of administration and formulations for delivery of immunogens with adjuvant or in a non-adjuvant carrier.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A cancer associated antigen composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal (not preferred for pediatric applications).

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation of cancer associated antigen polypeptides or nucleic acids, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

EXAMPLES

Materials and Methods

Sera, tissues and cell lines. Sera were obtained during routine diagnostic or therapeutic procedures. Sera were stored at −80° C. until use. Tumor specimens were obtained from the Departments of Pathology at the Memorial Sloan-Kettering Cancer Center and New York Hospital-Cornell Medical Center. The lung cancer cell lines used in this study were from the cell bank of the Ludwig Institute for Cancer Research, New York Branch at Memorial Sloan-Kettering Cancer Center.

Reverse transcribed PCR. Total RNA from tumor specimens and cell lines was prepared by the guanidinium thiocyanate method. Total RNA from various normal tissues was obtained commercially (Clontech Laboratories, Inc. Palo Alto, Calif.).

The mRNA expression patterns of RING3 (SEQ ID NO:1), KIAA0043 (SEQ ID NO:2), HUNK1 (SEQ ID NO:3) and BRDT (SEQ ID NO:4) were determined by RT-PCR using a panel of normal tissue RNA. The initial test panel consisted of RNA from lung, testis, small intestine, breast, liver, brain and placenta. In the case of BRDT expression, RNA samples from various tumor specimens, tumor cell lines and additional normal tissues (spleen, kidney, skeletal muscle pancreas, adrenal gland, heart, thymus, uterus and prostate) were also analyzed by RT-PCR. The cDNA preparations used in the RT-PCR reactions were synthesized by incubating total RNA template (2 μg), random hexamers (1.66 μg, Boehringer Mannheim, Indianapolis, Ind.) and MuLV reverse transcriptase (200U, Gibco BRL), in a total reaction volume of 25 μl, at 42° C. for 1 hour. MuLV synthesized cDNA (2.5 μl/PCR reaction) was them amplified using gene specific primers (0.2 μM and AmpliTaq Gold DNA polymersase (2.5 U, PE Applied Biosystems, Branchburg, N.J.) in 25 μl PCR reactions consisting of 30 cycles at a denaturation temperature of 94° C. (1 min/cycle); an annealing temperature of 60° C. (1 min/cycle); and an extension temperature of 72° C. (2 min/cycle). As a control for genomic DNA contamination in the RT-PCR reactions, duplicate cDNA templates were prepared as above in the absence of MuLV reverse transcriptase and used in equivalent PCR reactions. In addition to RT-PCR product identification on the basis of size, selected products were subcloned into pCR2.1 (Invitrogen, San Diego, Calif.) and multiple clones were subjected to automated DNA sequencing (Cornell University DNA services, Ithaca, N.Y.). The gene specific amplification primers used in RT-PCR reactions of RING3 gene family members are as follows:

BDRT Forward 5' TCAAGAAAGGCACTCAACAG (bp 544; SEQ ID NO:5);

BRDT Reverse 5' TTCACTACTTGCTTTAACTGC (bp 797; SEQ ID NO:6);

RING3 Forward 5' GGGAAGGGAATGCAGGGTTG (bp 1074; SEQ ID NO:7);

RING3 Reverse 5' TGGCTGTTCTTAGGGATGGTC (bp 1623; SEQ ID NO:8);

KIAA0043 Forward 5' TAATGGCCCAAGCTTTAGAG (bp 510; SEQ ID NO:9);

KIAA0043 Reverse 5' GTTTGCAGTGATGGTTGG TAC (bp 760; SEQ ID NO:10);

HUNK1 Forward 5'AGCACCCAGCACCAGAGAAG (bp 1241; SEQ ID NO:11); and

HUNK1 Reverse 5' TGCTGCTGTCGCTGGATGAG (bp 1690; SEQ ID NO:12). Gene specific primers for a panel of CT antigens including SCP-1 (SEQ ID NO:13), NY-ESO-1(SEQ ID NO:14), CT7 (SEQ ID NO:15), HOM-MEL-40/SSX2 (SEQ ID NO:16), SSX4 (SEQ ID NO:17), MAGE-A1 (SEQ ID NO:18) and MAGE-A3 (SEQ ID NO:19), were prepared according to published sequences.

Nuclease protection assays. A $^{32}$P labeled singled-stranded antisense DNA probe corresponding to nucleotides 544–797 of BRDT was prepared using the Prime-A-Probe kit as per the manufacturer's protocol (Ambion, Austin Tex.). Total RNA (20 µg) preparations from various normal tissues (testis, liver, prostate, placenta, spleen, kidney, mammary gland), 2 lung cancer specimens, normal lung tissue from the same patients, and the SK-LC-5 lung cancer cell line were hybridized with $2.0 \times 10^5$ cpm BRDT probe (specific activity=$5 \times 10^9$ cpm/pg) at 44° C. for 16 hours. Samples were then digested with 10 U of S1 nuclease at 37° C. for 1 hour and electrophoresed on a 8M urea/5%polyacrylamide/TBE gel. The protected fragments were visualized by autoradiography.

Immunoscreening of transfectants. Sera (diluted 1:500) from cancer patients were used to immunoscreen for clones reactive with IgG antibodies as described in detail previously (Sahin, et al., *Proc. Natl. Acad. Sci. USA*, 92:11810–11813, 1995; Türeci et al., *Cancer Res.* 56:4766–4772, 1996).

Example 1

Identification of BRDT as a Cancer-testis Antigen

SEREX analysis of human breast cancer identified the RING3 gene product as an antigen that reacts with autologous antibody. RING3 was originally defined as the human homologue to the Drosophila female sterile homeotic (fsh) protein. It is a nuclear serine-threonine kinase containing 2 copies of the bromo domain, a motif of approximately 100 amino acids found in several mammalian, invertebrate and yeast transcriptional regulators. Preliminary expression analysis based on the tissue distribution of identical expressed sequence tags (ESTs) indicates that RING3 is expressed in a wide range of normal tissues. A database search of proteins displaying a high degree of similarity to RING3 revealed a testis specific transcript, termed the bromo domain testis-specific gene product (BRDT), which shares 52% amino acid identity with RING3. BRDT is a putative nuclear protein of 947 amino acids (108 kDa), also containing two copies of the bromo domain. The region in BRDT with similarity to serine/threonine kinase domains, is lacking in essential subdomains required for catalytic activity indicating that it does not function as a kinase. Initial characterization studies reported RNA expression of BRDT to be restricted to testis. In addition to BRDT, two uncharacterized members of the human RING3 gene family have also been identified, KIAA0043 and HUNK1 (unpublished GenBank submission Y12059). An analysis of identical EST sequences showed that expression of KIAA0043 and HUNK1 transcripts is not tissue restricted.

The current study examined the mRNA expression pattern of BRDT in normal and malignant tissues to determine if it has an expression profile similar to CT antigens. In addition, the co-expression patterns of various CT antigens and BRDT were evaluated in a series of lung cancer specimens.

As shown in Table 1, seventeen different normal tissue RNA samples were analyzed for BRDT expression by RT-PCR. A BRDT/CT9 specific fragment of 250 bp was obtained using BRDT/CT9 gene specific primers. Only testis and placenta were positive for BRDT mRNA expression. Subsequent RT-PCR expression analysis of BRDT in tumor tissue (Table 1) revealed expression in 12 of 47 (25%) non-small cell lung cancer specimens (NSCLC), 1 of 12 (8%) esophageal cancer specimens and in 1 of 12 (8%) squamous cell carcinomas of the head and neck. BRDT mRNA was not detected in melanoma (12 cases), colon cancer (6 cases), breast cancer (18 cases), renal cancer (6 cases), and bladder cancer (12 cases). Also, it was not detected in available normal lung tissue (3 cases) from BRDT positive lung cancer patients. The PCR products obtained from testis and lung cancer were subcloned and subjected to DNA sequencing. The resultant DNA sequences were identical to BRDT. Thus, this cancer/testis (placenta) expression profile of BRDT was similar to the expression profile of CT antigens and accordingly, it was given the CT designation CT9. BRDT transcript expression was also analyzed in fifteen lung cancer cell lines (Table 1). Only the SK-LC-5 cell line demonstrated BRDT expression by RT-PCR. Expression of RING3, KIAA0043 and HUNK1 mRNA was also determined by RT-PCR and was found to be universal in a panel consisting of normal lung, testis, small intestine, breast, liver, brain and placenta RNA.

Table 1. Expression BRDT/CT9 mRNA in various normal human tissues, tumor tissue and lung cancer cell lines as determined by RT-PCR.

| Normal Tissue | RT-PCR |
|---|---|
| Testis | + |
| Breast | Neg. |
| Liver | Neg. |
| Sm. Intest. | Neg. |
| Brain | Neg. |
| Lung | Neg. |
| Fetal Brain | Neg. |
| Placenta | + |
| Spleen | Neg. |
| Kidney | Neg. |
| Skel. Muscle | Neg. |
| Pancreas | Neg. |
| Adrenal | Neg. |
| Heart | Neg. |
| Thymus | Neg. |
| Uterus | Neg. |
| Prostate | Neg. |
| Tumor Tissue | |
| Lung Cancer | 12/47 |
| Colon Cancer | 0/6 |
| Melanoma | 0/12 |
| Breast Cancer | 0/18 |
| SQCC of Head and Neck | 1/12 |
| Bladder Cancer | 0/13 |
| Esophageal Cancer | 1/12 |
| Renal Cancer | 0/6 |

-continued

| Lung Tumor Cell Lines | |
|---|---|
| SK-LC-1 | Neg. |
| SK-LC-2 | Neg. |
| SK-LC-3 | Neg. |
| SK-LC-5 | + |
| SK-LC-6 | Neg. |
| SK-LC-7 | Neg. |
| SK-LC-8 | Neg. |
| SK-LC-14 | Neg. |
| SK-LC-17 | Neg. |
| SW1271 | Neg. |
| CaLu-1 | Neg. |
| CaLu-3 | Neg. |
| KNS-62 | Neg. |
| NCI-H740 | Neg. |

Example 2

Analysis of BRDT Expression by S1 Nuclease Assay

S1 nuclease protection assays were performed to confirm the RT-PCR results of BRDT mRNA expression. A BRDT protected fragment of 250 bases is present only in normal testis, 2 lung cancer specimens and the SK-LC-5 cell line. S1 nuclease failed to detect BRDT expression in normal liver, prostate, placenta, spleen, kidney, mammary gland and normal lung tissue from lung cancer patients whose tumors were BRDT positive. The ability to detect weak BRDT expression in placenta by RT-PCR, but not by S1 nuclease protection, probably reflects the ability of RT-PCR to detect trace levels of mRNA. In this regard, the restricted tissue distribution of BRDT/CT-9 mRNA is not absolute. Under exhaustive RT-PCR conditions of 35 amplification cycles, weak expression, as determined by presence of faint signals of appropriate size fragments, were obtained in some normal issues and other tumor types. Normal tissues that showed weak BRDT mRNA expression at 35 PCR cycles failed to yield corresponding BRDT protected fragments in S1 nucleus protection assays. Thus, it was concluded that weak BRDT expression at 35 PCR cycles likely represents leaky expression of questionable biological significance.

Example 3

Expression of BRDT in Lung Cancer

Table 2 shows BRDT mRNA expression as a function of the histological type of lung cancer. Of the twelve BRDT positive lung cancers, the majority were moderately differentiated adenocarcinomas (42%) and undifferentiated large cell carcinomas (33%). Among the eleven undifferentiated large cell carcinomas tested, 36% (4/11) were positive for expression of BRDT transcripts. Of the 17 moderately differentiated adenocarcinomas, 29% (5/17) showed expression of this transcript. Single cases of squamous cell carcinoma (1/6), poorly differentiated adenocarcinoma (1/8) and adenocarcinoma of the bronchioloalveolar type (1/2) were positive for BRDT transcript expression. SK-LC-5, the only lung cancer cell line that tested positive for BRDT expression (Table 1), was derived from a large cell carcinoma.

Table 2. BRDT/CT9 mRNA expression in lung cancer as a function of the histological type

| Lung Cancer Type | RT-PCR Positive Tumors |
|---|---|
| Undifferentiated Large Cell Carcinoma | 4/11 |
| Squamous Cell Carcinoma | 1/6 |
| Poorly Differentiated Adenocarcinoma | 1/8 |
| Moderately Differentiated Adenocarcinoma | 5/17 |
| Well Differentiated Adenocarcinoma | 0/1 |
| Adenocarcinoma (Papilary) | 0/1 |
| Adenocarcinoma (Bronchioloalveolar) | 1/2 |
| Poorly Differentiated Carcinosarcoma | 0/1 |

Example 4

Expression of Multiple CT Antigens in Lung Cancer

In order to place BRDT mRNA expression in the context of general CT antigen expression, a series of 33 lung cancer specimens were co-typed for expression of MAGE-A1, MAGE-A3, HOM-MEL-40/SSX-2, SSX-4, NY-ESO-1, SCP-1, CT7 and BRDT/CT9 transcripts by RT-PCR. As shown in Table 3, twenty-two of thirty-three lung cancer specimens (67%) showed expression of at least 1 of the transcripts in this panel. MAGE-3 transcripts were detected most often (60% of the specimens), followed by MAGE-1 (36% of the specimens), CT7 (30%), SSX4 (23%), BRDT (21%), NY-ESO-1 (21%), HOM-MEL-40/SSX2 (15%) and SCP-1 (3%). Of the twenty-two lung cancers that tested positive for transcripts encoding CT antigens, twenty were positive for MAGE-A3. The two exceptions were a specimen that expressed only MAGE-A1 transcripts and another that expressed both BRDT and SSX-4 transcripts. Of the eleven lung cancer specimens that did not express transcripts encoding any of the nine CT antigens analyzed, nine were adenocarcinomas of various states of differentiation, one was a squamous cell carcinoma and one was a carcinosarcoma. The staining intensities of the resultant PCR products varied from weak to intense (+ to +++, Table 3), likely reflecting the mRNA abundance level. In general, strong signals were associated with MAGE-A3, MAGE-A1, NY-ESO-1 and BRDT transcripts. The very faint RT-PCR signals (Table 3, designated Neg.*) obtained from certain tumor samples are of questionable biological significance. These samples were included among the eleven negative cases.

TABLE 3

CT antigens in non-small cell lung cancer by RT-PCR

| Lung Cancer | MAGE 1 | MAGE 3 | SSX2 | SSX4 | NY-ESO-1 | SCP1 | CT7 | BRDT/CT9 | Total Number Positive CT Angtigens |
|---|---|---|---|---|---|---|---|---|---|
| Lu-2 | Neg | + | Neg | Neg | Neg | Neg | Neg* | +++ | 2 |
| Lu-4 | +++ | +++ | + | ++ | +++ | Neg | ++ | +++ | 7 |
| Lu-5 | Neg | + | Neg | ++ | Neg | Neg | + | Neg | 3 |
| Lu-6 | ++ | +++ | Neg | Neg | Neg | Neg | Neg | Neg | 2 |
| Lu-7 | Neg | +++ | + | Neg* | +++ | Neg | ++ | Neg | 4 |

TABLE 3-continued

CT antigens in non-small cell lung cancer by RT-PCR

| Lung Cancer | MAGE 1 | MAGE 3 | SSX2 | SSX4 | NY-ESO-1 | SCP1 | CT7 | BRDT/CT9 | Total Number Positive CT Antigens |
|---|---|---|---|---|---|---|---|---|---|
| Lu-9 | Neg | Neg* | Neg | Neg | Neg | Neg | Neg* | Neg | 0 |
| Lu-10 | Neg | + | Neg | Neg* | Neg | Neg | Neg | Neg | 1 |
| Lu-14 | Neg | Neg | Neg | Neg* | Neg | Neg | Neg | Neg | 0 |
| Lu-16 | ++ | ++= | Neg | Neg | Neg | Neg | + | Neg | 3 |
| Lu-17 | Neg | Neg | Neg | Neg | Neg | Neg | Neg | Neg | 0 |
| Lu-18 | Neg | Neg* | Neg | Neg | Neg | Neg | Neg | Neg | 0 |
| Lu-19 | ++ | +++ | Neg* | Neg | +++ | Neg | Neg | Neg | 3 |
| Lu-21 | +++ | +++ | + | + | +++ | Neg | ++ | Neg | 6 |
| Lu-22 | +++ | Neg* | Neg | Neg | Neg | Neg | Neg* | Neg | 1 |
| Lu-23 | Neg | Neg | Neg | Neg | Neg | Neg | Neg | Neg | 0 |
| Lu-24 | Neg | + | Neg | Neg* | Neg | Neg | Neg | +++ | 2 |
| Lu-28 | Neg | +++ | Neg | Neg | Neg | Neg | Neg | Neg | 1 |
| Lu-29 | Neg | Neg | Neg | + | Neg | Neg | Neg | ++ | 2 |
| Lu-38 | + | +++ | Neg | + | Neg | Neg | +++ | Neg | 4 |
| Lu-39 | Neg | Neg | Neg | Neg | Neg | Neg | Neg | Neg | 0 |
| Lu-40 | +++ | +++ | Neg | Neg | Neg | Neg | Neg* | ++ | 3 |
| Lu-43 | Neg | + | Neg | Neg | Neg | Neg | Neg* | + | 2 |
| Lu-44 | ++ | +++ | Neg | Neg | Neg | Neg | Neg* | +++ | 3 |
| Lu-46 | +++ | +++ | + | +++ | + | Neg | + | Neg | 6 |
| Lu-47 | Neg | +++ | Neg | Neg | Neg | + | Neg* | Neg | 2 |
| Lu-51 | Neg | Neg | Neg | Neg | Neg | Neg | Neg | Neg | 0 |
| Lu-53 | Neg* | Neg | Neg | Neg* | Neg | Neg | Neg* | Neg | 0 |
| Lu-54 | +++ | +++ | + | + | +++ | Neg | + | Neg | 6 |
| Lu-55 | Neg | Neg | Neg | Neg* | Neg | Neg | Neg | Neg | 0 |
| Lu-57 | Neg | Neg | Neg | Neg | Neg | Neg | Neg | Neg | 0 |
| Lu-58 | +++ | +++ | Neg | + | + | Neg | + | Neg | 5 |
| Lu-63 | Neg | Neg | Neg | Neg | Neg | Neg | Neg | Neg | 0 |
| Lu-65 | Neg | ++ | Neg | Neg | Neg | Neg | + | Neg | 2 |
| Totals | 12/33 (36%) | 20/33 (60%) | 5/33 (15%) | 8/33 (24%) | 7/33 (21%) | 1/33 (3%) | 10/33 (30%) | 7/33 (21%) | Frequency of CT expression = 22/33 or 67% |

Expression of CT antigen transcripts in lung cancer appears to be clustered. In these studies, 11 of 33 lung tumors (36%) lacked reliable expression of any of the eight CT antigens tested and 3 of 33 lung tumors (9%) express only one of the antigens tested (2 cases of MAGE-A3 expression and 1 case of MAGE-A1 expression). On the other hand, 19 of 33 patients (57%) express 2 or more antigens and 12 of 33 (36%) express 3 or more of these antigens. A summary of the co-typing data is shown in Table 4. In terms of BRDT mRNA expression, it did not consistently co-type with 5 of the 6 relevant CT antigens, the exception being MAGE-A3. Of the seven BRDT positive lung tumors, 43% were positive for MAGE-A1; 86% were positive for MAGE-A3; 28% were positive for SSX-4 and 14% was positive for HOM-MEL-40/SSX-2, NY-ESO-1 and CT-7. No lung cancer specimen was exclusively BRDT positive. In contrast, six of the remaining seven CT antigens (SCP-1 is the exception) had a higher incidence of coexpression. For example, all of the five HOM-Mel-40/SSX2 positive tumors express MAGE-A3, NY-ESO-1 and CT7 and 80% express MAGE-A1 and SSX-4. Only 20% of the HOM-MEL-40/SSX-2 positive tumors express BRDT/CT-9. Furthermore, of the seven NY-ESO-1 positive lung tumors, all express MAGE A3, 86% express MAGE-A1 and CT7, 71% express HOM-MEL-40/SSX-2 and SSX-4 and 14% express BRDT/CT-9.

TABLE 4

The incidence of CT antigen coexpression in non-small lung cancer.

| Reference CT Antigen | Co-typing CT Antigens | | | | | | | |
|---|---|---|---|---|---|---|---|---|
| | MAGE-A1 | MAGE-A3 | SSX2 | SSX4 | NY-ESO-1 | SCP1 | CT7 | BRDT/CT9 |
| MAGE-A1 | X | 11/12 | 4/12 | 6/12 | 6/12 | 0/12 | 7/12 | 3/12 |
| MAGE-A3 | 11/20 | X | 5/20 | 7/20 | 7/20 | 1/20 | 10/20 | 6/20 |
| SSX2 | 4/5 | 5/5 | X | 4/5 | 5/5 | 0/5 | 5/5 | 1/5 |
| SSX4 | 6/5 | 7/8 | 4/8 | X | 5/8 | 0/8 | 7/8 | 2/8 |
| NY-ESO-1 | 6/7 | 7/7 | 5/7 | 5/7 | X | 0/7 | 6/7 | 1/7 |
| SCP1 | 1/1 | 0/1 | 0/1 | 0/1 | 0/1 | X | 0/1 | 0/1 |
| CT7 | 7/10 | 10/10 | 5/10 | 7/10 | 6/10 | 0/10 | X | 1/10 |
| BRDT/CT9 | 3/7 | 6/7 | 1/7 | 2/7 | 1/7 | 0/7 | 1/7 | X |

Data were derived from Table 3.

The expression profile of CT9/BRDT in cancer and its potential transcriptional regulatory activity make it an interesting molecule for future immunological and functional investigation. Immunologically, the ability of BRDT/CT9 or peptide derivatives to stimulate T lymphocyte reactivity is imperative for it to be considered a candidate molecule for tumor vaccines. In this regard, the current study has assembled a group of CT antigens for further studies aimed at generating a polyvalent lung cancer vaccine(s). A minimal panel, covering all CT-antigen positive tumors (67% of all NSCLC specimens tested) and all but 1 case of multi-CT antigen expression, would consist of MAGE-A3, MAGE-A1, NY-ESO-1, BRDT/CT9, CT7 and SSX-4. With such a panel, the frequency of CT antigen coexpression within the subgroup CT antigen positive tumors examined in the current study is 82%, 59%, 45%, 27% and 23% for expression of two, three, four, five and six of these CT antigens, respectively. Thus, such a panel represents a promising repertoire of target antigens for a polyvalent cancer vaccine to be used in the treatment of lung cancer.

Example 5

Identification of the Portion of a Cancer Associated Polypeptide Encoding an Antigen Antigens which provoke an antibody response in a subject may also provoke a cell-mediated immune response. Cells process proteins into peptides for presentation on MHC class I or class II molecules on the cell surface for immune surveillance. Peptides presented by certain MHC/HLA molecules generally conform to motifs. These motifs are known in some cases, and can be used to screen the cancer associated antigens for the presence of potential class I and/or class II peptides. Summaries of class I and class II motifs have been published (e.g., Rammensee et al., *Immunogenetics* 41:178–228, 1995). Based on the results of experiments such as those described above, the HLA types which present the individual cancer associated antigens are known. Motifs of peptides presented by these HLA molecules thus are preferentially searched.

One also can search for class I and class II motifs using computer algorithms. For example, computer programs for predicting potential CTL epitopes based on known class I motifs has been described (see, e.g., Parker et al, *J. Immunol.* 152:163, 1994; D'Amaro et al., *Human Immunol.* 43:13–18, 1995; Drijfhout et al., *Human Immunol.* 43:1–12, 1995). HLA binding predictions can conveniently be made using an algorithm available via the Internet on the National Institutes of Health World Wide Web site at URL http://bimas.dcrt.nih.gov, for example, using default settings.

To determine if the cancer associated antigens isolated as described above can provoke a cytolytic T lymphocyte response, the following method is performed for generation of CD8$^+$ T cells using the predicted HLA peptides described above.

Briefly, peripheral blood mononuclear cells (PBMCs) are isolated using Ficoll-Hypaque (Pharmacia) from blood of HLA-A201$^+$ healthy donors (or donors positive for whatever HLA binding peptide is being investigated). Adherent monocytes are separated from non-adherent peripheral blood lymphocytes (PBLs) by plastic adherence via overnight incubation at 37° C. on plastic. The non-adherent PBLs are cryopreserved until needed, while adherent cells are stimulated to differentiate into dendritic cells (DCs) by incubation in AIMV-medium (Gibco), containing 1000 U/ml IL-4 and 1000 U/ml GM-CSF for 5 days.

On day 7, $8 \times 10^5$ DCs are loaded with 50 mg/ml exogenously added peptide for 2 hours at 37° C. in medium containing 1000 U/ml TNFα and 10,000 U/ml IL-1β. The peptide pulsed DCs are then washed twice in excess medium containing no peptide. Autologous PBLs are thawed and $4 \times 10^7$ PBLs are coincubated with $8 \times 10^5$ peptide loaded DCs (ratio 50:1), in medium containing 5 ng/ml IL-7 and 20 U/ml IL-2. These cultures are then incubated at 37° C.

On days 14, 21 and 28 the lymphocyte cultures are further stimulated with autologous peptide pulsed DC cells as for day 7. Functional assays such as Elispot and cytotoxicity assays are done on days 14, 21 and/or 28. The Elispot assays are performed using commercially available Elispot-system for IFN-γ; NC plates from Millipore; antibodies from Holzel, following manufacturers instructions. The cytotoxicity assays are performed using a Europium labelling based assay which is analogous to chromium release type assay (Blomberg et al., *J. Immunol Methods* 114:191–195, 1988).

A similar method is performed to determine if the cancer associated antigen contains one or more HLA class II peptides recognized by T cells. One can search the sequence of the cancer associated antigen polypeptides for HLA class II motifs as described above. In contrast to class I peptides, class II peptides are presented by a limited number of cell types. Thus for these experiments, dendritic cells or B cell clones which express HLA class II molecules preferably are used.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A method of diagnosing lung, cancer, comprising:

contacting a biological sample comprising lung, cells from a subject with a probe that hybridizes under high-stringency hybridization conditions to a nucleic acid molecule consisting of the nucleotide sequence of SEQ ID NO:4, or a full-length complement thereof, wherein the high-stringency hybridization conditions are hybridization at 65° C. in hybridization buffer (3.5× SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA) and wherein SSC is 0.15M sodium chloride/0.015M sodium citrate, pH7; SDS is sodium dodecyl sulphate; and EDTA is ethylenediaminetetracetic acid, and determining expression of the nucleic acid molecule or its full-length complement in the sample by measuring hybridization of the probe to the nucleic acid molecule or its full-length complement, wherein the expression of the nucleic acid molecule or its full-length complement is diagnostic for lung cancer in the sample.

2. The method of claim 1, wherein the probe is a second nucleic acid molecule comprising the nucleic acid molecule that selectively binds to a full-length complement of the nucleic acid molecule.

3. The method of claim 1, wherein the expression of the nucleic acid molecule in the sample is determined by determining the binding between the probe and the nucleic acid molecule, or the fragment of the nucleic acid molecule produced by nucleic acid amplification of the nucleic acid set forth as SEQ ID NO:4.

4. The method of claim 1, further comprising a reverse transcription polymerase chain reaction (RT-PCR) amplification.

* * * * *

UNITED STATES PATENT AND TRADEMARK OFFICE
CERTIFICATE OF CORRECTION

PATENT NO. : 6,686,147 B1  
DATED : February 3, 2004  
INVENTOR(S) : Matthew J. Scanlan et al.

It is certified that error appears in the above-identified patent and that said Letters Patent is hereby corrected as shown below:

<u>Column 113,</u>  
Line 12, should read -- A method of diagnosing lung cancer, comprising: --  
Line 13, should read -- contacting a biological sample comprising lung cells --

Signed and Sealed this

Twentieth Day of April, 2004

JON W. DUDAS  
*Acting Director of the United States Patent and Trademark Office*